(12) United States Patent
Murphy

(10) Patent No.: US 6,951,721 B2
(45) Date of Patent: *Oct. 4, 2005

(54) METHOD FOR DETERMINING THE HAPLOTYPE OF A HUMAN BRCA1 GENE

(75) Inventor: Patricia D. Murphy, Slingerlands, NY (US)

(73) Assignee: Gene Logic Inc., Gaithersburg, MD (US)

(*) Notice: Subject to any disclaimer, the term of this patent is extended or adjusted under 35 U.S.C. 154(b) by 87 days.

This patent is subject to a terminal disclaimer.

(21) Appl. No.: 09/923,327

(22) Filed: Aug. 8, 2001

(65) Prior Publication Data

US 2003/0096236 A1 May 22, 2003

Related U.S. Application Data

(63) Continuation-in-part of application No. 09/084,471, filed on May 22, 1998, and a continuation-in-part of application No. 08/905,772, filed on Aug. 4, 1997, now abandoned, which is a continuation-in-part of application No. 08/798,691, filed on Feb. 12, 1997, now Pat. No. 5,750,400, which is a continuation-in-part of application No. 08/598,591, filed on Feb. 12, 1996, now Pat. No. 5,654,155.

(51) Int. Cl.[7] ........................... C12Q 1/68; C12P 19/34; C07H 21/02; C07H 21/04
(52) U.S. Cl. ........................ 435/6; 435/91.1; 435/91.2; 536/23.1; 536/23.5; 536/24.31
(58) Field of Search .................... 435/6, 91.1, 91.2; 536/23.1, 23.5, 24.31; 530/300, 350, 386

(56) References Cited

U.S. PATENT DOCUMENTS

| | | | |
|---|---|---|---|
| 4,458,066 A | 7/1984 | Caruthers et al. | 536/27 |
| 5,498,324 A | 3/1996 | Yeung et al. | 204/452 |
| 5,561,058 A | 10/1996 | Gelfand et al. | 435/912 |
| 5,578,443 A | * 11/1996 | Santamaria et al. | 435/6 |
| 5,593,840 A | 1/1997 | Bhatnagar et al. | 435/6 |
| 5,642,936 A | 7/1997 | Evans | 128/630 |
| 5,654,155 A | * 8/1997 | Murphy et al. | 435/6 |
| 5,686,246 A | 11/1997 | Kornman et al. | 435/6 |
| 5,750,400 A | * 5/1998 | Murphy et al. | 435/6 |
| 5,763,183 A | * 6/1998 | Pesonen et al. | 435/6 |

FOREIGN PATENT DOCUMENTS

| | | |
|---|---|---|
| EP | 0 699 754 A1 | 3/1996 |
| EP | 0 705 902 A1 | 4/1996 |
| EP | 0 705 903 A1 | 4/1996 |
| WO | WO 95/19369 | 7/1995 |
| WO | WO 98/05677 | 2/1998 |
| WO | WO 98/44157 | 10/1998 |

OTHER PUBLICATIONS

Beaucage et al., "Deoxynucleoside Phosphoramidites—A New Class of Key Intermediates for Deoxypolynucleotide Synthesis," *Tetrahedron Letters* 22(20):1859–1862 (1981).

Beutler et al., "Molecular Heterogeneity of Glucose–6–Phosphate Dehydrogenase A," *Blood* 74(7):2550–2555 (1989).

Beutler et al., "Mutation analysis of glucose–6–phosphate dehydrogenase (G6PD) variants in Costa Rica," *Human Genetics* 87:462–464 (1991).

Connor et al., "Detection of sickle cell $\beta^S$–globin allele by hybridization with synthetic oligonucleotides," *Proc. Natl. Acad. Sci. U.S.A.* 80:278–282 (1983).

Cooke et al., "$Pl^{A2}$ polymorphism and efficcy of aspirin," *The Lancet* 351:1253 (1998).

Couch et al., "Mutations and Polymorphisms in the Familial Early–Onset Breast Cancer (BRCA1) Gene)," *Human Mutation* 8:8–18 (1996).

Dunning et al., "Common BRCA1 variants and susceptibility to breast and ovarian cancer in the general population," *Human Molecular Genetics* 6(2):285–289 (1997).

Durocher et al., "Comparison of BRCA1 polymorphisms, rare sequence variants and/or missense mutations in unaffected and breast/ovarian cancer populations," *Human Molecular Genetics* 5(6):835–842 (1996).

Easton et al., "Genetic Linkage Analysis in Familial Breast and Ovarian Cancer: Results from 214 Families," *American Journal of Human Genetics* 52:678–701 (1993).

Friedman et al., "Confirmation of BRCA1 by analysis of germline mutations linked to breast and ovarian cancer in ten families," *Nature Genetics* 8:399–404 (1994).

Friend et al., Breast cancer information on the web, *Nature Genetics* 11:238–239 (1995).

Hirono, A. and Beutler, E., "Molecular cloning and nucleotide sequence of cDNA for human glucose–6–phosphate dehydrogenase variant A(–)," *Proc. Natl. Acad. Sci. U.S.A.* 85:3951–3954 (1988).

Holt et al., "Growth retardation and tumour inhibition by BRCA1," *Nature Genetics* 12(3):298–302 (1996).

Landgren et al., "A Ligase–Mediated Gene Detection Technique," *Science* 241:1077–1021 (1988).

Landgren et al., "DNA Diagnostics—Molecular Techniques and Automation," *Science* 242:229–237 (1988).

Liaw et al., "Germline mutations of the PTEN gene in Cowden disease, an inherited breast and thyroid cancer syndrome," *Nature Genetics* 16(1):64–67 (1997).

(Continued)

Primary Examiner—Carla J. Myers
(74) Attorney, Agent, or Firm—Morgan, Lewis & Bockius LLP

(57) ABSTRACT

Methods for identifying functional allele profiles of a given gene are disclosed. Functional allele profiles comprise the commonly occurring alleles in a population, and the relative frequencies at which such alleles of a given gene occur. Functional allele profiles are useful in treatment and diagnosis of diseases, for genetic and pharmacogenetic applications and for evaluating the degree to which the gene(s) are under selective pressure.

19 Claims, 1 Drawing Sheet

OTHER PUBLICATIONS

Maniatis et al., *Molecular Cloning: A Laboratory Manual*, Cold Spring Harbor Laboratory, NY, pp. 280–281 (1982).

Miki et al., "A Strong Candidate for the Breast and Ovarian Cancer Susceptibility Gene BRCA1," *Science* 266:66–71 (1994).

Newman et al., "The Human Platelet Alloantigens, $Pl^{A1}$ and $Pl^{A2}$ Are Associated with a Leucine$^{33}$/Proline$^{33}$ Amino Acid Polymorphism in Membrane Glycoprotein IIIa, and Are Distinguishable by DNA Typing," *Journal of Clinical Investigation* 83:1778–1781 (1989).

*PCR, A Practical Approach*, ILR Press, Eds. M.J. McPherson, P. Quirke, and G.R. Taylor (1992).

Ridker et al., "$Pl^{A1/A2}$ polymorphism of platelet glycoprotein IIIa and risks of myocardial infarction, stroke, and venous thrombosis," *The Lancet* 349:385–388 (1997).

Saiki et al., "A Novel Method for the Detection of Polymorphic Restriction Sites by Cleavage of Oligonucleotide Probes: Application to Sickle–Cell Anemia," *Bio/Technology* 3:1008–1012 (1985).

Sambrook et al., *Molecular Cloning, A Laboratory Manual*, 2$^{nd}$ Ed.; Cold Spring Harbor Laboratory Press, at 9.16–9.19 (1989).

Sharan et al., "Murine Brce1: sequence and significance for human missense mutations," *Human Molecular Genetics* 4(12):2275–2278 (1995).

Shuldiner et al., *Handbook of Endocrine Research Techniques*, de Pablo, F., Scanes, C., and Weintraub, B., eds., Academic Press, Inc., pp. 457–486 (1993).

Storey et al., "Role of a p53 polymorphism in the development of human papilloma–virus–associated cancer," *Nature* 393:229–234 (1998).

Vogelstein et al., "p53 Function and Dysfunction," *Cell* 70:523–526 (1992).

Weiss et al., "A monoclonal antibody (SZ21) specific for platelet GPIIIa distinguishes $Pl^{A1}$ from $Pl^{A2}$," *Tissue Antigens* 46:374–381 (1995).

Weiss et al., "A Polymorphism of a Platelet Glycoprotein Receptor as an Inherited Risk Factor for Coronary Thrombosis," *The New England Journal of Medicine* 334(17):1090–1094 (1996).

Molecular Biology, 2d ed., David Freifelder, auth., Jones and Bartlett Publishers, Inc. Boston, p. 37 (1987).

Mattila, P. et al., "Extensive Allelic Sequence Variation in the J Region of the Human Immunoglobulin Heavy Chain Gene Locus", *Eur. J. Immunol.*—25:2578–2582 (1995).

Morrison, N., et al., "Frequent Alleles of the Human Vitamin D Receptor Gene Are Functionally Distinct", *Garvan Institute of Medical Research*—20 (Feb. 21, 1992).

Moudallal, J., et al., "Monoclonal Antibodies as Probes of the Antigenic Structure of Tobacco Mosaic Virus", *The EMBO Journal*—1(8):1005–1010 (1982).

Hacia, J., et al., "Detection of Heterozygous Mutations in BRCA1 Using High Density Oligonucleotide Arrays and Two–Colour Fluorescence Analysis", *Nature Genetics* 14:441–447 (Dec. 1996).

Merajver, S., et al., "Risk Assessment and Presymptomatic Molecular Diagnosis in Hereditary Breast Cancer", *DNA Technology*—16(1):139–137 (Mar. 1996).

Madsen, H., et al., "A New Frequent Allele is the Missing Link in the Structural Polymorphism of the Human Mannan–Binding Protein", *Immunogenetics*—40:37–44 (1994).

Wainscoat, J., et al., "Evolutionary Relationships of Human Populations From an Analysis of Nuclear DNA Polymorphisms", *Nature*—319:491–493 (Feb. 6, 1986).

* cited by examiner

SEQUENCE LISTING

<160> NUMBER OF SEQ ID NOS: 268

<210> SEQ ID NO 1
<211> LENGTH: 19
<212> TYPE: DNA
<213> ORGANISM: Homo sapiens

<400> SEQUENCE: 1
cgcgtctgct tatgattgg                                            19

<210> SEQ ID NO 2
<211> LENGTH: 18
<212> TYPE: DNA

```
<213> ORGANISM: Homo sapiens

<400> SEQUENCE: 2
tctctgaggc gggaaagg                                                 18

<210> SEQ ID NO 3
<211> LENGTH: 20
<212> TYPE: DNA
<213> ORGANISM: Homo sapiens

<400> SEQUENCE: 3
tttttttttt tttaaggagc                                               20

<210> SEQ ID NO 4
<211> LENGTH: 21
<212> TYPE: DNA
<213> ORGANISM: Homo sapiens

<400> SEQUENCE: 4
cacattttta tttttctact c                                             21

<210> SEQ ID NO 5
<211> LENGTH: 20
<212> TYPE: DNA
<213> ORGANISM: Homo sapiens

<400> SEQUENCE: 5
gcttataaaa ttttaaagta                                               20

<210> SEQ ID NO 6
<211> LENGTH: 19
<212> TYPE: DNA
<213> ORGANISM: Homo sapiens

<400> SEQUENCE: 6
ctggaatctc ctctatcac                                                19

<210> SEQ ID NO 7
<211> LENGTH: 23
<212> TYPE: DNA
<213> ORGANISM: Homo sapiens

<400> SEQUENCE: 7
ttcatttttg cttttcttat tcc                                           23

<210> SEQ ID NO 8
<211> LENGTH: 20
<212> TYPE: DNA
<213> ORGANISM: Homo sapiens

<400> SEQUENCE: 8
atatgacaga aatatccttc                                               20

<210> SEQ ID NO 9
<211> LENGTH: 21
<212> TYPE: DNA
<213> ORGANISM: Homo sapiens

<400> SEQUENCE: 9
cagtggtata gaaatcttcg a                                             21

<210> SEQ ID NO 10
<211> LENGTH: 20
```

```
<212> TYPE: DNA
<213> ORGANISM: Homo sapiens

<400> SEQUENCE: 10
tttttttttt ttttacctga                                              20

<210> SEQ ID NO 11
<211> LENGTH: 20
<212> TYPE: DNA
<213> ORGANISM: Homo sapiens

<400> SEQUENCE: 11
actaatgagc ttgccattct                                              20

<210> SEQ ID NO 12
<211> LENGTH: 19
<212> TYPE: DNA
<213> ORGANISM: Homo sapiens

<400> SEQUENCE: 12
tgggtaactg caggttaca                                               19

<210> SEQ ID NO 13
<211> LENGTH: 18
<212> TYPE: DNA
<213> ORGANISM: Homo sapiens

<400> SEQUENCE: 13
gacttacgtg cttagttg                                                18

<210> SEQ ID NO 14
<211> LENGTH: 24
<212> TYPE: DNA
<213> ORGANISM: Homo sapiens

<400> SEQUENCE: 14
agtatatatt gtatgagttg aagg                                         24

<210> SEQ ID NO 15
<211> LENGTH: 25
<212> TYPE: DNA
<213> ORGANISM: Homo sapiens

<400> SEQUENCE: 15
gatttgtatt ctgtaaaatg agatc                                        25

<210> SEQ ID NO 16
<211> LENGTH: 23
<212> TYPE: DNA
<213> ORGANISM: Homo sapiens

<400> SEQUENCE: 16
ggcctttgct ttttaaaaat aac                                          23

<210> SEQ ID NO 17
<211> LENGTH: 22
<212> TYPE: DNA
<213> ORGANISM: Homo sapiens

<400> SEQUENCE: 17
gtctttaccc attatttata gg                                           22

<210> SEQ ID NO 18
```

```
<211> LENGTH: 22
<212> TYPE: DNA
<213> ORGANISM: Homo sapiens

<400> SEQUENCE: 18
gtatagacaa aagaattatt cc                                              22

<210> SEQ ID NO 19
<211> LENGTH: 23
<212> TYPE: DNA
<213> ORGANISM: Homo sapiens

<400> SEQUENCE: 19
ggtagtaggt atttatggaa tac                                             23

<210> SEQ ID NO 20
<211> LENGTH: 19
<212> TYPE: DNA
<213> ORGANISM: Homo sapiens

<400> SEQUENCE: 20
catgttagag catttaggg                                                  19

<210> SEQ ID NO 21
<211> LENGTH: 19
<212> TYPE: DNA
<213> ORGANISM: Homo sapiens

<400> SEQUENCE: 21
cacattgctt ctagtacac                                                  19

<210> SEQ ID NO 22
<211> LENGTH: 18
<212> TYPE: DNA
<213> ORGANISM: Homo sapiens

<400> SEQUENCE: 22
ccaggtgaca ttcagaac                                                   18

<210> SEQ ID NO 23
<211> LENGTH: 19
<212> TYPE: DNA
<213> ORGANISM: Homo sapiens

<400> SEQUENCE: 23
attcagtatt cctgtgtac                                                  19

<210> SEQ ID NO 24
<211> LENGTH: 17
<212> TYPE: DNA
<213> ORGANISM: Homo sapiens

<400> SEQUENCE: 24
cgttaccccc acaaagc                                                    17

<210> SEQ ID NO 25
<211> LENGTH: 20
<212> TYPE: DNA
<213> ORGANISM: Homo sapiens

<400> SEQUENCE: 25
atgctatgtc agtgtaaacc                                                 20
```

```
<210> SEQ ID NO 26
<211> LENGTH: 20
<212> TYPE: DNA
<213> ORGANISM: Homo sapiens

<400> SEQUENCE: 26
ccacaggaaa acaactatta                                                      20

<210> SEQ ID NO 27
<211> LENGTH: 20
<212> TYPE: DNA
<213> ORGANISM: Homo sapiens

<400> SEQUENCE: 27
taccacattt tatgtgatgg                                                      20

<210> SEQ ID NO 28
<211> LENGTH: 17
<212> TYPE: DNA
<213> ORGANISM: Homo sapiens

<400> SEQUENCE: 28
ggggtagtaa gtttccc                                                         17

<210> SEQ ID NO 29
<211> LENGTH: 18
<212> TYPE: DNA
<213> ORGANISM: Homo sapiens

<400> SEQUENCE: 29
ctcttctcat gctgtccc                                                        18

<210> SEQ ID NO 30
<211> LENGTH: 20
<212> TYPE: DNA
<213> ORGANISM: Homo sapiens

<400> SEQUENCE: 30
atagagaagc taagttaaac                                                      20

<210> SEQ ID NO 31
<211> LENGTH: 20
<212> TYPE: DNA
<213> ORGANISM: Homo sapiens

<400> SEQUENCE: 31
taattactca tgggacattc                                                      20

<210> SEQ ID NO 32
<211> LENGTH: 20
<212> TYPE: DNA
<213> ORGANISM: Homo sapiens

<400> SEQUENCE: 32
ggcactgaca gttaacacta                                                      20

<210> SEQ ID NO 33
<211> LENGTH: 18
<212> TYPE: DNA
<213> ORGANISM: Artificial sequence
<220> FEATURE:
<223> OTHER INFORMATION: M13 tail for forward primers

<400> SEQUENCE: 33
```

-continued

| | |
|---|---|
| tgtaaaacga cggccagt | 18 |

<210> SEQ ID NO 34
<211> LENGTH: 18
<212> TYPE: DNA
<213> ORGANISM: Artificial sequence
<220> FEATURE:
<223> OTHER INFORMATION: M13 tail for reverse primers

<400> SEQUENCE: 34

| | |
|---|---|
| caggaaacag ctatgacc | 18 |

<210> SEQ ID NO 35
<211> LENGTH: 19
<212> TYPE: DNA
<213> ORGANISM: Homo sapiens

<400> SEQUENCE: 35

| | |
|---|---|
| aggcactgag gtgattggc | 19 |

<210> SEQ ID NO 36
<211> LENGTH: 19
<212> TYPE: DNA
<213> ORGANISM: Homo sapiens

<400> SEQUENCE: 36

| | |
|---|---|
| tcgtagccct taagtgagc | 19 |

<210> SEQ ID NO 37
<211> LENGTH: 22
<212> TYPE: DNA
<213> ORGANISM: Homo sapiens

<400> SEQUENCE: 37

| | |
|---|---|
| tgaggcacta ttgtttgtat tt | 22 |

<210> SEQ ID NO 38
<211> LENGTH: 22
<212> TYPE: DNA
<213> ORGANISM: Homo sapiens

<400> SEQUENCE: 38

| | |
|---|---|
| tgttggtgtt gaatttttca gt | 22 |

<210> SEQ ID NO 39
<211> LENGTH: 22
<212> TYPE: DNA
<213> ORGANISM: Homo sapiens

<400> SEQUENCE: 39

| | |
|---|---|
| agagatttgg aaaatgagta ac | 22 |

<210> SEQ ID NO 40
<211> LENGTH: 19
<212> TYPE: DNA
<213> ORGANISM: Homo sapiens

<400> SEQUENCE: 40

| | |
|---|---|
| acaatgtcat cacaggagg | 19 |

<210> SEQ ID NO 41
<211> LENGTH: 18
<212> TYPE: DNA
<213> ORGANISM: Homo sapiens

```
<400> SEQUENCE: 41
tgaggtgaca gtgggtga                                                    18

<210> SEQ ID NO 42
<211> LENGTH: 20
<212> TYPE: DNA
<213> ORGANISM: Homo sapiens

<400> SEQUENCE: 42
gattactctg agacctaggc                                                  20

<210> SEQ ID NO 43
<211> LENGTH: 22
<212> TYPE: DNA
<213> ORGANISM: Homo sapiens

<400> SEQUENCE: 43
gattttctct tttccccttg gg                                               22

<210> SEQ ID NO 44
<211> LENGTH: 23
<212> TYPE: DNA
<213> ORGANISM: Homo sapiens

<400> SEQUENCE: 44
caaacaaagc ttcaacaatt tac                                              23

<210> SEQ ID NO 45
<211> LENGTH: 26
<212> TYPE: DNA
<213> ORGANISM: Homo sapiens

<400> SEQUENCE: 45
gggttttatt ttcaagtact tctatg                                           26

<210> SEQ ID NO 46
<211> LENGTH: 26
<212> TYPE: DNA
<213> ORGANISM: Homo sapiens

<400> SEQUENCE: 46
gctcagcaac tgttcaatgt atgagc                                           26

<210> SEQ ID NO 47
<211> LENGTH: 18
<212> TYPE: DNA
<213> ORGANISM: Homo sapiens

<400> SEQUENCE: 47
ctagtgtgtg ttttttggc                                                   18

<210> SEQ ID NO 48
<211> LENGTH: 18
<212> TYPE: DNA
<213> ORGANISM: Homo sapiens

<400> SEQUENCE: 48
cataacctta tctccacc                                                    18

<210> SEQ ID NO 49
<211> LENGTH: 23
<212> TYPE: DNA
```

```
<213> ORGANISM: Homo sapiens

<400> SEQUENCE: 49
ctcagccatg agacaataaa tcc                                             23

<210> SEQ ID NO 50
<211> LENGTH: 21
<212> TYPE: DNA
<213> ORGANISM: Homo sapiens

<400> SEQUENCE: 50
ggttcccaaa taatgtgatg g                                               21

<210> SEQ ID NO 51
<211> LENGTH: 21
<212> TYPE: DNA
<213> ORGANISM: Homo sapiens

<400> SEQUENCE: 51
gtttatggga aggaaccttg t                                               21

<210> SEQ ID NO 52
<211> LENGTH: 21
<212> TYPE: DNA
<213> ORGANISM: Homo sapiens

<400> SEQUENCE: 52
tggtcccata aaattccctg t                                               21

<210> SEQ ID NO 53
<211> LENGTH: 24
<212> TYPE: DNA
<213> ORGANISM: Homo sapiens

<400> SEQUENCE: 53
catgactttg tgtgaatgta cacc                                            24

<210> SEQ ID NO 54
<211> LENGTH: 24
<212> TYPE: DNA
<213> ORGANISM: Homo sapiens

<400> SEQUENCE: 54
gaggagagcc tgatagaaca tctg                                            24

<210> SEQ ID NO 55
<211> LENGTH: 20
<212> TYPE: DNA
<213> ORGANISM: Homo sapiens

<400> SEQUENCE: 55 gggcttttc tcccctccc                                                   20

<210> SEQ ID NO 56
<211> LENGTH: 18
<212> TYPE: DNA
<213> ORGANISM: Homo sapiens

<400> SEQUENCE: 56
aaaatctggg ctctcacg                                                   18

<210> SEQ ID NO 57
<211> LENGTH: 20
```

<212> TYPE: DNA
<213> ORGANISM: Homo sapiens

<400> SEQUENCE: 57
tttaatacag actttgctac                                               20

<210> SEQ ID NO 58
<211> LENGTH: 20
<212> TYPE: DNA
<213> ORGANISM: Homo sapiens

<400> SEQUENCE: 58
gaaaagccaa agttagaagg                                               20

<210> SEQ ID NO 59
<211> LENGTH: 20
<212> TYPE: DNA
<213> ORGANISM: Homo sapiens

<400> SEQUENCE: 59
tgcaacccac aaaatttggc                                               20

<210> SEQ ID NO 60
<211> LENGTH: 20
<212> TYPE: DNA
<213> ORGANISM: Homo sapiens

<400> SEQUENCE: 60
ctttctccat ttccaaaacc                                               20

<210> SEQ ID NO 61
<211> LENGTH: 18
<212> TYPE: DNA
<213> ORGANISM: Homo sapiens

<400> SEQUENCE: 61
tggtgtctct agttctgg                                                 18

<210> SEQ ID NO 62
<211> LENGTH: 20
<212> TYPE: DNA
<213> ORGANISM: Homo sapiens

<400> SEQUENCE: 62
cattgttgta gtagctctgc                                               20

<210> SEQ ID NO 63
<211> LENGTH: 21
<212> TYPE: DNA
<213> ORGANISM: Homo sapiens

<400> SEQUENCE: 63
gcagaactat gtctgtctca t                                             21

<210> SEQ ID NO 64
<211> LENGTH: 19
<212> TYPE: DNA
<213> ORGANISM: Homo sapiens

<400> SEQUENCE: 64
cggtcagttg aaatgtcag                                                19

<210> SEQ ID NO 65

```
<211> LENGTH: 19
<212> TYPE: DNA
<213> ORGANISM: Homo sapiens

<400> SEQUENCE: 65
catttggatc cgttaaagc                                                    19

<210> SEQ ID NO 66
<211> LENGTH: 23
<212> TYPE: DNA
<213> ORGANISM: Homo sapiens

<400> SEQUENCE: 66
cacccggctg gaaattttat ttg                                               23

<210> SEQ ID NO 67
<211> LENGTH: 22
<212> TYPE: DNA
<213> ORGANISM: Homo sapiens

<400> SEQUENCE: 67
ggaaaggcac tggagaaatg gg                                                22

<210> SEQ ID NO 68
<211> LENGTH: 25
<212> TYPE: DNA
<213> ORGANISM: Homo sapiens

<400> SEQUENCE: 68
ccctccagca cacatgcatg taccg                                             25

<210> SEQ ID NO 69
<211> LENGTH: 20
<212> TYPE: DNA
<213> ORGANISM: Homo sapiens

<400> SEQUENCE: 69
taagtagtct gtgatctccg                                                   20

<210> SEQ ID NO 70
<211> LENGTH: 18
<212> TYPE: DNA
<213> ORGANISM: Homo sapiens

<400> SEQUENCE: 70
atgtatgagg tcctgtcc                                                     18

<210> SEQ ID NO 71
<211> LENGTH: 18
<212> TYPE: DNA
<213> ORGANISM: Homo sapiens

<400> SEQUENCE: 71
gacaccagtg tatgttgg                                                     18

<210> SEQ ID NO 72
<211> LENGTH: 20
<212> TYPE: DNA
<213> ORGANISM: Homo sapiens

<400> SEQUENCE: 72
gagaaagaag aacacatccc                                                   20
```

```
<210> SEQ ID NO 73
<211> LENGTH: 24
<212> TYPE: DNA
<213> ORGANISM: Homo sapiens

<400> SEQUENCE: 73
gaagttgtca ttttataaac cttt                                    24

<210> SEQ ID NO 74
<211> LENGTH: 22
<212> TYPE: DNA
<213> ORGANISM: Homo sapiens

<400> SEQUENCE: 74
tgtcttttct tccctagtat gt                                      22

<210> SEQ ID NO 75
<211> LENGTH: 20
<212> TYPE: DNA
<213> ORGANISM: Homo sapiens

<400> SEQUENCE: 75
tcctgacaca gcagacatta                                         20

<210> SEQ ID NO 76
<211> LENGTH: 20
<212> TYPE: DNA
<213> ORGANISM: Homo sapiens

<400> SEQUENCE: 76
ttggatttcg ttctcactta                                         20

<210> SEQ ID NO 77
<211> LENGTH: 20
<212> TYPE: DNA
<213> ORGANISM: Homo sapiens

<400> SEQUENCE: 77
ctcttaaggg cagttgtgag                                         20

<210> SEQ ID NO 78
<211> LENGTH: 20
<212> TYPE: DNA
<213> ORGANISM: Homo sapiens

<400> SEQUENCE: 78
ttcctactgt ggttgcttcc                                         20

<210> SEQ ID NO 79
<211> LENGTH: 23
<212> TYPE: DNA
<213> ORGANISM: Homo sapiens

<400> SEQUENCE: 79
cttattttag tgtccttaaa agg                                     23

<210> SEQ ID NO 80
<211> LENGTH: 22
<212> TYPE: DNA
<213> ORGANISM: Homo sapiens

<400> SEQUENCE: 80
tttcatggac agcacttgag tg                                      22
```

```
<210> SEQ ID NO 81
<211> LENGTH: 23
<212> TYPE: DNA
<213> ORGANISM: Homo sapiens

<400> SEQUENCE: 81
cacaacaaag agcatacata ggg                                        23

<210> SEQ ID NO 82
<211> LENGTH: 20
<212> TYPE: DNA
<213> ORGANISM: Homo sapiens

<400> SEQUENCE: 82
tcgggttcac tctgtagaag                                            20

<210> SEQ ID NO 83
<211> LENGTH: 21
<212> TYPE: DNA
<213> ORGANISM: Homo sapiens

<400> SEQUENCE: 83
ttctcttcag gaggaaaagc a                                          21

<210> SEQ ID NO 84
<211> LENGTH: 21
<212> TYPE: DNA
<213> ORGANISM: Homo sapiens

<400> SEQUENCE: 84
gctgcctacc acaaatacaa a                                          21

<210> SEQ ID NO 85
<211> LENGTH: 21
<212> TYPE: DNA
<213> ORGANISM: Homo sapiens

<400> SEQUENCE: 85
ccacagtaga tgctcagtaa a                                          21

<210> SEQ ID NO 86
<211> LENGTH: 23
<212> TYPE: DNA
<213> ORGANISM: Homo sapiens

<400> SEQUENCE: 86
taggaaaata ccagcttcat aga                                        23

<210> SEQ ID NO 87
<211> LENGTH: 20
<212> TYPE: DNA
<213> ORGANISM: Homo sapiens

<400> SEQUENCE: 87
tggtcagctt tctgtaatcg                                            20

<210> SEQ ID NO 88
<211> LENGTH: 24
<212> TYPE: DNA
<213> ORGANISM: Homo sapiens

<400> SEQUENCE: 88
gtatctaccc actctcttct tcag                                       24
```

```
<210> SEQ ID NO 89
<211> LENGTH: 19
<212> TYPE: DNA
<213> ORGANISM: Homo sapiens

<400> SEQUENCE: 89
ccacctccaa ggtgtatca                                                  19

<210> SEQ ID NO 90
<211> LENGTH: 20
<212> TYPE: DNA
<213> ORGANISM: Homo sapiens

<400> SEQUENCE: 90
tgttatgttg gctccttgct                                                 20

<210> SEQ ID NO 91
<211> LENGTH: 22
<212> TYPE: DNA
<213> ORGANISM: Homo sapiens

<400> SEQUENCE: 91
cactaaagac agaatgaatc ta                                              22

<210> SEQ ID NO 92
<211> LENGTH: 22
<212> TYPE: DNA
<213> ORGANISM: Homo sapiens

<400> SEQUENCE: 92
gaagaaccag aatattcatc ta                                              22

<210> SEQ ID NO 93
<211> LENGTH: 20
<212> TYPE: DNA
<213> ORGANISM: Homo sapiens

<400> SEQUENCE: 93
tgatggggag tctgaatcaa                                                 20

<210> SEQ ID NO 94
<211> LENGTH: 22
<212> TYPE: DNA
<213> ORGANISM: Homo sapiens

<400> SEQUENCE: 94
tctgctttct tgataaaatc ct                                              22

<210> SEQ ID NO 95
<211> LENGTH: 20
<212> TYPE: DNA
<213> ORGANISM: Homo sapiens

<400> SEQUENCE: 95
agcgtcccct cacaaataaa                                                 20

<210> SEQ ID NO 96
<211> LENGTH: 20
<212> TYPE: DNA
<213> ORGANISM: Homo sapiens

<400> SEQUENCE: 96
```
tcaagcgcat gaatatgcct 20

<210> SEQ ID NO 97
<211> LENGTH: 22
<212> TYPE: DNA
<213> ORGANISM: Homo sapiens

<400> SEQUENCE: 97
gtataagcaa tatggaactc ga 22

<210> SEQ ID NO 98
<211> LENGTH: 23
<212> TYPE: DNA
<213> ORGANISM: Homo sapiens

<400> SEQUENCE: 98
ttaagttcac tggtatttga aca 23

<210> SEQ ID NO 99
<211> LENGTH: 20
<212> TYPE: DNA
<213> ORGANISM: Homo sapiens

<400> SEQUENCE: 99
gacagcgata ctttcccaga 20

<210> SEQ ID NO 100
<211> LENGTH: 21
<212> TYPE: DNA
<213> ORGANISM: Homo sapiens

<400> SEQUENCE: 100
tggaacaacc atgaattagt c 21

<210> SEQ ID NO 101
<211> LENGTH: 20
<212> TYPE: DNA
<213> ORGANISM: Homo sapiens

<400> SEQUENCE: 101
ggaagttagc actctaggga 20

<210> SEQ ID NO 102
<211> LENGTH: 22
<212> TYPE: DNA
<213> ORGANISM: Homo sapiens

<400> SEQUENCE: 102
gcagtgatat taactgtctg ta 22

<210> SEQ ID NO 103
<211> LENGTH: 22
<212> TYPE: DNA
<213> ORGANISM: Homo sapiens

<400> SEQUENCE: 103
tgggtcctta aagaaacaaa gt 22

<210> SEQ ID NO 104
<211> LENGTH: 21
<212> TYPE: DNA
<213> ORGANISM: Homo sapiens

<400> SEQUENCE: 104

```
tcaggtgaca ttgaatcttc c                                               21
```

<210> SEQ ID NO 105
<211> LENGTH: 21
<212> TYPE: DNA
<213> ORGANISM: Homo sapiens

<400> SEQUENCE: 105

```
ccactttttc ccatcaagtc a                                               21
```

<210> SEQ ID NO 106
<211> LENGTH: 22
<212> TYPE: DNA
<213> ORGANISM: Homo sapiens

<400> SEQUENCE: 106

```
tcaggatgct tacaattact tc                                              22
```

<210> SEQ ID NO 107
<211> LENGTH: 23
<212> TYPE: DNA
<213> ORGANISM: Homo sapiens

<400> SEQUENCE: 107

```
caaaattgaa tgctatgctt aga                                             23
```

<210> SEQ ID NO 108
<211> LENGTH: 20
<212> TYPE: DNA
<213> ORGANISM: Homo sapiens

<400> SEQUENCE: 108

```
tcggtaaccc tgagccaaat                                                 20
```

<210> SEQ ID NO 109
<211> LENGTH: 20
<212> TYPE: DNA
<213> ORGANISM: Homo sapiens

<400> SEQUENCE: 109

```
gcaaaagcgt ccagaaagga                                                 20
```

<210> SEQ ID NO 110
<211> LENGTH: 22
<212> TYPE: DNA
<213> ORGANISM: Homo sapiens

<400> SEQUENCE: 110

```
tatttgcagt caagtcttcc aa                                              22
```

<210> SEQ ID NO 111
<211> LENGTH: 21
<212> TYPE: DNA
<213> ORGANISM: Homo sapiens

<400> SEQUENCE: 111

```
gtaatattgg caaaggcatc t                                               21
```

<210> SEQ ID NO 112
<211> LENGTH: 22
<212> TYPE: DNA
<213> ORGANISM: Homo sapiens -continued

```
<400> SEQUENCE: 112
taaaatgtgc tccccaaaag ca                                    22

<210> SEQ ID NO 113
<211> LENGTH: 20
<212> TYPE: DNA
<213> ORGANISM: Homo sapiens

<400> SEQUENCE: 113
gtcctgccaa tgagaagaaa                                       20

<210> SEQ ID NO 114
<211> LENGTH: 21
<212> TYPE: DNA
<213> ORGANISM: Homo sapiens

<400> SEQUENCE: 114
tgtcagcaaa cctaagaatg t                                     21

<210> SEQ ID NO 115
<211> LENGTH: 21
<212> TYPE: DNA
<213> ORGANISM: Homo sapiens

<400> SEQUENCE: 115
aatggaaagc ttctcaaagt a                                     21

<210> SEQ ID NO 116
<211> LENGTH: 21
<212> TYPE: DNA
<213> ORGANISM: Homo sapiens

<400> SEQUENCE: 116
atgttggagc taggtcctta c                                     21

<210> SEQ ID NO 117
<211> LENGTH: 22
<212> TYPE: DNA
<213> ORGANISM: Homo sapiens

<400> SEQUENCE: 117
ctaacctgaa ttatcactat ca                                    22

<210> SEQ ID NO 118
<211> LENGTH: 21
<212> TYPE: DNA
<213> ORGANISM: Homo sapiens

<400> SEQUENCE: 118
gtgtataaat gcctgtatgc a                                     21

<210> SEQ ID NO 119
<211> LENGTH: 19
<212> TYPE: DNA
<213> ORGANISM: Homo sapiens

<400> SEQUENCE: 119
tggctgccca ggaagtatg                                        19

<210> SEQ ID NO 120
<211> LENGTH: 23
<212> TYPE: DNA
<213> ORGANISM: Homo sapiens
```

<400> SEQUENCE: 120
aaccagaata tctttatgta gga                                       23

<210> SEQ ID NO 121
<211> LENGTH: 22
<212> TYPE: DNA
<213> ORGANISM: Homo sapiens

<400> SEQUENCE: 121
aattcttaac agagaccaga ac                                        22

<210> SEQ ID NO 122
<211> LENGTH: 22
<212> TYPE: DNA
<213> ORGANISM: Homo sapiens

<400> SEQUENCE: 122
aaaactcttt ccagaatgtt gt                                        22

<210> SEQ ID NO 123
<211> LENGTH: 20
<212> TYPE: DNA
<213> ORGANISM: Homo sapiens

<400> SEQUENCE: 123
gtgtagaacg tgcaggattg                                           20

<210> SEQ ID NO 124
<211> LENGTH: 18
<212> TYPE: DNA
<213> ORGANISM: Homo sapiens

<400> SEQUENCE: 124
tcgcctcatg tggtttta                                             18

<210> SEQ ID NO 125
<211> LENGTH: 21
<212> TYPE: DNA
<213> ORGANISM: Homo sapiens

<400> SEQUENCE: 125
ggctctttag cttcttagga c                                         21

<210> SEQ ID NO 126
<211> LENGTH: 20
<212> TYPE: DNA
<213> ORGANISM: Homo sapiens

<400> SEQUENCE: 126
gagaccattt tcccagcatc                                           20

<210> SEQ ID NO 127
<211> LENGTH: 20
<212> TYPE: DNA
<213> ORGANISM: Homo sapiens

<400> SEQUENCE: 127
ctgtcattct tcctgtgctc                                           20

<210> SEQ ID NO 128
<211> LENGTH: 21
<212> TYPE: DNA

<213> ORGANISM: Homo sapiens

<400> SEQUENCE: 128
cattgttaag gaaagtggtg c                                       21

<210> SEQ ID NO 129
<211> LENGTH: 20
<212> TYPE: DNA
<213> ORGANISM: Homo sapiens

<400> SEQUENCE: 129
atatgacgtg tctgctccac                                         20

<210> SEQ ID NO 130
<211> LENGTH: 20
<212> TYPE: DNA
<213> ORGANISM: Homo sapiens

<400> SEQUENCE: 130
gggaatccaa attacacagc                                         20

<210> SEQ ID NO 131
<211> LENGTH: 22
<212> TYPE: DNA
<213> ORGANISM: Homo sapiens

<400> SEQUENCE: 131
aagctcttcc ttttttgaaag tc                                     22

<210> SEQ ID NO 132
<211> LENGTH: 22
<212> TYPE: DNA
<213> ORGANISM: Homo sapiens

<400> SEQUENCE: 132
gtagagaaat agaatagcct ct                                      22

<210> SEQ ID NO 133
<211> LENGTH: 20
<212> TYPE: DNA
<213> ORGANISM: Homo sapiens

<400> SEQUENCE: 133
tcccattgag aggtcttgct                                         20

<210> SEQ ID NO 134
<211> LENGTH: 20
<212> TYPE: DNA
<213> ORGANISM: Homo sapiens

<400> SEQUENCE: 134
gagaagactt ctgaggctac                                         20

<210> SEQ ID NO 135
<211> LENGTH: 21
<212> TYPE: DNA
<213> ORGANISM: Homo sapiens

<400> SEQUENCE: 135
tgaagtgaca gttccagtag t                                       21

<210> SEQ ID NO 136
<211> LENGTH: 23

<212> TYPE: DNA
<213> ORGANISM: Homo sapiens

<400> SEQUENCE: 136
cattttagcc attcattcaa caa                                    23

<210> SEQ ID NO 137
<211> LENGTH: 22
<212> TYPE: DNA
<213> ORGANISM: Homo sapiens

<400> SEQUENCE: 137
atgaattgac actaatctct gc                                     22

<210> SEQ ID NO 138
<211> LENGTH: 21
<212> TYPE: DNA
<213> ORGANISM: Homo sapiens

<400> SEQUENCE: 138
gtagccagga cagtagaagg a                                      21

<210> SEQ ID NO 139
<211> LENGTH: 24
<212> TYPE: DNA
<213> ORGANISM: Homo sapiens

<400> SEQUENCE: 139
gaataatata aattatatgg ctta                                   24

<210> SEQ ID NO 140
<211> LENGTH: 19
<212> TYPE: DNA
<213> ORGANISM: Homo sapiens

<400> SEQUENCE: 140
cctagtcttg ctagttctt                                         19

<210> SEQ ID NO 141
<211> LENGTH: 24
<212> TYPE: DNA
<213> ORGANISM: Homo sapiens

<400> SEQUENCE: 141
atctgaagtg gaaccaaatg atac                                   24

<210> SEQ ID NO 142
<211> LENGTH: 26
<212> TYPE: DNA
<213> ORGANISM: Homo sapiens

<400> SEQUENCE: 142
acgtggcaaa gaattctctg aagtaa                                 26

<210> SEQ ID NO 143
<211> LENGTH: 22
<212> TYPE: DNA
<213> ORGANISM: Homo sapiens

<400> SEQUENCE: 143
aagaagcaaa atgtaataag ga                                     22

<210> SEQ ID NO 144

```
<211> LENGTH: 22
<212> TYPE: DNA
<213> ORGANISM: Homo sapiens

<400> SEQUENCE: 144
catttaaagc acatacatct tg                                              22

<210> SEQ ID NO 145
<211> LENGTH: 21
<212> TYPE: DNA
<213> ORGANISM: Homo sapiens

<400> SEQUENCE: 145
tctagaggca aagaatcata c                                               21

<210> SEQ ID NO 146
<211> LENGTH: 22
<212> TYPE: DNA
<213> ORGANISM: Homo sapiens

<400> SEQUENCE: 146
caagattatt cctttcatta gc                                              22

<210> SEQ ID NO 147
<211> LENGTH: 22
<212> TYPE: DNA
<213> ORGANISM: Homo sapiens

<400> SEQUENCE: 147
aaccaaaaca caaatctaag ag                                              22

<210> SEQ ID NO 148
<211> LENGTH: 23
<212> TYPE: DNA
<213> ORGANISM: Homo sapiens

<400> SEQUENCE: 148 gtcatttta tatgctgctt tac                                              23

<210> SEQ ID NO 149
<211> LENGTH: 21
<212> TYPE: DNA
<213> ORGANISM: Homo sapiens

<400> SEQUENCE: 149
ggttttatat ggagacacag g                                               21

<210> SEQ ID NO 150
<211> LENGTH: 23
<212> TYPE: DNA
<213> ORGANISM: Homo sapiens

<400> SEQUENCE: 150
gtatttacaa tttcaacaca agc                                             23

<210> SEQ ID NO 151
<211> LENGTH: 20
<212> TYPE: DNA
<213> ORGANISM: Homo sapiens

<400> SEQUENCE: 151
atcacagttt tggaggtagc                                                 20
```

-continued

```
<210> SEQ ID NO 152
<211> LENGTH: 21
<212> TYPE: DNA
<213> ORGANISM: Homo sapiens

<400> SEQUENCE: 152
ctgacttcct gattcttcta a                                          21

<210> SEQ ID NO 153
<211> LENGTH: 22
<212> TYPE: DNA
<213> ORGANISM: Homo sapiens

<400> SEQUENCE: 153
accatgtagc aaatgagggt ct                                         22

<210> SEQ ID NO 154
<211> LENGTH: 22
<212> TYPE: DNA
<213> ORGANISM: Homo sapiens

<400> SEQUENCE: 154
gcttttgtct gttttcctcc aa                                         22

<210> SEQ ID NO 155
<211> LENGTH: 19
<212> TYPE: DNA
<213> ORGANISM: Homo sapiens

<400> SEQUENCE: 155
aaccacaccc ttaagatga                                             19

<210> SEQ ID NO 156
<211> LENGTH: 20
<212> TYPE: DNA
<213> ORGANISM: Homo sapiens

<400> SEQUENCE: 156
gcataagtag tggattttgc                                            20

<210> SEQ ID NO 157
<211> LENGTH: 31
<212> TYPE: DNA
<213> ORGANISM: Homo sapiens

<400> SEQUENCE: 157
gggcccggat ccatggcaat gcagatgcag c                               31

<210> SEQ ID NO 158
<211> LENGTH: 43
<212> TYPE: DNA
<213> ORGANISM: Homo sapiens

<400> SEQUENCE: 158 gggcccaat ggatatcatt cagtctttgg catctcccac tcc                   43

<210> SEQ ID NO 159
<211> LENGTH: 20
<212> TYPE: DNA
<213> ORGANISM: Homo sapiens

<400> SEQUENCE: 159
cacgaggcat ggcgctgagg                                            20
```

-continued

<210> SEQ ID NO 160
<211> LENGTH: 20
<212> TYPE: DNA
<213> ORGANISM: Homo sapiens

<400> SEQUENCE: 160
ccgggccttg tctgtccact                                               20

<210> SEQ ID NO 161
<211> LENGTH: 20
<212> TYPE: DNA
<213> ORGANISM: Homo sapiens

<400> SEQUENCE: 161
gtctacccca ttgaccatgg                                               20

<210> SEQ ID NO 162
<211> LENGTH: 20
<212> TYPE: DNA
<213> ORGANISM: Homo sapiens

<400> SEQUENCE: 162
tcatcatctg agtactgctg                                               20

<210> SEQ ID NO 163
<211> LENGTH: 20
<212> TYPE: DNA
<213> ORGANISM: Homo sapiens

<400> SEQUENCE: 163
tgcaggagga agaagacctg                                               20

<210> SEQ ID NO 164
<211> LENGTH: 20
<212> TYPE: DNA
<213> ORGANISM: Homo sapiens

<400> SEQUENCE: 164
tctgtcagcg ccaggggact                                               20

<210> SEQ ID NO 165
<211> LENGTH: 20
<212> TYPE: DNA
<213> ORGANISM: Homo sapiens

<400> SEQUENCE: 165
agcacaggcc tgctgcacct                                               20

<210> SEQ ID NO 166
<211> LENGTH: 20
<212> TYPE: DNA
<213> ORGANISM: Homo sapiens

<400> SEQUENCE: 166
gaaaagggga agtggggcag                                               20

<210> SEQ ID NO 167
<211> LENGTH: 32
<212> TYPE: DNA
<213> ORGANISM: Homo sapiens

<400> SEQUENCE: 167
agcccaggcc ccaacacagc cccatggcct ct                                 32

<210> SEQ ID NO 168
<211> LENGTH: 32
<212> TYPE: DNA
<213> ORGANISM: Homo sapiens

<400> SEQUENCE: 168
cttaggagag ttttattcat tcattgatcc ag                          32

<210> SEQ ID NO 169
<211> LENGTH: 21
<212> TYPE: DNA
<213> ORGANISM: Homo sapiens

<400> SEQUENCE: 169
aacagtacaa tgactgggct c                                      21

<210> SEQ ID NO 170
<211> LENGTH: 20
<212> TYPE: DNA
<213> ORGANISM: Homo sapiens

<400> SEQUENCE: 170
tcagcgcttc tgcacacagt                                        20

<210> SEQ ID NO 171
<211> LENGTH: 17
<212> TYPE: DNA
<213> ORGANISM: Homo sapiens

<400> SEQUENCE: 171
acatgacagc gatactt                                           17

<210> SEQ ID NO 172
<211> LENGTH: 17
<212> TYPE: DNA
<213> ORGANISM: Homo sapiens

<400> SEQUENCE: 172
acatgacagt gatactt                                           17

<210> SEQ ID NO 173
<211> LENGTH: 17
<212> TYPE: DNA
<213> ORGANISM: Homo sapiens

<400> SEQUENCE: 173
agtatttcat tggtacc                                           17

<210> SEQ ID NO 174
<211> LENGTH: 17
<212> TYPE: DNA
<213> ORGANISM: Homo sapiens

<400> SEQUENCE: 174
agtatttcac tggtacc                                           17

<210> SEQ ID NO 175
<211> LENGTH: 17
<212> TYPE: DNA
<213> ORGANISM: Homo sapiens

<400> SEQUENCE: 175

-continued catttgctcc gttttca                                                        17

<210> SEQ ID NO 176
<211> LENGTH: 17
<212> TYPE: DNA
<213> ORGANISM: Homo sapiens

<400> SEQUENCE: 176
catttgctct gttttca                                                        17

<210> SEQ ID NO 177
<211> LENGTH: 17
<212> TYPE: DNA
<213> ORGANISM: Homo sapiens

<400> SEQUENCE: 177
tttttaaaga agccagc                                                        17

<210> SEQ ID NO 178
<211> LENGTH: 17
<212> TYPE: DNA
<213> ORGANISM: Homo sapiens

<400> SEQUENCE: 178
tttttaaagg agccagc                                                        17

<210> SEQ ID NO 179
<211> LENGTH: 17
<212> TYPE: DNA
<213> ORGANISM: Homo sapiens

<400> SEQUENCE: 179
gcgtccagaa aggagag                                                        17

<210> SEQ ID NO 180
<211> LENGTH: 17
<212> TYPE: DNA
<213> ORGANISM: Homo sapiens

<400> SEQUENCE: 180
gcgtccagag aggagag                                                        17

<210> SEQ ID NO 181
<211> LENGTH: 17
<212> TYPE: DNA
<213> ORGANISM: Homo sapiens

<400> SEQUENCE: 181
aagtgactct tctgccc                                                        17

<210> SEQ ID NO 182
<211> LENGTH: 17
<212> TYPE: DNA
<213> ORGANISM: Homo sapiens

<400> SEQUENCE: 182
aagtgactcc tctgccc                                                        17

<210> SEQ ID NO 183
<211> LENGTH: 17
<212> TYPE: DNA
<213> ORGANISM: Homo sapiens

<400> SEQUENCE: 183

```
tgtgcccaga gtccagc                                              17

<210> SEQ ID NO 184
<211> LENGTH: 17
<212> TYPE: DNA
<213> ORGANISM: Homo sapiens

<400> SEQUENCE: 184
tgtgcccagg gtccagc                                              17

<210> SEQ ID NO 185
<211> LENGTH: 17
<212> TYPE: DNA
<213> ORGANISM: Homo sapiens

<400> SEQUENCE: 185
ggaataagca gaaactg                                              17

<210> SEQ ID NO 186
<211> LENGTH: 17
<212> TYPE: DNA
<213> ORGANISM: Homo sapiens

<400> SEQUENCE: 186
ggaataagcg gaaactg                                              17

<210> SEQ ID NO 187
<211> LENGTH: 17
<212> TYPE: DNA
<213> ORGANISM: Homo sapiens

<400> SEQUENCE: 187
aaaagacatg acagcga                                              17

<210> SEQ ID NO 188
<211> LENGTH: 17
<212> TYPE: DNA
<213> ORGANISM: Homo sapiens

<400> SEQUENCE: 188
aaaagacata acagcga                                              17

<210> SEQ ID NO 189
<211> LENGTH: 17
<212> TYPE: DNA
<213> ORGANISM: Homo sapiens

<400> SEQUENCE: 189
aagaagccag ctcaagc                                              17

<210> SEQ ID NO 190
<211> LENGTH: 17
<212> TYPE: DNA
<213> ORGANISM: Homo sapiens

<400> SEQUENCE: 190
aagaagccaa ctcaagc                                              17

<210> SEQ ID NO 191
<211> LENGTH: 17
<212> TYPE: DNA
<213> ORGANISM: Homo sapiens
```

```
<400> SEQUENCE: 191
catgacagtg atacttt                                                  17

<210> SEQ ID NO 192
<211> LENGTH: 17
<212> TYPE: DNA
<213> ORGANISM: Homo sapiens

<400> SEQUENCE: 192
catgacagta atacttt                                                  17

<210> SEQ ID NO 193
<211> LENGTH: 17
<212> TYPE: DNA
<213> ORGANISM: Homo sapiens

<400> SEQUENCE: 193
taggacattg gcattga                                                  17

<210> SEQ ID NO 194
<211> LENGTH: 18
<212> TYPE: DNA
<213> ORGANISM: Homo sapiens

<400> SEQUENCE: 194
taggacatgt ggcattga                                                 18

<210> SEQ ID NO 195
<211> LENGTH: 18
<212> TYPE: DNA
<213> ORGANISM: Homo sapiens

<400> SEQUENCE: 195
cttctgattt gctacatt                                                 18

<210> SEQ ID NO 196
<211> LENGTH: 18
<212> TYPE: DNA
<213> ORGANISM: Homo sapiens

<400> SEQUENCE: 196
cttctgatgt gctacatt                                                 18

<210> SEQ ID NO 197
<211> LENGTH: 18
<212> TYPE: DNA
<213> ORGANISM: Homo sapiens

<400> SEQUENCE: 197
ggcttctctg attttggt                                                 18

<210> SEQ ID NO 198
<211> LENGTH: 18
<212> TYPE: DNA
<213> ORGANISM: Homo sapiens

<400> SEQUENCE: 198
ggcttctcgg attttggt                                                 18

<210> SEQ ID NO 199
<211> LENGTH: 18
<212> TYPE: DNA
<213> ORGANISM: Homo sapiens
```

<400> SEQUENCE: 199
ttttgaatat tgtactgg                                              18

<210> SEQ ID NO 200
<211> LENGTH: 18
<212> TYPE: DNA
<213> ORGANISM: Homo sapiens

<400> SEQUENCE: 200
ttttgaatgt tgtactgg                                              18

<210> SEQ ID NO 201
<211> LENGTH: 18
<212> TYPE: DNA
<213> ORGANISM: Homo sapiens

<400> SEQUENCE: 201
attagctact tggaagac                                              18

<210> SEQ ID NO 202
<211> LENGTH: 18
<212> TYPE: DNA
<213> ORGANISM: Homo sapiens

<400> SEQUENCE: 202
attagctatt tggaagac                                              18

<210> SEQ ID NO 203
<211> LENGTH: 18
<212> TYPE: DNA
<213> ORGANISM: Homo sapiens

<400> SEQUENCE: 203
ccatttgttc atgtaatc                                              18

<210> SEQ ID NO 204
<211> LENGTH: 18
<212> TYPE: DNA
<213> ORGANISM: Homo sapiens

<400> SEQUENCE: 204
ccatttgtcc atgtaatc                                              18

<210> SEQ ID NO 205
<211> LENGTH: 18
<212> TYPE: DNA
<213> ORGANISM: Homo sapiens

<400> SEQUENCE: 205
tagcttggtt ttctaaac                                              18

<210> SEQ ID NO 206
<211> LENGTH: 18
<212> TYPE: DNA
<213> ORGANISM: Homo sapiens

<400> SEQUENCE: 206
tagcttggct ttctaaac                                              18

<210> SEQ ID NO 207
<211> LENGTH: 18
<212> TYPE: DNA

```
<213> ORGANISM: Homo sapiens

<400> SEQUENCE: 207
attgaaacaa cagaatca                                               18

<210> SEQ ID NO 208
<211> LENGTH: 18
<212> TYPE: DNA
<213> ORGANISM: Homo sapiens

<400> SEQUENCE: 208
attgaaacga cagaatca                                               18

<210> SEQ ID NO 209
<211> LENGTH: 18
<212> TYPE: DNA
<213> ORGANISM: Homo sapiens

<400> SEQUENCE: 209
tgaaaatgtg atttagtt                                               18

<210> SEQ ID NO 210
<211> LENGTH: 18
<212> TYPE: DNA
<213> ORGANISM: Homo sapiens

<400> SEQUENCE: 210
tgaaaatgcg atttagtt                                               18

<210> SEQ ID NO 211
<211> LENGTH: 18
<212> TYPE: DNA
<213> ORGANISM: Homo sapiens

<400> SEQUENCE: 211
ttccatggcc ttcctaat                                               18

<210> SEQ ID NO 212
<211> LENGTH: 18
<212> TYPE: DNA
<213> ORGANISM: Homo sapiens

<400> SEQUENCE: 212
ttccatggtc ttcctaat                                               18

<210> SEQ ID NO 213
<211> LENGTH: 18
<212> TYPE: DNA
<213> ORGANISM: Homo sapiens

<400> SEQUENCE: 213
cttgaaggcg tatacagg                                               18

<210> SEQ ID NO 214
<211> LENGTH: 18
<212> TYPE: DNA
<213> ORGANISM: Homo sapiens

<400> SEQUENCE: 214
cttgaaggtg tatacagg                                               18

<210> SEQ ID NO 215
<211> LENGTH: 19
```

```
<212> TYPE: DNA
<213> ORGANISM: Homo sapiens

<400> SEQUENCE: 215
atggcctcta ccagatggc                                                  19

<210> SEQ ID NO 216
<211> LENGTH: 19
<212> TYPE: DNA
<213> ORGANISM: Homo sapiens

<400> SEQUENCE: 216
atggcctctc ccagatggc                                                  19

<210> SEQ ID NO 217
<211> LENGTH: 19
<212> TYPE: DNA
<213> ORGANISM: Homo sapiens

<400> SEQUENCE: 217
atggcctctg ccagatggc                                                  19

<210> SEQ ID NO 218
<211> LENGTH: 19
<212> TYPE: DNA
<213> ORGANISM: Homo sapiens

<400> SEQUENCE: 218
atggcctctt ccagatggc                                                  19

<210> SEQ ID NO 219
<211> LENGTH: 19
<212> TYPE: DNA
<213> ORGANISM: Homo sapiens

<400> SEQUENCE: 219
cagatggctt tgaaaaagg                                                  19

<210> SEQ ID NO 220
<211> LENGTH: 19
<212> TYPE: DNA
<213> ORGANISM: Homo sapiens

<400> SEQUENCE: 220
cagatggctt tgcaaaagg                                                  19

<210> SEQ ID NO 221
<211> LENGTH: 19
<212> TYPE: DNA
<213> ORGANISM: Homo sapiens

<400> SEQUENCE: 221
cagatggctt tggaaaagg                                                  19

<210> SEQ ID NO 222
<211> LENGTH: 19
<212> TYPE: DNA
<213> ORGANISM: Homo sapiens

<400> SEQUENCE: 222
cagatggctt tgtaaaagg                                                  19

<210> SEQ ID NO 223
```

```
<211> LENGTH: 19
<212> TYPE: DNA
<213> ORGANISM: Homo sapiens

<400> SEQUENCE: 223
gatccaaaca ggccccttt                                                  19

<210> SEQ ID NO 224
<211> LENGTH: 19
<212> TYPE: DNA
<213> ORGANISM: Homo sapiens

<400> SEQUENCE: 224
gatccaacca ggccccttt                                                  19

<210> SEQ ID NO 225
<211> LENGTH: 19
<212> TYPE: DNA
<213> ORGANISM: Homo sapiens

<400> SEQUENCE: 225
gatccaagca ggccccttt                                                  19

<210> SEQ ID NO 226
<211> LENGTH: 19
<212> TYPE: DNA
<213> ORGANISM: Homo sapiens

<400> SEQUENCE: 226
gatccaatca ggccccttt                                                  19

<210> SEQ ID NO 227
<211> LENGTH: 19
<212> TYPE: DNA
<213> ORGANISM: Homo sapiens

<400> SEQUENCE: 227
ccctgtaaaa actggatca                                                  19

<210> SEQ ID NO 228
<211> LENGTH: 19
<212> TYPE: DNA
<213> ORGANISM: Homo sapiens

<400> SEQUENCE: 228
ccctgtaaac actggatca                                                  19

<210> SEQ ID NO 229
<211> LENGTH: 19
<212> TYPE: DNA
<213> ORGANISM: Homo sapiens

<400> SEQUENCE: 229
ccctgtaaag actggatca                                                  19

<210> SEQ ID NO 230
<211> LENGTH: 19
<212> TYPE: DNA
<213> ORGANISM: Homo sapiens

<400> SEQUENCE: 230
ccctgtaaat actggatca                                                  19
```

-continued

```
<210> SEQ ID NO 231
<211> LENGTH: 28
<212> TYPE: DNA
<213> ORGANISM: Homo sapiens

<400> SEQUENCE: 231
tcatgctgga tccccacttt tcctcttg                                          28

<210> SEQ ID NO 232
<211> LENGTH: 28
<212> TYPE: DNA
<213> ORGANISM: Homo sapiens

<400> SEQUENCE: 232
ggtggcctgc ccttccaatg gatccact                                          28

<210> SEQ ID NO 233
<211> LENGTH: 30
<212> TYPE: DNA
<213> ORGANISM: Homo sapiens

<400> SEQUENCE: 233
aattcatggg actgactttc tgctcttgtc                                        30

<210> SEQ ID NO 234
<211> LENGTH: 26
<212> TYPE: DNA
<213> ORGANISM: Homo sapiens

<400> SEQUENCE: 234
tccaggtccc agcccaaccc ttgtcc                                            26

<210> SEQ ID NO 235
<211> LENGTH: 30
<212> TYPE: DNA
<213> ORGANISM: Homo sapiens

<400> SEQUENCE: 235
gtcctctgac tgctctttc acccatctac                                         30

<210> SEQ ID NO 236
<211> LENGTH: 26
<212> TYPE: DNA
<213> ORGANISM: Homo sapiens

<400> SEQUENCE: 236
gggatacggc caggcattga agtctc                                            26

<210> SEQ ID NO 237
<211> LENGTH: 28
<212> TYPE: DNA
<213> ORGANISM: Homo sapiens

<400> SEQUENCE: 237
cttgtgccct gactttcaac tctgtctc                                          28

<210> SEQ ID NO 238
<211> LENGTH: 27
<212> TYPE: DNA
<213> ORGANISM: Homo sapiens

<400> SEQUENCE: 238
tgggcaacca gccctgtcgt ctctcca                                           27
```

<210> SEQ ID NO 239
<211> LENGTH: 29
<212> TYPE: DNA
<213> ORGANISM: Homo sapiens

<400> SEQUENCE: 239
ccaggcctct gattcctcac tgattgctc                              29

<210> SEQ ID NO 240
<211> LENGTH: 27
<212> TYPE: DNA
<213> ORGANISM: Homo sapiens

<400> SEQUENCE: 240
gccactgaca accaccctta acccctc                                27

<210> SEQ ID NO 241
<211> LENGTH: 27
<212> TYPE: DNA
<213> ORGANISM: Homo sapiens

<400> SEQUENCE: 241
gcctcatctt gggcctgtgt tatctcc                                27

<210> SEQ ID NO 242
<211> LENGTH: 28
<212> TYPE: DNA
<213> ORGANISM: Homo sapiens

<400> SEQUENCE: 242
ggccagtgtg cagggtggca agtggctc                               28

<210> SEQ ID NO 243
<211> LENGTH: 30
<212> TYPE: DNA
<213> ORGANISM: Homo sapiens

<400> SEQUENCE: 243
gtaggacctg atttccttac tgcctcttgc                             30

<210> SEQ ID NO 244
<211> LENGTH: 29
<212> TYPE: DNA
<213> ORGANISM: Homo sapiens

<400> SEQUENCE: 244
ataactgcac ccttggtctc ctccaccgc                              29

<210> SEQ ID NO 245
<211> LENGTH: 30
<212> TYPE: DNA
<213> ORGANISM: Homo sapiens

<400> SEQUENCE: 245
cacttttatc acctttcctt gcctctttcc                             30

<210> SEQ ID NO 246
<211> LENGTH: 30
<212> TYPE: DNA
<213> ORGANISM: Homo sapiens

<400> SEQUENCE: 246
aactttccac ttgataagag gtcccaagac                             30

<210> SEQ ID NO 247
<211> LENGTH: 29
<212> TYPE: DNA
<213> ORGANISM: Homo sapiens

<400> SEQUENCE: 247
acttacttct cccctcctc tgttgctgc                                    29

<210> SEQ ID NO 248
<211> LENGTH: 31
<212> TYPE: DNA
<213> ORGANISM: Homo sapiens

<400> SEQUENCE: 248
atggaatcct atggctttcc aacctaggaa g                                31

<210> SEQ ID NO 249
<211> LENGTH: 29
<212> TYPE: DNA
<213> ORGANISM: Homo sapiens

<400> SEQUENCE: 249
catctctcct ccctgcttct gtctcctac                                   29

<210> SEQ ID NO 250
<211> LENGTH: 30
<212> TYPE: DNA
<213> ORGANISM: Homo sapiens

<400> SEQUENCE: 250
ctgacgcaca cctattgcaa gcaagggttc                                  30

<210> SEQ ID NO 251
<211> LENGTH: 19
<212> TYPE: DNA
<213> ORGANISM: Homo sapiens

<400> SEQUENCE: 251
gaagcgtctc atgctggat                                              19

<210> SEQ ID NO 252
<211> LENGTH: 20
<212> TYPE: DNA
<213> ORGANISM: Homo sapiens

<400> SEQUENCE: 252
ggggactgta gatgggtgaa                                             20

<210> SEQ ID NO 253
<211> LENGTH: 19
<212> TYPE: DNA
<213> ORGANISM: Homo sapiens

<400> SEQUENCE: 253
ttttcagacc tatggaaac                                              19

<210> SEQ ID NO 254
<211> LENGTH: 19
<212> TYPE: DNA
<213> ORGANISM: Homo sapiens

<400> SEQUENCE: 254

|   |   |
|---|---|
| ttttcagatc tatggaaac | 19 |

<210> SEQ ID NO 255
<211> LENGTH: 18
<212> TYPE: DNA
<213> ORGANISM: Homo sapiens

<400> SEQUENCE: 255

|   |   |
|---|---|
| cccttgccgt cccaagca | 18 |

<210> SEQ ID NO 256
<211> LENGTH: 18
<212> TYPE: DNA
<213> ORGANISM: Homo sapiens

<400> SEQUENCE: 256

|   |   |
|---|---|
| cccttgccat cccaagca | 18 |

<210> SEQ ID NO 257
<211> LENGTH: 18
<212> TYPE: DNA
<213> ORGANISM: Homo sapiens

<400> SEQUENCE: 257

|   |   |
|---|---|
| ctgtccccgg acgatatt | 18 |

<210> SEQ ID NO 258
<211> LENGTH: 18
<212> TYPE: DNA
<213> ORGANISM: Homo sapiens

<400> SEQUENCE: 258

|   |   |
|---|---|
| ctgtccccag acgatatt | 18 |

<210> SEQ ID NO 259
<211> LENGTH: 18
<212> TYPE: DNA
<213> ORGANISM: Homo sapiens

<400> SEQUENCE: 259

|   |   |
|---|---|
| gctcccccg tggcccct | 18 |

<210> SEQ ID NO 260
<211> LENGTH: 18
<212> TYPE: DNA
<213> ORGANISM: Homo sapiens

<400> SEQUENCE: 260

|   |   |
|---|---|
| gctccccgcg tggcccct | 18 |

<210> SEQ ID NO 261
<211> LENGTH: 18
<212> TYPE: DNA
<213> ORGANISM: Homo sapiens

<400> SEQUENCE: 261

|   |   |
|---|---|
| acttttcgac atagtgtg | 18 |

<210> SEQ ID NO 262
<211> LENGTH: 18
<212> TYPE: DNA
<213> ORGANISM: Homo sapiens

<400> SEQUENCE: 262

```
acttttcggc atagtgtg                                              18

<210> SEQ ID NO 263
<211> LENGTH: 5711
<212> TYPE: DNA
<213> ORGANISM: Homo sapiens
<220> FEATURE:
<221> NAME/KEY: CDS
<222> LOCATION: (120)..(5711)
<223> OTHER INFORMATION: omi1 sequences

<400> SEQUENCE: 263
agctcgctga gacttcctgg accccgcacc aggctgtggg gtttctcaga taactgggcc     60
cctgcgctca ggaggccttc accctctgct ctgggtaaag ttcattggaa cagaaagaa    119 atg gat tta tct gct ctt cgc gtt gaa gaa gta caa aat gtc att aat    167
Met Asp Leu Ser Ala Leu Arg Val Glu Glu Val Gln Asn Val Ile Asn
1               5                   10                  15 gct atg cag aaa atc tta gag tgt ccc atc tgt ctg gag ttg atc aag    215
Ala Met Gln Lys Ile Leu Glu Cys Pro Ile Cys Leu Glu Leu Ile Lys
                20                  25                  30 gaa cct gtc tcc aca aag tgt gac cac ata ttt tgc aaa ttt tgc atg    263
Glu Pro Val Ser Thr Lys Cys Asp His Ile Phe Cys Lys Phe Cys Met
            35                  40                  45 ctg aaa ctt ctc aac cag aag aaa ggg cct tca cag tgt cct tta tgt    311
Leu Lys Leu Leu Asn Gln Lys Lys Gly Pro Ser Gln Cys Pro Leu Cys
        50                  55                  60 aag aat gat ata acc aaa agg agc cta caa gaa agt acg aga ttt agt    359
Lys Asn Asp Ile Thr Lys Arg Ser Leu Gln Glu Ser Thr Arg Phe Ser
65                  70                  75                  80 caa ctt gtt gaa gag cta ttg aaa atc att tgt gct ttt cag ctt gac    407
Gln Leu Val Glu Glu Leu Leu Lys Ile Ile Cys Ala Phe Gln Leu Asp
                85                  90                  95 aca ggt ttg gag tat gca aac agc tat aat ttt gca aaa aag gaa aat    455
Thr Gly Leu Glu Tyr Ala Asn Ser Tyr Asn Phe Ala Lys Lys Glu Asn
                100                 105                 110 aac tct cct gaa cat cta aaa gat gaa gtt tct atc atc caa agt atg    503
Asn Ser Pro Glu His Leu Lys Asp Glu Val Ser Ile Ile Gln Ser Met
            115                 120                 125 ggc tac aga aac cgt gcc aaa aga ctt cta cag agt gaa ccc gaa aat    551
Gly Tyr Arg Asn Arg Ala Lys Arg Leu Leu Gln Ser Glu Pro Glu Asn
        130                 135                 140 cct tcc ttg cag gaa acc agt ctc agt gtc caa ctc tct aac ctt gga    599
Pro Ser Leu Gln Glu Thr Ser Leu Ser Val Gln Leu Ser Asn Leu Gly
145                 150                 155                 160 act gtg aga act ctg agg aca aag cag cgg ata caa cct caa aag acg    647
Thr Val Arg Thr Leu Arg Thr Lys Gln Arg Ile Gln Pro Gln Lys Thr
                165                 170                 175 tct gtc tac att gaa ttg gga tct gat tct tct gaa gat acc gtt aat    695
Ser Val Tyr Ile Glu Leu Gly Ser Asp Ser Ser Glu Asp Thr Val Asn
                180                 185                 190 aag gca act tat tgc agt gtg gga gat caa gaa ttg tta caa atc acc    743
Lys Ala Thr Tyr Cys Ser Val Gly Asp Gln Glu Leu Leu Gln Ile Thr
            195                 200                 205 cct caa gga acc agg gat gaa atc agt ttg gat tct gca aaa aag gct    791
Pro Gln Gly Thr Arg Asp Glu Ile Ser Leu Asp Ser Ala Lys Lys Ala
        210                 215                 220 gct tgt gaa ttt tct gag acg gat gta aca aat act gaa cat cat caa    839
Ala Cys Glu Phe Ser Glu Thr Asp Val Thr Asn Thr Glu His His Gln
225                 230                 235                 240
```

-continued

```
ccc agt aat aat gat ttg aac acc act gag aag cgt gca gct gag agg         887
Pro Ser Asn Asn Asp Leu Asn Thr Thr Glu Lys Arg Ala Ala Glu Arg
            245                 250                 255 cat cca gaa aag tat cag ggt agt tct gtt tca aac ttg cat gtg gag         935
His Pro Glu Lys Tyr Gln Gly Ser Ser Val Ser Asn Leu His Val Glu
            260                 265                 270 cca tgt ggc aca aat act cat gcc agc tca tta cag cat gag aac agc         983
Pro Cys Gly Thr Asn Thr His Ala Ser Ser Leu Gln His Glu Asn Ser
            275                 280                 285 agt tta tta ctc act aaa gac aga atg aat gta gaa aag gct gaa ttc        1031
Ser Leu Leu Leu Thr Lys Asp Arg Met Asn Val Glu Lys Ala Glu Phe
            290                 295                 300 tgt aat aaa agc aaa cag cct ggc tta gca agg agc caa cat aac aga        1079
Cys Asn Lys Ser Lys Gln Pro Gly Leu Ala Arg Ser Gln His Asn Arg
305                 310                 315                 320 tgg gct gga agt aag gaa aca tgt aat gat agg cgg act ccc agc aca        1127
Trp Ala Gly Ser Lys Glu Thr Cys Asn Asp Arg Arg Thr Pro Ser Thr
            325                 330                 335 gaa aaa aag gta gat ctg aat gct gat ccc ctg tgt gag aga aaa gaa        1175
Glu Lys Lys Val Asp Leu Asn Ala Asp Pro Leu Cys Glu Arg Lys Glu
            340                 345                 350 tgg aat aag cag aaa ctg cca tgc tca gag aat cct aga gat act gaa        1223
Trp Asn Lys Gln Lys Leu Pro Cys Ser Glu Asn Pro Arg Asp Thr Glu
            355                 360                 365 gat gtt cct tgg ata aca cta aat agc agc att cag aaa gtt aat gag        1271
Asp Val Pro Trp Ile Thr Leu Asn Ser Ser Ile Gln Lys Val Asn Glu
            370                 375                 380 tgg ttt tcc aga agt gat gaa ctg tta ggt tct gat gac tca cat gat        1319
Trp Phe Ser Arg Ser Asp Glu Leu Leu Gly Ser Asp Asp Ser His Asp
385                 390                 395                 400 ggg gag tct gaa tca aat gcc aaa gta gct gat gta ttg gac gtt cta        1367
Gly Glu Ser Glu Ser Asn Ala Lys Val Ala Asp Val Leu Asp Val Leu
            405                 410                 415 aat gag gta gat gaa tat tct ggt tct tca gag aaa ata gac tta ctg        1415
Asn Glu Val Asp Glu Tyr Ser Gly Ser Ser Glu Lys Ile Asp Leu Leu
            420                 425                 430 gcc agt gat cct cat gag gct tta ata tgt aaa agt gaa aga gtt cac        1463
Ala Ser Asp Pro His Glu Ala Leu Ile Cys Lys Ser Glu Arg Val His
            435                 440                 445 tcc aaa tca gta gag agt aat att gaa gac aaa ata ttt ggg aaa acc        1511
Ser Lys Ser Val Glu Ser Asn Ile Glu Asp Lys Ile Phe Gly Lys Thr
            450                 455                 460 tat cgg aag aag gca agc ctc ccc aac tta agc cat gta act gaa aat        1559
Tyr Arg Lys Lys Ala Ser Leu Pro Asn Leu Ser His Val Thr Glu Asn
465                 470                 475                 480 cta att ata gga gca ttt gtt act gag cca cag ata ata caa gag cgt        1607
Leu Ile Ile Gly Ala Phe Val Thr Glu Pro Gln Ile Ile Gln Glu Arg
            485                 490                 495 ccc ctc aca aat aaa tta aag cgt aaa agg aga cct aca tca ggc ctt        1655
Pro Leu Thr Asn Lys Leu Lys Arg Lys Arg Arg Pro Thr Ser Gly Leu
            500                 505                 510 cat cct gag gat ttt atc aag aaa gca gat ttg gca gtt caa aag act        1703
His Pro Glu Asp Phe Ile Lys Lys Ala Asp Leu Ala Val Gln Lys Thr
            515                 520                 525 cct gaa atg ata aat cag gga act aac caa acg gag cag aat ggt caa        1751
Pro Glu Met Ile Asn Gln Gly Thr Asn Gln Thr Glu Gln Asn Gly Gln
            530                 535                 540 gtg atg aat att act aat agt ggt cat gag aat aaa aca aaa ggt gat        1799
Val Met Asn Ile Thr Asn Ser Gly His Glu Asn Lys Thr Lys Gly Asp
545                 550                 555                 560
```

| | |
|---|---|
| tct att cag aat gag aaa aat cct aac cca ata gaa tca ctc gaa aaa<br>Ser Ile Gln Asn Glu Lys Asn Pro Asn Pro Ile Glu Ser Leu Glu Lys<br>565 570 575 | 1847 |
| gaa tct gct ttc aaa acg aaa gct gaa cct ata agc agc agt ata agc<br>Glu Ser Ala Phe Lys Thr Lys Ala Glu Pro Ile Ser Ser Ser Ile Ser<br>580 585 590 | 1895 |
| aat atg gaa ctc gaa tta aat atc cac aat tca aaa gca cct aaa aag<br>Asn Met Glu Leu Glu Leu Asn Ile His Asn Ser Lys Ala Pro Lys Lys<br>595 600 605 | 1943 |
| aat agg ctg agg agg aag tct tct acc agg cat att cat gcg ctt gaa<br>Asn Arg Leu Arg Arg Lys Ser Ser Thr Arg His Ile His Ala Leu Glu<br>610 615 620 | 1991 |
| cta gta gtc agt aga aat cta agc cca cct aat tgt act gaa ttg caa<br>Leu Val Val Ser Arg Asn Leu Ser Pro Pro Asn Cys Thr Glu Leu Gln<br>625 630 635 640 | 2039 |
| att gat agt tgt tct agc agt gaa gag ata aag aaa aaa aag tac aac<br>Ile Asp Ser Cys Ser Ser Ser Glu Glu Ile Lys Lys Lys Lys Tyr Asn<br>645 650 655 | 2087 |
| caa atg cca gtc agg cac agc aga aac cta caa ctc atg gaa ggt aaa<br>Gln Met Pro Val Arg His Ser Arg Asn Leu Gln Leu Met Glu Gly Lys<br>660 665 670 | 2135 |
| gaa cct gca act gga gcc aag aag agt aac aag cca aat gaa cag aca<br>Glu Pro Ala Thr Gly Ala Lys Lys Ser Asn Lys Pro Asn Glu Gln Thr<br>675 680 685 | 2183 |
| agt aaa aga cat gac agt gat act ttc cca gag ctg aag tta aca aat<br>Ser Lys Arg His Asp Ser Asp Thr Phe Pro Glu Leu Lys Leu Thr Asn<br>690 695 700 | 2231 |
| gca cct ggt tct ttt act aag tgt tca aat acc agt gaa ctt aaa gaa<br>Ala Pro Gly Ser Phe Thr Lys Cys Ser Asn Thr Ser Glu Leu Lys Glu<br>705 710 715 720 | 2279 |
| ttt gtc aat cct agc ctt cca aga gaa gaa aaa gaa gag aaa cta gaa<br>Phe Val Asn Pro Ser Leu Pro Arg Glu Glu Lys Glu Glu Lys Leu Glu<br>725 730 735 | 2327 |
| aca gtt aaa gtg tct aat aat gct gaa gac ccc aaa gat ctc atg tta<br>Thr Val Lys Val Ser Asn Asn Ala Glu Asp Pro Lys Asp Leu Met Leu<br>740 745 750 | 2375 |
| agt gga gaa agg gtt ttg caa act gaa aga tct gta gag agt agc agt<br>Ser Gly Glu Arg Val Leu Gln Thr Glu Arg Ser Val Glu Ser Ser Ser<br>755 760 765 | 2423 |
| att tca ctg gta cct ggt act gat tat ggc act cag gaa agt atc tcg<br>Ile Ser Leu Val Pro Gly Thr Asp Tyr Gly Thr Gln Glu Ser Ile Ser<br>770 775 780 | 2471 |
| tta ctg gaa gtt agc act cta ggg aag gca aaa aca gaa cca aat aaa<br>Leu Leu Glu Val Ser Thr Leu Gly Lys Ala Lys Thr Glu Pro Asn Lys<br>785 790 795 800 | 2519 |
| tgt gtg agt cag tgt gca gca ttt gaa aac ccc aag gga cta att cat<br>Cys Val Ser Gln Cys Ala Ala Phe Glu Asn Pro Lys Gly Leu Ile His<br>805 810 815 | 2567 |
| ggt tgt tcc aaa gat aat aga aat gac aca gaa ggc ttt aag tat cca<br>Gly Cys Ser Lys Asp Asn Arg Asn Asp Thr Glu Gly Phe Lys Tyr Pro<br>820 825 830 | 2615 |
| ttg gga cat gaa gtt aac cac agt cgg gaa aca agc ata gaa atg gaa<br>Leu Gly His Glu Val Asn His Ser Arg Glu Thr Ser Ile Glu Met Glu<br>835 840 845 | 2663 |
| gaa agt gaa ctt gat gct cag tat ttg cag aat aca ttc aag gtt tca<br>Glu Ser Glu Leu Asp Ala Gln Tyr Leu Gln Asn Thr Phe Lys Val Ser<br>850 855 860 | 2711 |
| aag cgc cag tca ttt gct ctg ttt tca aat cca gga aat gca gaa gag<br>Lys Arg Gln Ser Phe Ala Leu Phe Ser Asn Pro Gly Asn Ala Glu Glu | 2759 |

-continued

```
            865                 870                 875                 880 gaa tgt gca aca ttc tct gcc cac tct ggg tcc tta aag aaa caa agt        2807
Glu Cys Ala Thr Phe Ser Ala His Ser Gly Ser Leu Lys Lys Gln Ser
                        885                 890                 895 cca aaa gtc act ttt gaa tgt gaa caa aag gaa gaa aat caa gga aag        2855
Pro Lys Val Thr Phe Glu Cys Glu Gln Lys Glu Glu Asn Gln Gly Lys
                900                 905                 910 aat gag tct aat atc aag cct gta cag aca gtt aat atc act gca ggc        2903
Asn Glu Ser Asn Ile Lys Pro Val Gln Thr Val Asn Ile Thr Ala Gly
            915                 920                 925 ttt cct gtg gtt ggt cag aaa gat aag cca gtt gat aat gcc aaa tgt        2951
Phe Pro Val Val Gly Gln Lys Asp Lys Pro Val Asp Asn Ala Lys Cys
        930                 935                 940 agt atc aaa gga ggc tct agg ttt tgt cta tca tct cag ttc aga ggc        2999
Ser Ile Lys Gly Gly Ser Arg Phe Cys Leu Ser Ser Gln Phe Arg Gly
945                 950                 955                 960 aac gaa act gga ctc att act cca aat aaa cat gga ctt tta caa aac        3047
Asn Glu Thr Gly Leu Ile Thr Pro Asn Lys His Gly Leu Leu Gln Asn
                965                 970                 975 cca tat cgt ata cca cca ctt ttt ccc atc aag tca ttt gtt aaa act        3095
Pro Tyr Arg Ile Pro Pro Leu Phe Pro Ile Lys Ser Phe Val Lys Thr
            980                 985                 990 aaa tgt aag aaa aat ctg cta gag  gaa aac ttt gag gaa  cat tca atg     3143
Lys Cys Lys Lys Asn Leu Leu Glu  Glu Asn Phe Glu Glu  His Ser Met
            995                 1000                1005 tca cct  gaa aga gaa atg gga  aat gag aac att cca  agt aca gtg         3188
Ser Pro  Glu Arg Glu Met Gly  Asn Glu Asn Ile Pro  Ser Thr Val
    1010                1015                1020 agc aca att agc cgt aat aac  att aga gaa aat gtt  ttt aaa gga          3233
Ser Thr Ile Ser Arg Asn Asn  Ile Arg Glu Asn Val  Phe Lys Gly
    1025                1030                1035 gcc agc tca agc aat att aat  gaa gta ggt tcc agt  act aat gaa          3278
Ala Ser Ser Ser Asn Ile Asn  Glu Val Gly Ser Ser  Thr Asn Glu
    1040                1045                1050 gtg ggc tcc agt att aat gaa  ata ggt tcc agt gat  gaa aac att          3323
Val Gly Ser Ser Ile Asn Glu  Ile Gly Ser Ser Asp  Glu Asn Ile
    1055                1060                1065 caa gca gaa cta ggt aga aac  aga ggg cca aaa ttg  aat gct atg          3368
Gln Ala Glu Leu Gly Arg Asn  Arg Gly Pro Lys Leu  Asn Ala Met
    1070                1075                1080 ctt aga tta ggg gtt ttg caa  cct gag gtc tat aaa  caa agt ctt          3413
Leu Arg Leu Gly Val Leu Gln  Pro Glu Val Tyr Lys  Gln Ser Leu
    1085                1090                1095 cct gga agt aat tgt aag cat  cct gaa ata aaa aag  caa gaa tat          3458
Pro Gly Ser Asn Cys Lys His  Pro Glu Ile Lys Lys  Gln Glu Tyr
    1100                1105                1110 gaa gaa gta gtt cag act gtt  aat aca gat ttc tct  cca tat ctg          3503
Glu Glu Val Val Gln Thr Val  Asn Thr Asp Phe Ser  Pro Tyr Leu
    1115                1120                1125 att tca gat aac tta gaa cag  cct atg gga agt agt  cat gca tct          3548
Ile Ser Asp Asn Leu Glu Gln  Pro Met Gly Ser Ser  His Ala Ser
    1130                1135                1140 cag gtt tgt tct gag aca cct  gat gac ctg tta gat  gat ggt gaa          3593
Gln Val Cys Ser Glu Thr Pro  Asp Asp Leu Leu Asp  Asp Gly Glu
    1145                1150                1155 ata aag gaa gat act agt ttt  gct gaa aat gac att  aag gaa agt          3638
Ile Lys Glu Asp Thr Ser Phe  Ala Glu Asn Asp Ile  Lys Glu Ser
    1160                1165                1170 tct gct gtt ttt agc aaa agc  gtc cag aga gga gag  ctt agc agg          3683
```

```
Ser Ala Val Phe Ser Lys Ser Val Gln Arg Gly Glu Leu Ser Arg
1175              1180              1185 agt cct agc cct ttc acc cat aca cat ttg gct cag ggt tac cga       3728
Ser Pro Ser Pro Phe Thr His Thr His Leu Ala Gln Gly Tyr Arg
1190              1195              1200 aga ggg gcc aag aaa tta gag tcc tca gaa gag aac tta tct agt       3773
Arg Gly Ala Lys Lys Leu Glu Ser Ser Glu Glu Asn Leu Ser Ser
1205              1210              1215 gag gat gaa gag ctt ccc tgc ttc caa cac ttg tta ttt ggt aaa       3818
Glu Asp Glu Glu Leu Pro Cys Phe Gln His Leu Leu Phe Gly Lys
1220              1225              1230 gta aac aat ata cct tct cag tct act agg cat agc acc gtt gct       3863
Val Asn Asn Ile Pro Ser Gln Ser Thr Arg His Ser Thr Val Ala
1235              1240              1245 acc gag tgt ctg tct aag aac aca gag gag aat tta tta tca ttg       3908
Thr Glu Cys Leu Ser Lys Asn Thr Glu Glu Asn Leu Leu Ser Leu
1250              1255              1260 aag aat agc tta aat gac tgc agt aac cag gta ata ttg gca aag       3953
Lys Asn Ser Leu Asn Asp Cys Ser Asn Gln Val Ile Leu Ala Lys
1265              1270              1275 gca tct cag gaa cat cac ctt agt gag gaa aca aaa tgt tct gct       3998
Ala Ser Gln Glu His His Leu Ser Glu Glu Thr Lys Cys Ser Ala
1280              1285              1290 agc ttg ttt tct tca cag tgc agt gaa ttg gaa gac ttg act gca       4043
Ser Leu Phe Ser Ser Gln Cys Ser Glu Leu Glu Asp Leu Thr Ala
1295              1300              1305 aat aca aac acc cag gat cct ttc ttg att ggt tct tcc aaa caa       4088
Asn Thr Asn Thr Gln Asp Pro Phe Leu Ile Gly Ser Ser Lys Gln
1310              1315              1320 atg agg cat cag tct gaa agc cag gga gtt ggt ctg agt gac aag       4133
Met Arg His Gln Ser Glu Ser Gln Gly Val Gly Leu Ser Asp Lys
1325              1330              1335 gaa ttg gtt tca gat gat gaa gaa aga gga acg ggc ttg gaa gaa       4178
Glu Leu Val Ser Asp Asp Glu Glu Arg Gly Thr Gly Leu Glu Glu
1340              1345              1350 aat aat caa gaa gag caa agc atg gat tca aac tta ggt gaa gca       4223
Asn Asn Gln Glu Glu Gln Ser Met Asp Ser Asn Leu Gly Glu Ala
1355              1360              1365 gca tct ggg tgt gag agt gaa aca agc gtc tct gaa gac tgc tca       4268
Ala Ser Gly Cys Glu Ser Glu Thr Ser Val Ser Glu Asp Cys Ser
1370              1375              1380 ggg cta tcc tct cag agt gac att tta acc act cag cag agg gat       4313
Gly Leu Ser Ser Gln Ser Asp Ile Leu Thr Thr Gln Gln Arg Asp
1385              1390              1395 acc atg caa cat aac ctg ata aag ctc cag cag gaa atg gct gaa       4358
Thr Met Gln His Asn Leu Ile Lys Leu Gln Gln Glu Met Ala Glu
1400              1405              1410 cta gaa gct gtg tta gaa cag cat ggg agc cag cct tct aac agc       4403
Leu Glu Ala Val Leu Glu Gln His Gly Ser Gln Pro Ser Asn Ser
1415              1420              1425 tac cct tcc atc ata agt gac tcc tct gcc ctt gag gac ctg cga       4448
Tyr Pro Ser Ile Ile Ser Asp Ser Ser Ala Leu Glu Asp Leu Arg
1430              1435              1440 aat cca gaa caa agc aca tca gaa aaa gca gta tta act tca cag       4493
Asn Pro Glu Gln Ser Thr Ser Glu Lys Ala Val Leu Thr Ser Gln
1445              1450              1455 aaa agt agt gaa tac cct ata agc cag aat cca gaa ggc ctt tct       4538
Lys Ser Ser Glu Tyr Pro Ile Ser Gln Asn Pro Glu Gly Leu Ser
1460              1465              1470
```

```
                                          -continued gct gac aag ttt gag gtg tct gca gat agt tcc acc agt aaa aat      4583
Ala Asp Lys Phe Glu Val Ser Ala Asp Ser Ser Thr Ser Lys Asn
1475                1480                1485 aaa gaa cca gga gtg gaa agg tca tcc cct tct aaa tgc cca tca      4628
Lys Glu Pro Gly Val Glu Arg Ser Ser Pro Ser Lys Cys Pro Ser
    1490                1495                1500 tta gat gat agg tgg tac atg cac agt tgc tct ggg agt ctt cag      4673
Leu Asp Asp Arg Trp Tyr Met His Ser Cys Ser Gly Ser Leu Gln
1505                1510                1515 aat aga aac tac cca tct caa gag gag ctc att aag gtt gtt gat      4718
Asn Arg Asn Tyr Pro Ser Gln Glu Glu Leu Ile Lys Val Val Asp
    1520                1525                1530 gtg gag gag caa cag ctg gaa gag tct ggg cca cac gat ttg acg      4763
Val Glu Glu Gln Gln Leu Glu Glu Ser Gly Pro His Asp Leu Thr
1535                1540                1545 gaa aca tct tac ttg cca agg caa gat cta gag gga acc cct tac      4808
Glu Thr Ser Tyr Leu Pro Arg Gln Asp Leu Glu Gly Thr Pro Tyr
    1550                1555                1560 ctg gaa tct gga atc agc ctc ttc tct gat gac cct gaa tct gat      4853
Leu Glu Ser Gly Ile Ser Leu Phe Ser Asp Asp Pro Glu Ser Asp
1565                1570                1575 cct tct gaa gac aga gcc cca gag tca gct cgt gtt ggc aac ata      4898
Pro Ser Glu Asp Arg Ala Pro Glu Ser Ala Arg Val Gly Asn Ile
    1580                1585                1590 cca tct tca acc tct gca ttg aaa gtt ccc caa ttg aaa gtt gca      4943
Pro Ser Ser Thr Ser Ala Leu Lys Val Pro Gln Leu Lys Val Ala
1595                1600                1605 gaa tct gcc cag ggt cca gct gct gct cat act act gat act gct      4988
Glu Ser Ala Gln Gly Pro Ala Ala Ala His Thr Thr Asp Thr Ala
    1610                1615                1620 ggg tat aat gca atg gaa gaa agt gtg agc agg gag aag cca gaa      5033
Gly Tyr Asn Ala Met Glu Glu Ser Val Ser Arg Glu Lys Pro Glu
1625                1630                1635 ttg aca gct tca aca gaa agg gtc aac aaa aga atg tcc atg gtg      5078
Leu Thr Ala Ser Thr Glu Arg Val Asn Lys Arg Met Ser Met Val
    1640                1645                1650 gtg tct ggc ctg acc cca gaa gaa ttt atg ctc gtg tac aag ttt      5123
Val Ser Gly Leu Thr Pro Glu Glu Phe Met Leu Val Tyr Lys Phe
1655                1660                1665 gcc aga aaa cac cac atc act tta act aat cta att act gaa gag      5168
Ala Arg Lys His His Ile Thr Leu Thr Asn Leu Ile Thr Glu Glu
    1670                1675                1680 act act cat gtt gtt atg aaa aca gat gct gag ttt gtg tgt gaa      5213
Thr Thr His Val Val Met Lys Thr Asp Ala Glu Phe Val Cys Glu
1685                1690                1695 cgg aca ctg aaa tat ttt cta gga att gcg gga gga aaa tgg gta      5258
Arg Thr Leu Lys Tyr Phe Leu Gly Ile Ala Gly Gly Lys Trp Val
    1700                1705                1710 gtt agc tat ttc tgg gtg acc cag tct att aaa gaa aga aaa atg      5303
Val Ser Tyr Phe Trp Val Thr Gln Ser Ile Lys Glu Arg Lys Met
1715                1720                1725 ctg aat gag cat gat ttt gaa gtc aga gga gat gtg gtc aat gga      5348
Leu Asn Glu His Asp Phe Glu Val Arg Gly Asp Val Val Asn Gly
    1730                1735                1740 aga aac cac caa ggt cca aag cga gca aga gaa tcc cag gac aga      5393
Arg Asn His Gln Gly Pro Lys Arg Ala Arg Glu Ser Gln Asp Arg
1745                1750                1755 aag atc ttc agg ggg cta gaa atc tgt tgc tat ggg ccc ttc acc      5438
Lys Ile Phe Arg Gly Leu Glu Ile Cys Cys Tyr Gly Pro Phe Thr
    1760                1765                1770
```

```
aac atg ccc aca gat caa ctg gaa tgg atg gta cag ctg tgt ggt      5483
Asn Met Pro Thr Asp Gln Leu Glu Trp Met Val Gln Leu Cys Gly
    1775                1780                1785 gct tct gtg gtg aag gag ctt tca tca ttc acc ctt ggc aca ggt      5528
Ala Ser Val Val Lys Glu Leu Ser Ser Phe Thr Leu Gly Thr Gly
    1790                1795                1800 gtc cac cca att gtg gtt gtg cag cca gat gcc tgg aca gag gac      5573
Val His Pro Ile Val Val Val Gln Pro Asp Ala Trp Thr Glu Asp
    1805                1810                1815 aat ggc ttc cat gca att ggg cag atg tgt gag gca cct gtg gtg      5618
Asn Gly Phe His Ala Ile Gly Gln Met Cys Glu Ala Pro Val Val
    1820                1825                1830 acc cga gag tgg gtg ttg gac agt gta gca ctc tac cag tgc cag      5663
Thr Arg Glu Trp Val Leu Asp Ser Val Ala Leu Tyr Gln Cys Gln
    1835                1840                1845 gag ctg gac acc tac ctg ata ccc cag atc ccc cac agc cac tac      5708
Glu Leu Asp Thr Tyr Leu Ile Pro Gln Ile Pro His Ser His Tyr
    1850                1855                1860 tga                                                              5711
```

<210> SEQ ID NO 264
<211> LENGTH: 1863
<212> TYPE: PRT
<213> ORGANISM: Homo sapiens

<400> SEQUENCE: 264

```
Met Asp Leu Ser Ala Leu Arg Val Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240
```

```
Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
            290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
                340                 345                 350

Trp Asn Lys Gln Lys Leu Pro Cys Ser Glu Asn Pro Arg Asp Thr Glu
                355                 360                 365

Asp Val Pro Trp Ile Thr Leu Asn Ser Ser Ile Gln Lys Val Asn Glu
        370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
                500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
            610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655
```

-continued

```
Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
            690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
            805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
            850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
            885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
            930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
            965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val
            1010                1015                1020

Ser Thr Ile Ser Arg Asn Asn Ile Arg Glu Asn Val Phe Lys Gly
            1025                1030                1035

Ala Ser Ser Ser Asn Ile Asn Glu Val Gly Ser Ser Thr Asn Glu
            1040                1045                1050

Val Gly Ser Ser Ile Asn Glu Ile Gly Ser Ser Asp Glu Asn Ile
            1055                1060                1065

Gln Ala Glu Leu Gly Arg Asn Arg Gly Pro Lys Leu Asn Ala Met
```

-continued

```
              1070                1075                1080
Leu Arg Leu Gly Val Leu Gln Pro Glu Val Tyr Lys Gln Ser Leu
    1085                1090                1095
Pro Gly Ser Asn Cys Lys His Pro Glu Ile Lys Lys Gln Glu Tyr
    1100                1105                1110
Glu Glu Val Val Gln Thr Val Asn Thr Asp Phe Ser Pro Tyr Leu
    1115                1120                1125
Ile Ser Asp Asn Leu Glu Gln Pro Met Gly Ser Ser His Ala Ser
    1130                1135                1140
Gln Val Cys Ser Glu Thr Pro Asp Asp Leu Leu Asp Asp Gly Glu
    1145                1150                1155
Ile Lys Glu Asp Thr Ser Phe Ala Glu Asn Asp Ile Lys Glu Ser
    1160                1165                1170
Ser Ala Val Phe Ser Lys Ser Val Gln Arg Gly Glu Leu Ser Arg
    1175                1180                1185
Ser Pro Ser Pro Phe Thr His Thr His Leu Ala Gln Gly Tyr Arg
    1190                1195                1200
Arg Gly Ala Lys Lys Leu Glu Ser Ser Glu Glu Asn Leu Ser Ser
    1205                1210                1215
Glu Asp Glu Glu Leu Pro Cys Phe Gln His Leu Leu Phe Gly Lys
    1220                1225                1230
Val Asn Asn Ile Pro Ser Gln Ser Thr Arg His Ser Thr Val Ala
    1235                1240                1245
Thr Glu Cys Leu Ser Lys Asn Thr Glu Glu Asn Leu Leu Ser Leu
    1250                1255                1260
Lys Asn Ser Leu Asn Asp Cys Ser Asn Gln Val Ile Leu Ala Lys
    1265                1270                1275
Ala Ser Gln Glu His His Leu Ser Glu Glu Thr Lys Cys Ser Ala
    1280                1285                1290
Ser Leu Phe Ser Ser Gln Cys Ser Glu Leu Glu Asp Leu Thr Ala
    1295                1300                1305
Asn Thr Asn Thr Gln Asp Pro Phe Leu Ile Gly Ser Ser Lys Gln
    1310                1315                1320
Met Arg His Gln Ser Glu Ser Gln Gly Val Gly Leu Ser Asp Lys
    1325                1330                1335
Glu Leu Val Ser Asp Asp Glu Glu Arg Gly Thr Gly Leu Glu Glu
    1340                1345                1350
Asn Asn Gln Glu Glu Gln Ser Met Asp Ser Asn Leu Gly Glu Ala
    1355                1360                1365
Ala Ser Gly Cys Glu Ser Glu Thr Ser Val Ser Glu Asp Cys Ser
    1370                1375                1380
Gly Leu Ser Ser Gln Ser Asp Ile Leu Thr Thr Gln Gln Arg Asp
    1385                1390                1395
Thr Met Gln His Asn Leu Ile Lys Leu Gln Gln Glu Met Ala Glu
    1400                1405                1410
Leu Glu Ala Val Leu Glu Gln His Gly Ser Gln Pro Ser Asn Ser
    1415                1420                1425
Tyr Pro Ser Ile Ile Ser Asp Ser Ser Ala Leu Glu Asp Leu Arg
    1430                1435                1440
Asn Pro Glu Gln Ser Thr Ser Glu Lys Ala Val Leu Thr Ser Gln
    1445                1450                1455
Lys Ser Ser Glu Tyr Pro Ile Ser Gln Asn Pro Glu Gly Leu Ser
    1460                1465                1470
```

```
Ala Asp Lys Phe Glu Val Ser Ala Asp Ser Ser Thr Ser Lys Asn
    1475            1480                1485

Lys Glu Pro Gly Val Glu Arg Ser Ser Pro Ser Lys Cys Pro Ser
    1490            1495                1500

Leu Asp Asp Arg Trp Tyr Met His Ser Cys Ser Gly Ser Leu Gln
    1505            1510                1515

Asn Arg Asn Tyr Pro Ser Gln Glu Glu Leu Ile Lys Val Val Asp
    1520            1525                1530

Val Glu Glu Gln Gln Leu Glu Glu Ser Gly Pro His Asp Leu Thr
    1535            1540                1545

Glu Thr Ser Tyr Leu Pro Arg Gln Asp Leu Glu Gly Thr Pro Tyr
    1550            1555                1560

Leu Glu Ser Gly Ile Ser Leu Phe Ser Asp Asp Pro Glu Ser Asp
    1565            1570                1575

Pro Ser Glu Asp Arg Ala Pro Glu Ser Ala Arg Val Gly Asn Ile
    1580            1585                1590

Pro Ser Ser Thr Ser Ala Leu Lys Val Pro Gln Leu Lys Val Ala
    1595            1600                1605

Glu Ser Ala Gln Gly Pro Ala Ala Ala His Thr Thr Asp Thr Ala
    1610            1615                1620

Gly Tyr Asn Ala Met Glu Glu Ser Val Ser Arg Glu Lys Pro Glu
    1625            1630                1635

Leu Thr Ala Ser Thr Glu Arg Val Asn Lys Arg Met Ser Met Val
    1640            1645                1650

Val Ser Gly Leu Thr Pro Glu Glu Phe Met Leu Val Tyr Lys Phe
    1655            1660                1665

Ala Arg Lys His His Ile Thr Leu Thr Asn Leu Ile Thr Glu Glu
    1670            1675                1680

Thr Thr His Val Val Met Lys Thr Asp Ala Glu Phe Val Cys Glu
    1685            1690                1695

Arg Thr Leu Lys Tyr Phe Leu Gly Ile Ala Gly Gly Lys Trp Val
    1700            1705                1710

Val Ser Tyr Phe Trp Val Thr Gln Ser Ile Lys Glu Arg Lys Met
    1715            1720                1725

Leu Asn Glu His Asp Phe Glu Val Arg Gly Asp Val Val Asn Gly
    1730            1735                1740

Arg Asn His Gln Gly Pro Lys Arg Ala Arg Glu Ser Gln Asp Arg
    1745            1750                1755

Lys Ile Phe Arg Gly Leu Glu Ile Cys Cys Tyr Gly Pro Phe Thr
    1760            1765                1770

Asn Met Pro Thr Asp Gln Leu Glu Trp Met Val Gln Leu Cys Gly
    1775            1780                1785

Ala Ser Val Val Lys Glu Leu Ser Ser Phe Thr Leu Gly Thr Gly
    1790            1795                1800

Val His Pro Ile Val Val Val Gln Pro Asp Ala Trp Thr Glu Asp
    1805            1810                1815

Asn Gly Phe His Ala Ile Gly Gln Met Cys Glu Ala Pro Val Val
    1820            1825                1830

Thr Arg Glu Trp Val Leu Asp Ser Val Ala Leu Tyr Gln Cys Gln
    1835            1840                1845

Glu Leu Asp Thr Tyr Leu Ile Pro Gln Ile Pro His Ser His Tyr
    1850            1855                1860
```

```
<210> SEQ ID NO 265
<211> LENGTH: 5711
<212> TYPE: DNA
<213> ORGANISM: Homo sapiens
<220> FEATURE:
<221> NAME/KEY: CDS
<222> LOCATION: (120)..(5711)
<223> OTHER INFORMATION: omi2 sequences

<400> SEQUENCE: 265
```

| | | |
|---|---|---|
| agctcgctga gacttcctgg accccgcacc aggctgtggg gtttctcaga taactgggcc | | 60 |
| cctgcgctca ggaggccttc accctctgct ctgggtaaag ttcattggaa cagaaagaa | | 119 |
| atg gat tta tct gct ctt cgc gtt gaa gaa gta caa aat gtc att aat<br>Met Asp Leu Ser Ala Leu Arg Val Glu Glu Val Gln Asn Val Ile Asn<br>1               5                   10                  15 | | 167 |
| gct atg cag aaa atc tta gag tgt ccc atc tgt ctg gag ttg atc aag<br>Ala Met Gln Lys Ile Leu Glu Cys Pro Ile Cys Leu Glu Leu Ile Lys<br>            20                  25                  30 | | 215 |
| gaa cct gtc tcc aca aag tgt gac cac ata ttt tgc aaa ttt tgc atg<br>Glu Pro Val Ser Thr Lys Cys Asp His Ile Phe Cys Lys Phe Cys Met<br>        35                  40                  45 | | 263 |
| ctg aaa ctt ctc aac cag aag aaa ggg cct tca cag tgt cct tta tgt<br>Leu Lys Leu Leu Asn Gln Lys Lys Gly Pro Ser Gln Cys Pro Leu Cys<br>    50                  55                  60 | | 311 |
| aag aat gat ata acc aaa agg agc cta caa gaa agt acg aga ttt agt<br>Lys Asn Asp Ile Thr Lys Arg Ser Leu Gln Glu Ser Thr Arg Phe Ser<br>65                  70                  75                  80 | | 359 |
| caa ctt gtt gaa gag cta ttg aaa atc att tgt gct ttt cag ctt gac<br>Gln Leu Val Glu Glu Leu Leu Lys Ile Ile Cys Ala Phe Gln Leu Asp<br>                85                  90                  95 | | 407 |
| aca ggt ttg gag tat gca aac agc tat aat ttt gca aaa aag gaa aat<br>Thr Gly Leu Glu Tyr Ala Asn Ser Tyr Asn Phe Ala Lys Lys Glu Asn<br>            100                 105                 110 | | 455 |
| aac tct cct gaa cat cta aaa gat gaa gtt tct atc atc caa agt atg<br>Asn Ser Pro Glu His Leu Lys Asp Glu Val Ser Ile Ile Gln Ser Met<br>        115                 120                 125 | | 503 |
| ggc tac aga aac cgt gcc aaa aga ctt cta cag agt gaa ccc gaa aat<br>Gly Tyr Arg Asn Arg Ala Lys Arg Leu Leu Gln Ser Glu Pro Glu Asn<br>    130                 135                 140 | | 551 |
| cct tcc ttg cag gaa acc agt ctc agt gtc caa ctc tct aac ctt gga<br>Pro Ser Leu Gln Glu Thr Ser Leu Ser Val Gln Leu Ser Asn Leu Gly<br>145                 150                 155                 160 | | 599 |
| act gtg aga act ctg agg aca aag cag cgg ata caa cct caa aag acg<br>Thr Val Arg Thr Leu Arg Thr Lys Gln Arg Ile Gln Pro Gln Lys Thr<br>                165                 170                 175 | | 647 |
| tct gtc tac att gaa ttg gga tct gat tct tct gaa gat acc gtt aat<br>Ser Val Tyr Ile Glu Leu Gly Ser Asp Ser Ser Glu Asp Thr Val Asn<br>            180                 185                 190 | | 695 |
| aag gca act tat tgc agt gtg gga gat caa gaa ttg tta caa atc acc<br>Lys Ala Thr Tyr Cys Ser Val Gly Asp Gln Glu Leu Leu Gln Ile Thr<br>        195                 200                 205 | | 743 |
| cct caa gga acc agg gat gaa atc agt ttg gat tct gca aaa aag gct<br>Pro Gln Gly Thr Arg Asp Glu Ile Ser Leu Asp Ser Ala Lys Lys Ala<br>    210                 215                 220 | | 791 |
| gct tgt gaa ttt tct gag acg gat gta aca aat act gaa cat cat caa<br>Ala Cys Glu Phe Ser Glu Thr Asp Val Thr Asn Thr Glu His His Gln<br>225                 230                 235                 240 | | 839 |
| ccc agt aat aat gat ttg aac acc act gag aag cgt gca gct gag agg<br>Pro Ser Asn Asn Asp Leu Asn Thr Thr Glu Lys Arg Ala Ala Glu Arg<br>                245                 250                 255 | | 887 |

```
cat cca gaa aag tat cag ggt agt tct gtt tca aac ttg cat gtg gag       935
His Pro Glu Lys Tyr Gln Gly Ser Ser Val Ser Asn Leu His Val Glu
        260                 265                 270 cca tgt ggc aca aat act cat gcc agc tca tta cag cat gag aac agc       983
Pro Cys Gly Thr Asn Thr His Ala Ser Ser Leu Gln His Glu Asn Ser
        275                 280                 285 agt tta tta ctc act aaa gac aga atg aat gta gaa aag gct gaa ttc      1031
Ser Leu Leu Leu Thr Lys Asp Arg Met Asn Val Glu Lys Ala Glu Phe
        290                 295                 300 tgt aat aaa agc aaa cag cct ggc tta gca agg agc caa cat aac aga      1079
Cys Asn Lys Ser Lys Gln Pro Gly Leu Ala Arg Ser Gln His Asn Arg
305                 310                 315                 320 tgg gct gga agt aag gaa aca tgt aat gat agg cgg act ccc agc aca      1127
Trp Ala Gly Ser Lys Glu Thr Cys Asn Asp Arg Arg Thr Pro Ser Thr
                325                 330                 335 gaa aaa aag gta gat ctg aat gct gat ccc ctg tgt gag aga aaa gaa      1175
Glu Lys Lys Val Asp Leu Asn Ala Asp Pro Leu Cys Glu Arg Lys Glu
                340                 345                 350 tgg aat aag cag aaa ctg cca tgc tca gag aat cct aga gat act gaa      1223
Trp Asn Lys Gln Lys Leu Pro Cys Ser Glu Asn Pro Arg Asp Thr Glu
                355                 360                 365 gat gtt cct tgg ata aca cta aat agc agc att cag aaa gtt aat gag      1271
Asp Val Pro Trp Ile Thr Leu Asn Ser Ser Ile Gln Lys Val Asn Glu
370                 375                 380 tgg ttt tcc aga agt gat gaa ctg tta ggt tct gat gac tca cat gat      1319
Trp Phe Ser Arg Ser Asp Glu Leu Leu Gly Ser Asp Asp Ser His Asp
385                 390                 395                 400 ggg gag tct gaa tca aat gcc aaa gta gct gat gta ttg gac gtt cta      1367
Gly Glu Ser Glu Ser Asn Ala Lys Val Ala Asp Val Leu Asp Val Leu
                405                 410                 415 aat gag gta gat gaa tat tct ggt tct tca gag aaa ata gac tta ctg      1415
Asn Glu Val Asp Glu Tyr Ser Gly Ser Ser Glu Lys Ile Asp Leu Leu
                420                 425                 430 gcc agt gat cct cat gag gct tta ata tgt aaa agt gaa aga gtt cac      1463
Ala Ser Asp Pro His Glu Ala Leu Ile Cys Lys Ser Glu Arg Val His
                435                 440                 445 tcc aaa tca gta gag agt aat att gaa gac aaa ata ttt ggg aaa acc      1511
Ser Lys Ser Val Glu Ser Asn Ile Glu Asp Lys Ile Phe Gly Lys Thr
        450                 455                 460 tat cgg aag aag gca agc ctc ccc aac tta agc cat gta act gaa aat      1559
Tyr Arg Lys Lys Ala Ser Leu Pro Asn Leu Ser His Val Thr Glu Asn
465                 470                 475                 480 cta att ata gga gca ttt gtt act gag cca cag ata ata caa gag cgt      1607
Leu Ile Ile Gly Ala Phe Val Thr Glu Pro Gln Ile Ile Gln Glu Arg
                485                 490                 495 ccc ctc aca aat aaa tta aag cgt aaa agg aga cct aca tca ggc ctt      1655
Pro Leu Thr Asn Lys Leu Lys Arg Lys Arg Arg Pro Thr Ser Gly Leu
                500                 505                 510 cat cct gag gat ttt atc aag aaa gca gat ttg gca gtt caa aag act      1703
His Pro Glu Asp Phe Ile Lys Lys Ala Asp Leu Ala Val Gln Lys Thr
                515                 520                 525 cct gaa atg ata aat cag gga act aac caa acg gag cag aat ggt caa      1751
Pro Glu Met Ile Asn Gln Gly Thr Asn Gln Thr Glu Gln Asn Gly Gln
        530                 535                 540 gtg atg aat att act aat agt ggt cat gag aat aaa aca aaa ggt gat      1799
Val Met Asn Ile Thr Asn Ser Gly His Glu Asn Lys Thr Lys Gly Asp
545                 550                 555                 560 tct att cag aat gag aaa aat cct aac cca ata gaa tca ctc gaa aaa      1847
Ser Ile Gln Asn Glu Lys Asn Pro Asn Pro Ile Glu Ser Leu Glu Lys
```

|  |  |  |  |  |  | 565 |  |  |  |  |  | 570 |  |  |  |  |  | 575 |  |  |
|---|---|---|---|---|---|---|---|---|---|---|---|---|---|---|---|---|---|---|---|---|
| gaa | tct | gct | ttc | aaa | acg | aaa | gct | gaa | cct | ata | agc | agc | agt | ata | agc |  |  |  |  | 1895 |
| Glu | Ser | Ala | Phe | Lys | Thr | Lys | Ala | Glu | Pro | Ile | Ser | Ser | Ser | Ile | Ser |  |  |  |  |  |
|  |  |  | 580 |  |  |  |  | 585 |  |  |  |  |  | 590 |  |  |  |  |  |  |
| aat | atg | gaa | ctc | gaa | tta | aat | atc | cac | aat | tca | aaa | gca | cct | aaa | aag |  |  |  |  | 1943 |
| Asn | Met | Glu | Leu | Glu | Leu | Asn | Ile | His | Asn | Ser | Lys | Ala | Pro | Lys | Lys |  |  |  |  |  |
|  |  | 595 |  |  |  |  | 600 |  |  |  |  | 605 |  |  |  |  |  |  |  |  |
| aat | agg | ctg | agg | agg | aag | tct | tct | acc | agg | cat | att | cat | gcg | ctt | gaa |  |  |  |  | 1991 |
| Asn | Arg | Leu | Arg | Arg | Lys | Ser | Ser | Thr | Arg | His | Ile | His | Ala | Leu | Glu |  |  |  |  |  |
|  | 610 |  |  |  |  | 615 |  |  |  |  | 620 |  |  |  |  |  |  |  |  |  |
| cta | gta | gtc | agt | aga | aat | cta | agc | cca | cct | aat | tgt | act | gaa | ttg | caa |  |  |  |  | 2039 |
| Leu | Val | Val | Ser | Arg | Asn | Leu | Ser | Pro | Pro | Asn | Cys | Thr | Glu | Leu | Gln |  |  |  |  |  |
| 625 |  |  |  |  | 630 |  |  |  |  | 635 |  |  |  |  | 640 |  |  |  |  |  |
| att | gat | agt | tgt | tct | agc | agt | gaa | gag | ata | aag | aaa | aaa | aag | tac | aac |  |  |  |  | 2087 |
| Ile | Asp | Ser | Cys | Ser | Ser | Ser | Glu | Glu | Ile | Lys | Lys | Lys | Lys | Tyr | Asn |  |  |  |  |  |
|  |  |  |  | 645 |  |  |  |  | 650 |  |  |  |  | 655 |  |  |  |  |  |  |
| caa | atg | cca | gtc | agg | cac | agc | aga | aac | cta | caa | ctc | atg | gaa | ggt | aaa |  |  |  |  | 2135 |
| Gln | Met | Pro | Val | Arg | His | Ser | Arg | Asn | Leu | Gln | Leu | Met | Glu | Gly | Lys |  |  |  |  |  |
|  |  |  | 660 |  |  |  |  | 665 |  |  |  |  | 670 |  |  |  |  |  |  |  |
| gaa | cct | gca | act | gga | gcc | aag | aag | agt | aac | aag | cca | aat | gaa | cag | aca |  |  |  |  | 2183 |
| Glu | Pro | Ala | Thr | Gly | Ala | Lys | Lys | Ser | Asn | Lys | Pro | Asn | Glu | Gln | Thr |  |  |  |  |  |
|  |  | 675 |  |  |  |  | 680 |  |  |  |  | 685 |  |  |  |  |  |  |  |  |
| agt | aaa | aga | cat | gac | agt | gat | act | ttc | cca | gag | ctg | aag | tta | aca | aat |  |  |  |  | 2231 |
| Ser | Lys | Arg | His | Asp | Ser | Asp | Thr | Phe | Pro | Glu | Leu | Lys | Leu | Thr | Asn |  |  |  |  |  |
|  | 690 |  |  |  |  | 695 |  |  |  |  | 700 |  |  |  |  |  |  |  |  |  |
| gca | cct | ggt | tct | ttt | act | aag | tgt | tca | aat | acc | agt | gaa | ctt | aaa | gaa |  |  |  |  | 2279 |
| Ala | Pro | Gly | Ser | Phe | Thr | Lys | Cys | Ser | Asn | Thr | Ser | Glu | Leu | Lys | Glu |  |  |  |  |  |
| 705 |  |  |  | 710 |  |  |  |  | 715 |  |  |  |  | 720 |  |  |  |  |  |  |
| ttt | gtc | aat | cct | agc | ctt | cca | aga | gaa | gaa | aaa | gaa | gag | aaa | cta | gaa |  |  |  |  | 2327 |
| Phe | Val | Asn | Pro | Ser | Leu | Pro | Arg | Glu | Glu | Lys | Glu | Glu | Lys | Leu | Glu |  |  |  |  |  |
|  |  |  |  | 725 |  |  |  |  | 730 |  |  |  |  | 735 |  |  |  |  |  |  |
| aca | gtt | aaa | gtg | tct | aat | aat | gct | gaa | gac | ccc | aaa | gat | ctc | atg | tta |  |  |  |  | 2375 |
| Thr | Val | Lys | Val | Ser | Asn | Asn | Ala | Glu | Asp | Pro | Lys | Asp | Leu | Met | Leu |  |  |  |  |  |
|  |  |  | 740 |  |  |  |  | 745 |  |  |  |  | 750 |  |  |  |  |  |  |  |
| agt | gga | gaa | agg | gtt | ttg | caa | act | gaa | aga | tct | gta | gag | agt | agc | agt |  |  |  |  | 2423 |
| Ser | Gly | Glu | Arg | Val | Leu | Gln | Thr | Glu | Arg | Ser | Val | Glu | Ser | Ser | Ser |  |  |  |  |  |
|  |  | 755 |  |  |  |  | 760 |  |  |  |  | 765 |  |  |  |  |  |  |  |  |
| att | tca | ctg | gta | cct | ggt | act | gat | tat | ggc | act | cag | gaa | agt | atc | tcg |  |  |  |  | 2471 |
| Ile | Ser | Leu | Val | Pro | Gly | Thr | Asp | Tyr | Gly | Thr | Gln | Glu | Ser | Ile | Ser |  |  |  |  |  |
|  | 770 |  |  |  |  | 775 |  |  |  |  | 780 |  |  |  |  |  |  |  |  |  |
| tta | ctg | gaa | gtt | agc | act | cta | ggg | aag | gca | aaa | aca | gaa | cca | aat | aaa |  |  |  |  | 2519 |
| Leu | Leu | Glu | Val | Ser | Thr | Leu | Gly | Lys | Ala | Lys | Thr | Glu | Pro | Asn | Lys |  |  |  |  |  |
| 785 |  |  |  | 790 |  |  |  |  | 795 |  |  |  |  | 800 |  |  |  |  |  |  |
| tgt | gtg | agt | cag | tgt | gca | gca | ttt | gaa | aac | ccc | aag | gga | cta | att | cat |  |  |  |  | 2567 |
| Cys | Val | Ser | Gln | Cys | Ala | Ala | Phe | Glu | Asn | Pro | Lys | Gly | Leu | Ile | His |  |  |  |  |  |
|  |  |  |  | 805 |  |  |  |  | 810 |  |  |  |  | 815 |  |  |  |  |  |  |
| ggt | tgt | tcc | aaa | gat | aat | aga | aat | gac | aca | gaa | ggc | ttt | aag | tat | cca |  |  |  |  | 2615 |
| Gly | Cys | Ser | Lys | Asp | Asn | Arg | Asn | Asp | Thr | Glu | Gly | Phe | Lys | Tyr | Pro |  |  |  |  |  |
|  |  |  | 820 |  |  |  |  | 825 |  |  |  |  | 830 |  |  |  |  |  |  |  |
| ttg | gga | cat | gaa | gtt | aac | cac | agt | cgg | gaa | aca | agc | ata | gaa | atg | gaa |  |  |  |  | 2663 |
| Leu | Gly | His | Glu | Val | Asn | His | Ser | Arg | Glu | Thr | Ser | Ile | Glu | Met | Glu |  |  |  |  |  |
|  |  | 835 |  |  |  |  | 840 |  |  |  |  | 845 |  |  |  |  |  |  |  |  |
| gaa | agt | gaa | ctt | gat | gct | cag | tat | ttg | cag | aat | aca | ttc | aag | gtt | tca |  |  |  |  | 2711 |
| Glu | Ser | Glu | Leu | Asp | Ala | Gln | Tyr | Leu | Gln | Asn | Thr | Phe | Lys | Val | Ser |  |  |  |  |  |
| 850 |  |  |  | 855 |  |  |  |  | 860 |  |  |  |  |  |  |  |  |  |  |  |
| aag | cgc | cag | tca | ttt | gct | ctg | ttt | tca | aat | cca | gga | aat | gca | gaa | gag |  |  |  |  | 2759 |
| Lys | Arg | Gln | Ser | Phe | Ala | Leu | Phe | Ser | Asn | Pro | Gly | Asn | Ala | Glu | Glu |  |  |  |  |  |
| 865 |  |  |  | 870 |  |  |  |  | 875 |  |  |  |  | 880 |  |  |  |  |  |  |
| gaa | tgt | gca | aca | ttc | tct | gcc | cac | tct | ggg | tcc | tta | aag | aaa | caa | agt |  |  |  |  | 2807 |

-continued

| | | |
|---|---|---|
| Glu Cys Ala Thr Phe Ser Ala His Ser Gly Ser Leu Lys Lys Gln Ser<br>                          885                       890                    895 | |
| cca aaa gtc act ttt gaa tgt gaa caa aag gaa gaa aat caa gga aag<br>Pro Lys Val Thr Phe Glu Cys Glu Gln Lys Glu Glu Asn Gln Gly Lys<br>           900                       905                     910 | 2855 |
| aat gag tct aat atc aag cct gta cag aca gtt aat atc act gca ggc<br>Asn Glu Ser Asn Ile Lys Pro Val Gln Thr Val Asn Ile Thr Ala Gly<br>           915                       920                   925 | 2903 |
| ttt cct gtg gtt ggt cag aaa gat aag cca gtt gat aat gcc aaa tgt<br>Phe Pro Val Val Gly Gln Lys Asp Lys Pro Val Asp Asn Ala Lys Cys<br>   930                      935                   940 | 2951 |
| agt atc aaa gga ggc tct agg ttt tgt cta tca tct cag ttc aga ggc<br>Ser Ile Lys Gly Gly Ser Arg Phe Cys Leu Ser Ser Gln Phe Arg Gly<br>945                   950                   955                  960 | 2999 |
| aac gaa act gga ctc att act cca aat aaa cat gga ctt tta caa aac<br>Asn Glu Thr Gly Leu Ile Thr Pro Asn Lys His Gly Leu Leu Gln Asn<br>                         965                   970                  975 | 3047 |
| cca tat cgt ata cca cca ctt ttt ccc atc aag tca ttt gtt aaa act<br>Pro Tyr Arg Ile Pro Pro Leu Phe Pro Ile Lys Ser Phe Val Lys Thr<br>           980                       985                   990 | 3095 |
| aaa tgt aag aaa aat ctg cta gag gaa aac ttt gag gaa cat tca atg<br>Lys Cys Lys Lys Asn Leu Leu Glu Glu Asn Phe Glu Glu His Ser Met<br>         995                    1000                 1005 | 3143 |
| tca cct gaa aga gaa atg gga aat gag aac att cca agt aca gtg<br>Ser Pro Glu Arg Glu Met Gly Asn Glu Asn Ile Pro Ser Thr Val<br>  1010                   1015                  1020 | 3188 |
| agc aca att agc cgt aat aac att aga gaa aat gtt ttt aaa gga<br>Ser Thr Ile Ser Arg Asn Asn Ile Arg Glu Asn Val Phe Lys Gly<br>1025                  1030                  1035 | 3233 |
| gcc agc tca agc aat att aat gaa gta ggt tcc agt act aat gaa<br>Ala Ser Ser Ser Asn Ile Asn Glu Val Gly Ser Ser Thr Asn Glu<br>  1040                   1045                  1050 | 3278 |
| gtg ggc tcc agt att aat gaa ata ggt tcc agt gat gaa aac att<br>Val Gly Ser Ser Ile Asn Glu Ile Gly Ser Ser Asp Glu Asn Ile<br>  1055                   1060                  1065 | 3323 |
| caa gca gaa cta ggt aga aac aga ggg cca aaa ttg aat gct atg<br>Gln Ala Glu Leu Gly Arg Asn Arg Gly Pro Lys Leu Asn Ala Met<br>1070                  1075                  1080 | 3368 |
| ctt aga tta ggg gtt ttg caa cct gag gtc tat aaa caa agt ctt<br>Leu Arg Leu Gly Val Leu Gln Pro Glu Val Tyr Lys Gln Ser Leu<br>  1085                   1090                  1095 | 3413 |
| cct gga agt aat tgt aag cat cct gaa ata aaa aag caa gaa tat<br>Pro Gly Ser Asn Cys Lys His Pro Glu Ile Lys Lys Gln Glu Tyr<br>  1100                   1105                  1110 | 3458 |
| gaa gaa gta gtt cag act gtt aat aca gat ttc tct cca tat ctg<br>Glu Glu Val Val Gln Thr Val Asn Thr Asp Phe Ser Pro Tyr Leu<br>  1115                   1120                  1125 | 3503 |
| att tca gat aac tta gaa cag cct atg gga agt agt cat gca tct<br>Ile Ser Asp Asn Leu Glu Gln Pro Met Gly Ser Ser His Ala Ser<br>  1130                   1135                  1140 | 3548 |
| cag gtt tgt tct gag aca cct gat gac ctg tta gat gat ggt gaa<br>Gln Val Cys Ser Glu Thr Pro Asp Asp Leu Leu Asp Asp Gly Glu<br>  1145                   1150                  1155 | 3593 |
| ata aag gaa gat act agt ttt gct gaa aat gac att aag gaa agt<br>Ile Lys Glu Asp Thr Ser Phe Ala Glu Asn Asp Ile Lys Glu Ser<br>  1160                   1165                  1170 | 3638 |
| tct gct gtt ttt agc aaa agc gtc cag aga gga gag ctt agc agg<br>Ser Ala Val Phe Ser Lys Ser Val Gln Arg Gly Glu Leu Ser Arg<br>  1175                   1180                  1185 | 3683 |

| | | |
|---|---|---|
| agt cct agc cct ttc acc cat aca cat ttg gct cag ggt tac cga<br>Ser Pro Ser Pro Phe Thr His Thr His Leu Ala Gln Gly Tyr Arg<br>1190                      1195                        1200 | | 3728 |
| aga ggg gcc aag aaa tta gag tcc tca gaa gag aac tta tct agt<br>Arg Gly Ala Lys Lys Leu Glu Ser Ser Glu Glu Asn Leu Ser Ser<br>1205                      1210                      1215 | | 3773 |
| gag gat gaa gag ctt ccc tgc ttc caa cac ttg tta ttt ggt aaa<br>Glu Asp Glu Glu Leu Pro Cys Phe Gln His Leu Leu Phe Gly Lys<br>1220                      1225                      1230 | | 3818 |
| gta aac aat ata cct tct cag tct act agg cat agc acc gtt gct<br>Val Asn Asn Ile Pro Ser Gln Ser Thr Arg His Ser Thr Val Ala<br>1235                      1240                      1245 | | 3863 |
| acc gag tgt ctg tct aag aac aca gag gag aat tta tta tca ttg<br>Thr Glu Cys Leu Ser Lys Asn Thr Glu Glu Asn Leu Leu Ser Leu<br>1250                      1255                      1260 | | 3908 |
| aag aat agc tta aat gac tgc agt aac cag gta ata ttg gca aag<br>Lys Asn Ser Leu Asn Asp Cys Ser Asn Gln Val Ile Leu Ala Lys<br>1265                      1270                      1275 | | 3953 |
| gca tct cag gaa cat cac ctt agt gag gaa aca aaa tgt tct gct<br>Ala Ser Gln Glu His His Leu Ser Glu Glu Thr Lys Cys Ser Ala<br>1280                      1285                      1290 | | 3998 |
| agc ttg ttt tct tca cag tgc agt gaa ttg gaa gac ttg act gca<br>Ser Leu Phe Ser Ser Gln Cys Ser Glu Leu Glu Asp Leu Thr Ala<br>1295                      1300                      1305 | | 4043 |
| aat aca aac acc cag gat cct ttc ttg att ggt tct tcc aaa caa<br>Asn Thr Asn Thr Gln Asp Pro Phe Leu Ile Gly Ser Ser Lys Gln<br>1310                      1315                      1320 | | 4088 |
| atg agg cat cag tct gaa agc cag gga gtt ggt ctg agt gac aag<br>Met Arg His Gln Ser Glu Ser Gln Gly Val Gly Leu Ser Asp Lys<br>1325                      1330                      1335 | | 4133 |
| gaa ttg gtt tca gat gat gaa gaa aga gga acg ggc ttg gaa gaa<br>Glu Leu Val Ser Asp Asp Glu Glu Arg Gly Thr Gly Leu Glu Glu<br>1340                      1345                      1350 | | 4178 |
| aat aat caa gaa gag caa agc atg gat tca aac tta ggt gaa gca<br>Asn Asn Gln Glu Glu Gln Ser Met Asp Ser Asn Leu Gly Glu Ala<br>1355                      1360                      1365 | | 4223 |
| gca tct ggg tgt gag agt gaa aca agc gtc tct gaa gac tgc tca<br>Ala Ser Gly Cys Glu Ser Glu Thr Ser Val Ser Glu Asp Cys Ser<br>1370                      1375                      1380 | | 4268 |
| ggg cta tcc tct cag agt gac att tta acc act cag cag agg gat<br>Gly Leu Ser Ser Gln Ser Asp Ile Leu Thr Thr Gln Gln Arg Asp<br>1385                      1390                      1395 | | 4313 |
| acc atg caa cat aac ctg ata aag ctc cag cag gaa atg gct gaa<br>Thr Met Gln His Asn Leu Ile Lys Leu Gln Gln Glu Met Ala Glu<br>1400                      1405                      1410 | | 4358 |
| cta gaa gct gtg tta gaa cag cat ggg agc cag cct tct aac agc<br>Leu Glu Ala Val Leu Glu Gln His Gly Ser Gln Pro Ser Asn Ser<br>1415                      1420                      1425 | | 4403 |
| tac cct tcc atc ata agt gac tct tct gcc ctt gag gac ctg cga<br>Tyr Pro Ser Ile Ile Ser Asp Ser Ser Ala Leu Glu Asp Leu Arg<br>1430                      1435                      1440 | | 4448 |
| aat cca gaa caa agc aca tca gaa aaa gca gta tta act tca cag<br>Asn Pro Glu Gln Ser Thr Ser Glu Lys Ala Val Leu Thr Ser Gln<br>1445                      1450                      1455 | | 4493 |
| aaa agt agt gaa tac cct ata agc cag aat cca gaa ggc ctt tct<br>Lys Ser Ser Glu Tyr Pro Ile Ser Gln Asn Pro Glu Gly Leu Ser<br>1460                      1465                      1470 | | 4538 |
| gct gac aag ttt gag gtg tct gca gat agt tct acc agt aaa aat<br>Ala Asp Lys Phe Glu Val Ser Ala Asp Ser Ser Thr Ser Lys Asn<br>1475                      1480                      1485 | | 4583 |

-continued

```
aaa gaa cca gga gtg gaa agg tca tcc cct tct aaa tgc cca tca        4628
Lys Glu Pro Gly Val Glu Arg Ser Ser Pro Ser Lys Cys Pro Ser
    1490                1495                1500 tta gat gat agg tgg tac atg cac agt tgc tct ggg agt ctt cag        4673
Leu Asp Asp Arg Trp Tyr Met His Ser Cys Ser Gly Ser Leu Gln
1505                1510                1515 aat aga aac tac cca tct caa gag gag ctc att aag gtt gtt gat        4718
Asn Arg Asn Tyr Pro Ser Gln Glu Glu Leu Ile Lys Val Val Asp
        1520                1525                1530 gtg gag gag caa cag ctg gaa gag tct ggg cca cac gat ttg acg        4763
Val Glu Glu Gln Gln Leu Glu Glu Ser Gly Pro His Asp Leu Thr
1535                1540                1545 gaa aca tct tac ttg cca agg caa gat cta gag gga acc cct tac        4808
Glu Thr Ser Tyr Leu Pro Arg Gln Asp Leu Glu Gly Thr Pro Tyr
        1550                1555                1560 ctg gaa tct gga atc agc ctc ttc tct gat gac cct gaa tct gat        4853
Leu Glu Ser Gly Ile Ser Leu Phe Ser Asp Asp Pro Glu Ser Asp
1565                1570                1575 cct tct gaa gac aga gcc cca gag tca gct cgt gtt ggc aac ata        4898
Pro Ser Glu Asp Arg Ala Pro Glu Ser Ala Arg Val Gly Asn Ile
        1580                1585                1590 cca tct tca acc tct gca ttg aaa gtt ccc caa ttg aaa gtt gca        4943
Pro Ser Ser Thr Ser Ala Leu Lys Val Pro Gln Leu Lys Val Ala
1595                1600                1605 gaa tct gcc cag ggt cca gct gct gct cat act act gat act gct        4988
Glu Ser Ala Gln Gly Pro Ala Ala Ala His Thr Thr Asp Thr Ala
        1610                1615                1620 ggg tat aat gca atg gaa gaa agt gtg agc agg gag aag cca gaa        5033
Gly Tyr Asn Ala Met Glu Glu Ser Val Ser Arg Glu Lys Pro Glu
1625                1630                1635 ttg aca gct tca aca gaa agg gtc aac aaa aga atg tcc atg gtg        5078
Leu Thr Ala Ser Thr Glu Arg Val Asn Lys Arg Met Ser Met Val
        1640                1645                1650 gtg tct ggc ctg acc cca gaa gaa ttt atg ctc gtg tac aag ttt        5123
Val Ser Gly Leu Thr Pro Glu Glu Phe Met Leu Val Tyr Lys Phe
1655                1660                1665 gcc aga aaa cac cac atc act tta act aat cta att act gaa gag        5168
Ala Arg Lys His His Ile Thr Leu Thr Asn Leu Ile Thr Glu Glu
        1670                1675                1680 act act cat gtt gtt atg aaa aca gat gct gag ttt gtg tgt gaa        5213
Thr Thr His Val Val Met Lys Thr Asp Ala Glu Phe Val Cys Glu
1685                1690                1695 cgg aca ctg aaa tat ttt cta gga att gcg gga gga aaa tgg gta        5258
Arg Thr Leu Lys Tyr Phe Leu Gly Ile Ala Gly Gly Lys Trp Val
1700                1705                1710 gtt agc tat ttc tgg gtg acc cag tct att aaa gaa aga aaa atg        5303
Val Ser Tyr Phe Trp Val Thr Gln Ser Ile Lys Glu Arg Lys Met
        1715                1720                1725 ctg aat gag cat gat ttt gaa gtc aga gga gat gtg gtc aat gga        5348
Leu Asn Glu His Asp Phe Glu Val Arg Gly Asp Val Val Asn Gly
1730                1735                1740 aga aac cac caa ggt cca aag cga gca aga gaa tcc cag gac aga        5393
Arg Asn His Gln Gly Pro Lys Arg Ala Arg Glu Ser Gln Asp Arg
        1745                1750                1755 aag atc ttc agg ggg cta gaa atc tgt tgc tat ggg ccc ttc acc        5438
Lys Ile Phe Arg Gly Leu Glu Ile Cys Cys Tyr Gly Pro Phe Thr
1760                1765                1770 aac atg ccc aca gat caa ctg gaa tgg atg gta cag ctg tgt ggt        5483
Asn Met Pro Thr Asp Gln Leu Glu Trp Met Val Gln Leu Cys Gly
```

-continued

| | | | |
|---|---|---|---|
| gct tct gtg gtg aag gag ctt tca tca ttc acc ctt ggc aca ggt<br>Ala Ser Val Val Lys Glu Leu Ser Ser Phe Thr Leu Gly Thr Gly<br>     1790                     1795                     1800 | 5528 |
| gtc cac cca att gtg gtt gtg cag cca gat gcc tgg aca gag gac<br>Val His Pro Ile Val Val Val Gln Pro Asp Ala Trp Thr Glu Asp<br>     1805                     1810                     1815 | 5573 |
| aat ggc ttc cat gca att ggg cag atg tgt gag gca cct gtg gtg<br>Asn Gly Phe His Ala Ile Gly Gln Met Cys Glu Ala Pro Val Val<br>     1820                     1825                     1830 | 5618 |
| acc cga gag tgg gtg ttg gac agt gta gca ctc tac cag tgc cag<br>Thr Arg Glu Trp Val Leu Asp Ser Val Ala Leu Tyr Gln Cys Gln<br>     1835                     1840                     1845 | 5663 |
| gag ctg gac acc tac ctg ata ccc cag atc ccc cac agc cac tac<br>Glu Leu Asp Thr Tyr Leu Ile Pro Gln Ile Pro His Ser His Tyr<br>     1850                     1855                     1860 | 5708 |
| tga | 5711 |

<210> SEQ ID NO 266
<211> LENGTH: 1863
<212> TYPE: PRT
<213> ORGANISM: Homo sapiens

<400> SEQUENCE: 266

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255
```

-continued

```
His Pro Glu Lys Tyr Gln Gly Ser Ser Val Ser Asn Leu His Val Glu
        260                 265                 270

Pro Cys Gly Thr Asn Thr His Ala Ser Ser Leu Gln His Glu Asn Ser
        275                 280                 285

Ser Leu Leu Thr Lys Asp Arg Met Asn Val Glu Lys Ala Glu Phe
        290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
        340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
        370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
        500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
        530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
                595                 600                 605

Asn Arg Leu Arg Arg Lys Ser Ser Thr Arg His Ile His Ala Leu Glu
        610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670
```

-continued

```
Glu Pro Ala Thr Gly Ala Lys Lys Ser Asn Lys Pro Asn Glu Gln Thr
                675                 680                 685

Ser Lys Arg His Asp Ser Asp Thr Phe Pro Glu Leu Lys Leu Thr Asn
            690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
850                 855                 860

Lys Arg Gln Ser Phe Ala Leu Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu  Glu Asn Phe Glu Glu  His Ser Met
        995                 1000                 1005

Ser Pro Glu Arg Glu Met Gly  Asn Glu Asn Ile Pro  Ser Thr Val
        1010                1015                1020

Ser Thr Ile Ser Arg Asn Asn  Ile Arg Glu Asn Val  Phe Lys Gly
        1025                1030                1035

Ala Ser Ser Ser Asn Ile Asn  Glu Val Gly Ser Ser  Thr Asn Glu
        1040                1045                1050

Val Gly Ser Ser Ile Asn Glu  Ile Gly Ser Ser Asp  Glu Asn Ile
        1055                1060                1065

Gln Ala Glu Leu Gly Arg Asn  Arg Gly Pro Lys Leu  Asn Ala Met
        1070                1075                1080

Leu Arg Leu Gly Val Leu Gln  Pro Glu Val Tyr Lys  Gln Ser Leu
```

-continued

```
            1085                1090                1095
Pro Gly Ser Asn Cys Lys His Pro Glu Ile Lys Lys Gln Glu Tyr
        1100                1105                1110
Glu Glu Val Val Gln Thr Val Asn Thr Asp Phe Ser Pro Tyr Leu
        1115                1120                1125
Ile Ser Asp Asn Leu Glu Gln Pro Met Gly Ser Ser His Ala Ser
        1130                1135                1140
Gln Val Cys Ser Glu Thr Pro Asp Asp Leu Leu Asp Asp Gly Glu
        1145                1150                1155
Ile Lys Glu Asp Thr Ser Phe Ala Glu Asn Asp Ile Lys Glu Ser
        1160                1165                1170
Ser Ala Val Phe Ser Lys Ser Val Gln Arg Gly Glu Leu Ser Arg
        1175                1180                1185
Ser Pro Ser Pro Phe Thr His Thr His Leu Ala Gln Gly Tyr Arg
        1190                1195                1200
Arg Gly Ala Lys Lys Leu Glu Ser Ser Glu Glu Asn Leu Ser Ser
        1205                1210                1215
Glu Asp Glu Glu Leu Pro Cys Phe Gln His Leu Leu Phe Gly Lys
        1220                1225                1230
Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu
        1250                1255                1260
Lys Asn Ser Leu Asn Asp Cys Ser Asn Gln Val Ile Leu Ala Lys
        1265                1270                1275
Ala Ser Gln Glu His His Leu Ser Glu Glu Thr Lys Cys Ser Ala
        1280                1285                1290
Ser Leu Phe Ser Ser Gln Cys Ser Glu Leu Glu Asp Leu Thr Ala
        1295                1300                1305
Asn Thr Asn Thr Gln Asp Pro Phe Leu Ile Gly Ser Ser Lys Gln
        1310                1315                1320
Met Arg His Gln Ser Glu Ser Gln Gly Val Gly Leu Ser Asp Lys
        1325                1330                1335
Glu Leu Val Ser Asp Asp Glu Glu Arg Gly Thr Gly Leu Glu Glu
        1340                1345                1350
Asn Asn Gln Glu Glu Gln Ser Met Asp Ser Asn Leu Gly Glu Ala
        1355                1360                1365
Ala Ser Gly Cys Glu Ser Glu Thr Ser Val Ser Glu Asp Cys Ser
        1370                1375                1380
Gly Leu Ser Ser Gln Ser Asp Ile Leu Thr Thr Gln Gln Arg Asp
        1385                1390                1395
Thr Met Gln His Asn Leu Ile Lys Leu Gln Gln Glu Met Ala Glu
        1400                1405                1410
Leu Glu Ala Val Leu Glu Gln His Gly Ser Gln Pro Ser Asn Ser
        1415                1420                1425
Tyr Pro Ser Ile Ile Ser Asp Ser Ser Ala Leu Glu Asp Leu Arg
        1430                1435                1440
Asn Pro Glu Gln Ser Thr Ser Glu Lys Ala Val Leu Thr Ser Gln
        1445                1450                1455
Lys Ser Ser Glu Tyr Pro Ile Ser Gln Asn Pro Glu Gly Leu Ser
        1460                1465                1470
Ala Asp Lys Phe Glu Val Ser Ala Asp Ser Ser Thr Ser Lys Asn
        1475                1480                1485
```

-continued

```
Lys Glu Pro Gly Val Glu Arg Ser Ser Pro Ser Lys Cys Pro Ser
1490                1495                1500

Leu Asp Asp Arg Trp Tyr Met His Ser Cys Ser Gly Ser Leu Gln
1505                1510                1515

Asn Arg Asn Tyr Pro Ser Gln Glu Leu Ile Lys Val Val Asp
1520                1525                1530

Val Glu Glu Gln Gln Leu Glu Glu Ser Gly Pro His Asp Leu Thr
1535                1540                1545

Glu Thr Ser Tyr Leu Pro Arg Gln Asp Leu Glu Gly Thr Pro Tyr
1550                1555                1560

Leu Glu Ser Gly Ile Ser Leu Phe Ser Asp Asp Pro Glu Ser Asp
1565                1570                1575

Pro Ser Glu Asp Arg Ala Pro Glu Ser Ala Arg Val Gly Asn Ile
1580                1585                1590

Pro Ser Ser Thr Ser Ala Leu Lys Val Pro Gln Leu Lys Val Ala
1595                1600                1605

Glu Ser Ala Gln Gly Pro Ala Ala Ala His Thr Thr Asp Thr Ala
1610                1615                1620

Gly Tyr Asn Ala Met Glu Glu Ser Val Ser Arg Glu Lys Pro Glu
1625                1630                1635

Leu Thr Ala Ser Thr Glu Arg Val Asn Lys Arg Met Ser Met Val
1640                1645                1650

Val Ser Gly Leu Thr Pro Glu Glu Phe Met Leu Val Tyr Lys Phe
1655                1660                1665

Ala Arg Lys His His Ile Thr Leu Thr Asn Leu Ile Thr Glu Glu
1670                1675                1680

Thr Thr His Val Val Met Lys Thr Asp Ala Glu Phe Val Cys Glu
1685                1690                1695

Arg Thr Leu Lys Tyr Phe Leu Gly Ile Ala Gly Gly Lys Trp Val
1700                1705                1710

Val Ser Tyr Phe Trp Val Thr Gln Ser Ile Lys Glu Arg Lys Met
1715                1720                1725

Leu Asn Glu His Asp Phe Glu Val Arg Gly Asp Val Val Asn Gly
1730                1735                1740

Arg Asn His Gln Gly Pro Lys Arg Ala Arg Glu Ser Gln Asp Arg
1745                1750                1755

Lys Ile Phe Arg Gly Leu Glu Ile Cys Cys Tyr Gly Pro Phe Thr
1760                1765                1770

Asn Met Pro Thr Asp Gln Leu Glu Trp Met Val Gln Leu Cys Gly
1775                1780                1785

Ala Ser Val Val Lys Glu Leu Ser Ser Phe Thr Leu Gly Thr Gly
1790                1795                1800

Val His Pro Ile Val Val Gln Pro Asp Ala Trp Thr Glu Asp
1805                1810                1815

Asn Gly Phe His Ala Ile Gly Gln Met Cys Glu Ala Pro Val Val
1820                1825                1830

Thr Arg Glu Trp Val Leu Asp Ser Val Ala Leu Tyr Gln Cys Gln
1835                1840                1845

Glu Leu Asp Thr Tyr Leu Ile Pro Gln Ile Pro His Ser His Tyr
1850                1855                1860
```

<210> SEQ ID NO 267
<211> LENGTH: 5711

```
<212> TYPE: DNA
<213> ORGANISM: Homo sapiens
<220> FEATURE:
<221> NAME/KEY: CDS
<222> LOCATION: (120)..(5711)
<223> OTHER INFORMATION: omi3 sequences

<400> SEQUENCE: 267
agctcgctga gacttcctgg accccgcacc aggctgtggg gtttctcaga taactgggcc      60
cctgcgctca ggaggccttc accctctgct ctgggtaaag ttcattggaa cagaaagaa      119
```

| | | | | | | | | | | | | | | | | |
|---|---|---|---|---|---|---|---|---|---|---|---|---|---|---|---|---|
| atg | gat | tta | tct | gct | ctt | cgc | gtt | gaa | gaa | gta | caa | aat | gtc | att | aat | 167 |
| Met | Asp | Leu | Ser | Ala | Leu | Arg | Val | Glu | Glu | Val | Gln | Asn | Val | Ile | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gct | atg | cag | aaa | atc | tta | gag | tgt | ccc | atc | tgt | ctg | gag | ttg | atc | aag | 215 |
| Ala | Met | Gln | Lys | Ile | Leu | Glu | Cys | Pro | Ile | Cys | Leu | Glu | Leu | Ile | Lys | |
| | | 20 | | | | | 25 | | | | | 30 | | | | |

| | | | | | | | | | | | | | | | | |
|---|---|---|---|---|---|---|---|---|---|---|---|---|---|---|---|---|
| gaa | cct | gtc | tcc | aca | aag | tgt | gac | cac | ata | ttt | tgc | aaa | ttt | tgc | atg | 263 |
| Glu | Pro | Val | Ser | Thr | Lys | Cys | Asp | His | Ile | Phe | Cys | Lys | Phe | Cys | Met | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | aaa | ctt | ctc | aac | cag | aag | aaa | ggg | cct | tca | cag | tgt | cct | tta | tgt | 311 |
| Leu | Lys | Leu | Leu | Asn | Gln | Lys | Lys | Gly | Pro | Ser | Gln | Cys | Pro | Leu | Cys | |
| 50 | | | | | 55 | | | | | 60 | | | | | | |

| | | | | | | | | | | | | | | | | |
|---|---|---|---|---|---|---|---|---|---|---|---|---|---|---|---|---|
| aag | aat | gat | ata | acc | aaa | agg | agc | cta | caa | gaa | agt | acg | aga | ttt | agt | 359 |
| Lys | Asn | Asp | Ile | Thr | Lys | Arg | Ser | Leu | Gln | Glu | Ser | Thr | Arg | Phe | Ser | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| caa | ctt | gtt | gaa | gag | cta | ttg | aaa | atc | att | tgt | gct | ttt | cag | ctt | gac | 407 |
| Gln | Leu | Val | Glu | Glu | Leu | Leu | Lys | Ile | Ile | Cys | Ala | Phe | Gln | Leu | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | ggt | ttg | gag | tat | gca | aac | agc | tat | aat | ttt | gca | aaa | aag | gaa | aat | 455 |
| Thr | Gly | Leu | Glu | Tyr | Ala | Asn | Ser | Tyr | Asn | Phe | Ala | Lys | Lys | Glu | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| aac | tct | cct | gaa | cat | cta | aaa | gat | gaa | gtt | tct | atc | atc | caa | agt | atg | 503 |
| Asn | Ser | Pro | Glu | His | Leu | Lys | Asp | Glu | Val | Ser | Ile | Ile | Gln | Ser | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | tac | aga | aac | cgt | gcc | aaa | aga | ctt | cta | cag | agt | gaa | ccc | gaa | aat | 551 |
| Gly | Tyr | Arg | Asn | Arg | Ala | Lys | Arg | Leu | Leu | Gln | Ser | Glu | Pro | Glu | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| cct | tcc | ttg | cag | gaa | acc | agt | ctc | agt | gtc | caa | ctc | tct | aac | ctt | gga | 599 |
| Pro | Ser | Leu | Gln | Glu | Thr | Ser | Leu | Ser | Val | Gln | Leu | Ser | Asn | Leu | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| act | gtg | aga | act | ctg | agg | aca | aag | cag | cgg | ata | caa | cct | caa | aag | acg | 647 |
| Thr | Val | Arg | Thr | Leu | Arg | Thr | Lys | Gln | Arg | Ile | Gln | Pro | Gln | Lys | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| tct | gtc | tac | att | gaa | ttg | gga | tct | gat | tct | tct | gaa | gat | acc | gtt | aat | 695 |
| Ser | Val | Tyr | Ile | Glu | Leu | Gly | Ser | Asp | Ser | Ser | Glu | Asp | Thr | Val | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| aag | gca | act | tat | tgc | agt | gtg | gga | gat | caa | gaa | ttg | tta | caa | atc | acc | 743 |
| Lys | Ala | Thr | Tyr | Cys | Ser | Val | Gly | Asp | Gln | Glu | Leu | Leu | Gln | Ile | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| cct | caa | gga | acc | agg | gat | gaa | atc | agt | ttg | gat | tct | gca | aaa | aag | gct | 791 |
| Pro | Gln | Gly | Thr | Arg | Asp | Glu | Ile | Ser | Leu | Asp | Ser | Ala | Lys | Lys | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| gct | tgt | gaa | ttt | tct | gag | acg | gat | gta | aca | aat | act | gaa | cat | cat | caa | 839 |
| Ala | Cys | Glu | Phe | Ser | Glu | Thr | Asp | Val | Thr | Asn | Thr | Glu | His | His | Gln | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccc | agt | aat | aat | gat | ttg | aac | acc | act | gag | aag | cgt | gca | gct | gag | agg | 887 |
| Pro | Ser | Asn | Asn | Asp | Leu | Asn | Thr | Thr | Glu | Lys | Arg | Ala | Ala | Glu | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| cat | cca | gaa | aag | tat | cag | ggt | agt | tct | gtt | tca | aac | ttg | cat | gtg | gag | 935 |
| His | Pro | Glu | Lys | Tyr | Gln | Gly | Ser | Ser | Val | Ser | Asn | Leu | His | Val | Glu | |

```
                260              265              270
cca tgt ggc aca aat act cat gcc agc tca tta cag cat gag aac agc        983
Pro Cys Gly Thr Asn Thr His Ala Ser Ser Leu Gln His Glu Asn Ser
        275              280              285 agt tta tta ctc act aaa gac aga atg aat gta gaa aag gct gaa ttc       1031
Ser Leu Leu Thr Lys Asp Arg Met Asn Val Glu Lys Ala Glu Phe
    290              295              300 tgt aat aaa agc aaa cag cct ggc tta gca agg agc caa cat aac aga       1079
Cys Asn Lys Ser Lys Gln Pro Gly Leu Ala Arg Ser Gln His Asn Arg
305              310              315              320 tgg gct gga agt aag gaa aca tgt aat gat agg cgg act ccc agc aca       1127
Trp Ala Gly Ser Lys Glu Thr Cys Asn Asp Arg Arg Thr Pro Ser Thr
            325              330              335 gaa aaa aag gta gat ctg aat gct gat ccc ctg tgt gag aga aaa gaa       1175
Glu Lys Lys Val Asp Leu Asn Ala Asp Pro Leu Cys Glu Arg Lys Glu
        340              345              350 tgg aat aag cag aaa ctg cca tgc tca gag aat cct aga gat act gaa       1223
Trp Asn Lys Gln Lys Leu Pro Cys Ser Glu Asn Pro Arg Asp Thr Glu
    355              360              365 gat gtt cct tgg ata aca cta aat agc agc att cag aaa gtt aat gag       1271
Asp Val Pro Trp Ile Thr Leu Asn Ser Ser Ile Gln Lys Val Asn Glu
370              375              380 tgg ttt tcc aga agt gat gaa ctg tta ggt tct gat gac tca cat gat       1319
Trp Phe Ser Arg Ser Asp Glu Leu Leu Gly Ser Asp Asp Ser His Asp
385              390              395              400 ggg gag tct gaa tca aat gcc aaa gta gct gat gta ttg gac gtt cta       1367
Gly Glu Ser Glu Ser Asn Ala Lys Val Ala Asp Val Leu Asp Val Leu
            405              410              415 aat gag gta gat gaa tat tct ggt tct tca gag aaa ata gac tta ctg       1415
Asn Glu Val Asp Glu Tyr Ser Gly Ser Ser Glu Lys Ile Asp Leu Leu
        420              425              430 gcc agt gat cct cat gag gct tta ata tgt aaa agt gaa aga gtt cac       1463
Ala Ser Asp Pro His Glu Ala Leu Ile Cys Lys Ser Glu Arg Val His
    435              440              445 tcc aaa tca gta gag agt aat att gaa gac aaa ata ttt ggg aaa acc       1511
Ser Lys Ser Val Glu Ser Asn Ile Glu Asp Lys Ile Phe Gly Lys Thr
450              455              460 tat cgg aag aag gca agc ctc ccc aac tta agc cat gta act gaa aat       1559
Tyr Arg Lys Lys Ala Ser Leu Pro Asn Leu Ser His Val Thr Glu Asn
465              470              475              480 cta att ata gga gca ttt gtt act gag cca cag ata ata caa gag cgt       1607
Leu Ile Ile Gly Ala Phe Val Thr Glu Pro Gln Ile Ile Gln Glu Arg
            485              490              495 ccc ctc aca aat aaa tta aag cgt aaa agg aga cct aca tca ggc ctt       1655
Pro Leu Thr Asn Lys Leu Lys Arg Lys Arg Arg Pro Thr Ser Gly Leu
        500              505              510 cat cct gag gat ttt atc aag aaa gca gat ttg gca gtt caa aag act       1703
His Pro Glu Asp Phe Ile Lys Lys Ala Asp Leu Ala Val Gln Lys Thr
    515              520              525 cct gaa atg ata aat cag gga act aac caa acg gag cag aat ggt caa       1751
Pro Glu Met Ile Asn Gln Gly Thr Asn Gln Thr Glu Gln Asn Gly Gln
530              535              540 gtg atg aat att act aat agt ggt cat gag aat aaa aca aaa ggt gat       1799
Val Met Asn Ile Thr Asn Ser Gly His Glu Asn Lys Thr Lys Gly Asp
545              550              555              560 tct att cag aat gag aaa aat cct aac cca ata gaa tca ctc gaa aaa       1847
Ser Ile Gln Asn Glu Lys Asn Pro Asn Pro Ile Glu Ser Leu Glu Lys
            565              570              575 gaa tct gct ttc aaa acg aaa gct gaa cct ata agc agc agt ata agc       1895
```

```
Glu Ser Ala Phe Lys Thr Lys Ala Glu Pro Ile Ser Ser Ile Ser
        580             585             590 aat atg gaa ctc gaa tta aat atc cac aat tca aaa gca cct aaa aag    1943
Asn Met Glu Leu Glu Leu Asn Ile His Asn Ser Lys Ala Pro Lys Lys
        595             600             605 aat agg ctg agg agg aag tct tct acc agg cat att cat gcg ctt gaa    1991
Asn Arg Leu Arg Arg Lys Ser Ser Thr Arg His Ile His Ala Leu Glu
610             615             620 cta gta gtc agt aga aat cta agc cca cct aat tgt act gaa ttg caa    2039
Leu Val Val Ser Arg Asn Leu Ser Pro Pro Asn Cys Thr Glu Leu Gln
625             630             635             640 att gat agt tgt tct agc agt gaa gag ata aag aaa aaa aag tac aac    2087
Ile Asp Ser Cys Ser Ser Ser Glu Glu Ile Lys Lys Lys Lys Tyr Asn
                645             650             655 caa atg cca gtc agg cac agc aga aac cta caa ctc atg gaa ggt aaa    2135
Gln Met Pro Val Arg His Ser Arg Asn Leu Gln Leu Met Glu Gly Lys
        660             665             670 gaa cct gca act gga gcc aag aag agt aac aag cca aat gaa cag aca    2183
Glu Pro Ala Thr Gly Ala Lys Lys Ser Asn Lys Pro Asn Glu Gln Thr
        675             680             685 agt aaa aga cat gac agc gat act ttc cca gag ctg aag tta aca aat    2231
Ser Lys Arg His Asp Ser Asp Thr Phe Pro Glu Leu Lys Leu Thr Asn
690             695             700 gca cct ggt tct ttt act aag tgt tca aat acc agt gaa ctt aaa gaa    2279
Ala Pro Gly Ser Phe Thr Lys Cys Ser Asn Thr Ser Glu Leu Lys Glu
705             710             715             720 ttt gtc aat cct agc ctt cca aga gaa gaa aaa gaa gag aaa cta gaa    2327
Phe Val Asn Pro Ser Leu Pro Arg Glu Glu Lys Glu Glu Lys Leu Glu
                725             730             735 aca gtt aaa gtg tct aat aat gct gaa gac ccc aaa gat ctc atg tta    2375
Thr Val Lys Val Ser Asn Asn Ala Glu Asp Pro Lys Asp Leu Met Leu
        740             745             750 agt gga gaa agg gtt ttg caa act gaa aga tct gta gag agt agc agt    2423
Ser Gly Glu Arg Val Leu Gln Thr Glu Arg Ser Val Glu Ser Ser Ser
        755             760             765 att tca ttg gta cct ggt act gat tat ggc act cag gaa agt atc tcg    2471
Ile Ser Leu Val Pro Gly Thr Asp Tyr Gly Thr Gln Glu Ser Ile Ser
770             775             780 tta ctg gaa gtt agc act cta ggg aag gca aaa aca gaa cca aat aaa    2519
Leu Leu Glu Val Ser Thr Leu Gly Lys Ala Lys Thr Glu Pro Asn Lys
785             790             795             800 tgt gtg agt cag tgt gca gca ttt gaa aac ccc aag gga cta att cat    2567
Cys Val Ser Gln Cys Ala Ala Phe Glu Asn Pro Lys Gly Leu Ile His
                805             810             815 ggt tgt tcc aaa gat aat aga aat gac aca gaa ggc ttt aag tat cca    2615
Gly Cys Ser Lys Asp Asn Arg Asn Asp Thr Glu Gly Phe Lys Tyr Pro
        820             825             830 ttg gga cat gaa gtt aac cac agt cgg gaa aca agc ata gaa atg gaa    2663
Leu Gly His Glu Val Asn His Ser Arg Glu Thr Ser Ile Glu Met Glu
        835             840             845 gaa agt gaa ctt gat gct cag tat ttg cag aat aca ttc aag gtt tca    2711
Glu Ser Glu Leu Asp Ala Gln Tyr Leu Gln Asn Thr Phe Lys Val Ser
850             855             860 aag cgc cag tca ttt gct ctg ttt tca aat cca gga aat gca gaa gag    2759
Lys Arg Gln Ser Phe Ala Leu Phe Ser Asn Pro Gly Asn Ala Glu Glu
865             870             875             880 gaa tgt gca aca ttc tct gcc cac tct ggg tcc tta aag aaa caa agt    2807
Glu Cys Ala Thr Phe Ser Ala His Ser Gly Ser Leu Lys Lys Gln Ser
                885             890             895
```

```
                                              -continued cca aaa gtc act ttt gaa tgt gaa caa aag gaa gaa aat caa gga aag       2855
Pro Lys Val Thr Phe Glu Cys Glu Gln Lys Glu Glu Asn Gln Gly Lys
        900                 905                 910 aat gag tct aat atc aag cct gta cag aca gtt aat atc act gca ggc       2903
Asn Glu Ser Asn Ile Lys Pro Val Gln Thr Val Asn Ile Thr Ala Gly
    915                 920                 925 ttt cct gtg gtt ggt cag aaa gat aag cca gtt gat aat gcc aaa tgt       2951
Phe Pro Val Val Gly Gln Lys Asp Lys Pro Val Asp Asn Ala Lys Cys
930                 935                 940 agt atc aaa gga ggc tct agg ttt tgt cta tca tct cag ttc aga ggc       2999
Ser Ile Lys Gly Gly Ser Arg Phe Cys Leu Ser Ser Gln Phe Arg Gly
945                 950                 955                 960 aac gaa act gga ctc att act cca aat aaa cat gga ctt tta caa aac       3047
Asn Glu Thr Gly Leu Ile Thr Pro Asn Lys His Gly Leu Leu Gln Asn
                965                 970                 975 cca tat cgt ata cca cca ctt ttt ccc atc aag tca ttt gtt aaa act       3095
Pro Tyr Arg Ile Pro Pro Leu Phe Pro Ile Lys Ser Phe Val Lys Thr
            980                 985                 990 aaa tgt aag aaa aat ctg cta gag gaa aac ttt gag gaa cat tca atg       3143
Lys Cys Lys Lys Asn Leu Leu Glu Glu Asn Phe Glu Glu His Ser Met
        995                 1000                1005 tca cct gaa aga gaa atg gga aat gag aac att cca agt aca gtg           3188
Ser Pro Glu Arg Glu Met Gly Asn Glu Asn Ile Pro Ser Thr Val
    1010                1015                1020 agc aca att agc cgt aat aac att aga gaa aat gtt ttt aaa gaa           3233
Ser Thr Ile Ser Arg Asn Asn Ile Arg Glu Asn Val Phe Lys Glu
1025                1030                1035 gcc agc tca agc aat att aat gaa gta ggt tcc agt act aat gaa           3278
Ala Ser Ser Ser Asn Ile Asn Glu Val Gly Ser Ser Thr Asn Glu
1040                1045                1050 gtg ggc tcc agt att aat gaa ata ggt tcc agt gat gaa aac att           3323
Val Gly Ser Ser Ile Asn Glu Ile Gly Ser Ser Asp Glu Asn Ile
1055                1060                1065 caa gca gaa cta ggt aga aac aga ggg cca aaa ttg aat gct atg           3368
Gln Ala Glu Leu Gly Arg Asn Arg Gly Pro Lys Leu Asn Ala Met
1070                1075                1080 ctt aga tta ggg gtt ttg caa cct gag gtc tat aaa caa agt ctt           3413
Leu Arg Leu Gly Val Leu Gln Pro Glu Val Tyr Lys Gln Ser Leu
1085                1090                1095 cct gga agt aat tgt aag cat cct gaa ata aaa aag caa gaa tat           3458
Pro Gly Ser Asn Cys Lys His Pro Glu Ile Lys Lys Gln Glu Tyr
1100                1105                1110 gaa gaa gta gtt cag act gtt aat aca gat ttc tct cca tat ctg           3503
Glu Glu Val Val Gln Thr Val Asn Thr Asp Phe Ser Pro Tyr Leu
1115                1120                1125 att tca gat aac tta gaa cag cct atg gga agt agt cat gca tct           3548
Ile Ser Asp Asn Leu Glu Gln Pro Met Gly Ser Ser His Ala Ser
1130                1135                1140 cag gtt tgt tct gag aca cct gat gac ctg tta gat gat ggt gaa           3593
Gln Val Cys Ser Glu Thr Pro Asp Asp Leu Leu Asp Asp Gly Glu
1145                1150                1155 ata aag gaa gat act agt ttt gct gaa aat gac att aag gaa agt           3638
Ile Lys Glu Asp Thr Ser Phe Ala Glu Asn Asp Ile Lys Glu Ser
1160                1165                1170 tct gct gtt ttt agc aaa agc gtc cag aaa gga gag ctt agc agg           3683
Ser Ala Val Phe Ser Lys Ser Val Gln Lys Gly Glu Leu Ser Arg
1175                1180                1185 agt cct agc cct ttc acc cat aca cat ttg gct cag ggt tac cga           3728
Ser Pro Ser Pro Phe Thr His Thr His Leu Ala Gln Gly Tyr Arg
1190                1195                1200
```

-continued

| | | |
|---|---|---|
| aga ggg gcc aag aaa tta gag tcc tca gaa gag aac tta tct agt<br>Arg Gly Ala Lys Lys Leu Glu Ser Ser Glu Glu Asn Leu Ser Ser<br>1205                    1210                    1215 | 3773 |
| gag gat gaa gag ctt ccc tgc ttc caa cac ttg tta ttt ggt aaa<br>Glu Asp Glu Glu Leu Pro Cys Phe Gln His Leu Leu Phe Gly Lys<br>1220                    1225                    1230 | 3818 |
| gta aac aat ata cct tct cag tct act agg cat agc acc gtt gct<br>Val Asn Asn Ile Pro Ser Gln Ser Thr Arg His Ser Thr Val Ala<br>1235                    1240                    1245 | 3863 |
| acc gag tgt ctg tct aag aac aca gag gag aat tta tta tca ttg<br>Thr Glu Cys Leu Ser Lys Asn Thr Glu Glu Asn Leu Leu Ser Leu<br>1250                    1255                    1260 | 3908 |
| aag aat agc tta aat gac tgc agt aac cag gta ata ttg gca aag<br>Lys Asn Ser Leu Asn Asp Cys Ser Asn Gln Val Ile Leu Ala Lys<br>1265                    1270                    1275 | 3953 |
| gca tct cag gaa cat cac ctt agt gag gaa aca aaa tgt tct gct<br>Ala Ser Gln Glu His His Leu Ser Glu Glu Thr Lys Cys Ser Ala<br>1280                    1285                    1290 | 3998 |
| agc ttg ttt tct tca cag tgc agt gaa ttg gaa gac ttg act gca<br>Ser Leu Phe Ser Ser Gln Cys Ser Glu Leu Glu Asp Leu Thr Ala<br>1295                    1300                    1305 | 4043 |
| aat aca aac acc cag gat cct ttc ttg att ggt tct tcc aaa caa<br>Asn Thr Asn Thr Gln Asp Pro Phe Leu Ile Gly Ser Ser Lys Gln<br>1310                    1315                    1320 | 4088 |
| atg agg cat cag tct gaa agc cag gga gtt ggt ctg agt gac aag<br>Met Arg His Gln Ser Glu Ser Gln Gly Val Gly Leu Ser Asp Lys<br>1325                    1330                    1335 | 4133 |
| gaa ttg gtt tca gat gat gaa gaa aga gga acg ggc ttg gaa gaa<br>Glu Leu Val Ser Asp Asp Glu Glu Arg Gly Thr Gly Leu Glu Glu<br>1340                    1345                    1350 | 4178 |
| aat aat caa gaa gag caa agc atg gat tca aac tta ggt gaa gca<br>Asn Asn Gln Glu Glu Gln Ser Met Asp Ser Asn Leu Gly Glu Ala<br>1355                    1360                    1365 | 4223 |
| gca tct ggg tgt gag agt gaa aca agc gtc tct gaa gac tgc tca<br>Ala Ser Gly Cys Glu Ser Glu Thr Ser Val Ser Glu Asp Cys Ser<br>1370                    1375                    1380 | 4268 |
| ggg cta tcc tct cag agt gac att tta acc act cag cag agg gat<br>Gly Leu Ser Ser Gln Ser Asp Ile Leu Thr Thr Gln Gln Arg Asp<br>1385                    1390                    1395 | 4313 |
| acc atg caa cat aac ctg ata aag ctc cag cag gaa atg gct gaa<br>Thr Met Gln His Asn Leu Ile Lys Leu Gln Gln Glu Met Ala Glu<br>1400                    1405                    1410 | 4358 |
| cta gaa gct gtg tta gaa cag cat ggg agc cag cct tct aac agc<br>Leu Glu Ala Val Leu Glu Gln His Gly Ser Gln Pro Ser Asn Ser<br>1415                    1420                    1425 | 4403 |
| tac cct tcc atc ata agt gac tct tct gcc ctt gag gac ctg cga<br>Tyr Pro Ser Ile Ile Ser Asp Ser Ser Ala Leu Glu Asp Leu Arg<br>1430                    1435                    1440 | 4448 |
| aat cca gaa caa agc aca tca gaa aaa gca gta tta act tca cag<br>Asn Pro Glu Gln Ser Thr Ser Glu Lys Ala Val Leu Thr Ser Gln<br>1445                    1450                    1455 | 4493 |
| aaa agt agt gaa tac cct ata agc cag aat cca gaa ggc ctt tct<br>Lys Ser Ser Glu Tyr Pro Ile Ser Gln Asn Pro Glu Gly Leu Ser<br>1460                    1465                    1470 | 4538 |
| gct gac aag ttt gag gtg tct gca gat agt tct acc agt aaa aat<br>Ala Asp Lys Phe Glu Val Ser Ala Asp Ser Ser Thr Ser Lys Asn<br>1475                    1480                    1485 | 4583 |
| aaa gaa cca gga gtg gaa agg tca tcc cct tct aaa tgc cca tca<br>Lys Glu Pro Gly Val Glu Arg Ser Ser Pro Ser Lys Cys Pro Ser | 4628 |

-continued

| | | | | | | | | | | | |
|---|---|---|---|---|---|---|---|---|---|---|---|
| | | | 1490 | | | 1495 | | | 1500 | | |
| tta<br>Leu | gat<br>Asp | gat<br>Asp | agg<br>Arg<br>1505 | tgg<br>Trp | tac<br>Tyr | atg<br>Met<br>1510 | cac<br>His | agt<br>Ser | tgc<br>Cys | tct<br>Ser<br>1515 | ggg<br>Gly | agt<br>Ser | ctt<br>Leu | cag<br>Gln | 4673 |
| aat<br>Asn | aga<br>Arg | aac<br>Asn | tac<br>Tyr<br>1520 | cca<br>Pro | tct<br>Ser | caa<br>Gln<br>1525 | gag<br>Glu | gag<br>Glu | ctc<br>Leu | att<br>Ile<br>1530 | aag<br>Lys | gtt<br>Val | gtt<br>Val | gat<br>Asp | 4718 |
| gtg<br>Val | gag<br>Glu<br>1535 | gag<br>Glu | caa<br>Gln | cag<br>Gln | ctg<br>Leu<br>1540 | gaa<br>Glu | gag<br>Glu | tct<br>Ser | ggg<br>Gly | cca<br>Pro<br>1545 | cac<br>His | gat<br>Asp | ttg<br>Leu | acg<br>Thr | 4763 |
| gaa<br>Glu | aca<br>Thr<br>1550 | tct<br>Ser | tac<br>Tyr | ttg<br>Leu | cca<br>Pro<br>1555 | agg<br>Arg | caa<br>Gln | gat<br>Asp | cta<br>Leu | gag<br>Glu<br>1560 | gga<br>Gly | acc<br>Thr | cct<br>Pro | tac<br>Tyr | 4808 |
| ctg<br>Leu | gaa<br>Glu<br>1565 | tct<br>Ser | gga<br>Gly | atc<br>Ile | agc<br>Ser<br>1570 | ctc<br>Leu | ttc<br>Phe | tct<br>Ser | gat<br>Asp | gac<br>Asp<br>1575 | cct<br>Pro | gaa<br>Glu | tct<br>Ser | gat<br>Asp | 4853 |
| cct<br>Pro | tct<br>Ser<br>1580 | gaa<br>Glu | gac<br>Asp | aga<br>Arg | gcc<br>Ala<br>1585 | cca<br>Pro | gag<br>Glu | tca<br>Ser | gct<br>Ala | cgt<br>Arg<br>1590 | gtt<br>Val | ggc<br>Gly | aac<br>Asn | ata<br>Ile | 4898 |
| cca<br>Pro | tct<br>Ser<br>1595 | tca<br>Ser | acc<br>Thr | tct<br>Ser | gca<br>Ala<br>1600 | ttg<br>Leu | aaa<br>Lys | gtt<br>Val | ccc<br>Pro | caa<br>Gln<br>1605 | ttg<br>Leu | aaa<br>Lys | gtt<br>Val | gca<br>Ala | 4943 |
| gaa<br>Glu | tct<br>Ser<br>1610 | gcc<br>Ala | cag<br>Gln | agt<br>Ser | cca<br>Pro<br>1615 | gct<br>Ala | gct<br>Ala | gct<br>Ala | cat<br>His | act<br>Thr<br>1620 | act<br>Thr | gat<br>Asp | act<br>Thr | gct<br>Ala | 4988 |
| ggg<br>Gly | tat<br>Tyr<br>1625 | aat<br>Asn | gca<br>Ala | atg<br>Met | gaa<br>Glu<br>1630 | gaa<br>Glu | agt<br>Ser | gtg<br>Val | agc<br>Ser | agg<br>Arg<br>1635 | gag<br>Glu | aag<br>Lys | cca<br>Pro | gaa<br>Glu | 5033 |
| ttg<br>Leu | aca<br>Thr<br>1640 | gct<br>Ala | tca<br>Ser | aca<br>Thr | gaa<br>Glu<br>1645 | agg<br>Arg | gtc<br>Val | aac<br>Asn | aaa<br>Lys | aga<br>Arg<br>1650 | atg<br>Met | tcc<br>Ser | atg<br>Met | gtg<br>Val | 5078 |
| gtg<br>Val | tct<br>Ser<br>1655 | ggc<br>Gly | ctg<br>Leu | acc<br>Thr | cca<br>Pro<br>1660 | gaa<br>Glu | gaa<br>Glu | ttt<br>Phe | atg<br>Met | ctc<br>Leu<br>1665 | gtg<br>Val | tac<br>Tyr | aag<br>Lys | ttt<br>Phe | 5123 |
| gcc<br>Ala | aga<br>Arg<br>1670 | aaa<br>Lys | cac<br>His | cac<br>His | atc<br>Ile<br>1675 | act<br>Thr | tta<br>Leu | act<br>Thr | aat<br>Asn | cta<br>Leu<br>1680 | att<br>Ile | act<br>Thr | gaa<br>Glu | gag<br>Glu | 5168 |
| act<br>Thr | act<br>Thr<br>1685 | cat<br>His | gtt<br>Val | gtt<br>Val | atg<br>Met<br>1690 | aaa<br>Lys | aca<br>Thr | gat<br>Asp | gct<br>Ala | gag<br>Glu<br>1695 | ttt<br>Phe | gtg<br>Val | tgt<br>Cys | gaa<br>Glu | 5213 |
| cgg<br>Arg | aca<br>Thr<br>1700 | ctg<br>Leu | aaa<br>Lys | tat<br>Tyr | ttt<br>Phe<br>1705 | cta<br>Leu | gga<br>Gly | att<br>Ile | gcg<br>Ala | gga<br>Gly<br>1710 | gga<br>Gly | aaa<br>Lys | tgg<br>Trp | gta<br>Val | 5258 |
| gtt<br>Val | agc<br>Ser<br>1715 | tat<br>Tyr | ttc<br>Phe | tgg<br>Trp | gtg<br>Val<br>1720 | acc<br>Thr | cag<br>Gln | tct<br>Ser | att<br>Ile | aaa<br>Lys<br>1725 | gaa<br>Glu | aga<br>Arg | aaa<br>Lys | atg<br>Met | 5303 |
| ctg<br>Leu | aat<br>Asn<br>1730 | gag<br>Glu | cat<br>His | gat<br>Asp | ttt<br>Phe<br>1735 | gaa<br>Glu | gtc<br>Val | aga<br>Arg | gga<br>Gly | gat<br>Asp<br>1740 | gtg<br>Val | gtc<br>Val | aat<br>Asn | gga<br>Gly | 5348 |
| aga<br>Arg | aac<br>Asn<br>1745 | cac<br>His | caa<br>Gln | ggt<br>Gly | cca<br>Pro<br>1750 | aag<br>Lys | cga<br>Arg | gca<br>Ala | aga<br>Arg | gaa<br>Glu<br>1755 | tcc<br>Ser | cag<br>Gln | gac<br>Asp | aga<br>Arg | 5393 |
| aag<br>Lys | atc<br>Ile<br>1760 | ttc<br>Phe | agg<br>Arg | ggg<br>Gly | cta<br>Leu<br>1765 | gaa<br>Glu | atc<br>Ile | tgt<br>Cys | tgc<br>Cys | tat<br>Tyr<br>1770 | ggg<br>Gly | ccc<br>Pro | ttc<br>Phe | acc<br>Thr | 5438 |
| aac<br>Asn | atg<br>Met<br>1775 | ccc<br>Pro | aca<br>Thr | gat<br>Asp | caa<br>Gln<br>1780 | ctg<br>Leu | gaa<br>Glu | tgg<br>Trp | atg<br>Met | gta<br>Val<br>1785 | cag<br>Gln | ctg<br>Leu | tgt<br>Cys | ggt<br>Gly | 5483 |
| gct<br>Ala | tct<br>Ser | gtg<br>Val | gtg<br>Val | aag<br>Lys | gag<br>Glu | ctt<br>Leu | tca<br>Ser | tca<br>Ser | ttc<br>Phe | acc<br>Thr | ctt<br>Leu | ggc<br>Gly | aca<br>Thr | ggt<br>Gly | 5528 |

```
Ala Ser  Val Val Lys Glu Leu  Ser Ser Phe Thr Leu  Gly Thr Gly
    1790             1795              1800 gtc cac cca att gtg gtt gtg cag cca gat gcc tgg aca gag gac       5573
Val His Pro Ile Val Val Val Gln Pro Asp Ala Trp Thr Glu Asp
    1805             1810              1815 aat ggc ttc cat gca att ggg cag atg tgt gag gca cct gtg gtg       5618
Asn Gly Phe His Ala Ile Gly Gln Met Cys Glu Ala Pro Val Val
    1820             1825              1830 acc cga gag tgg gtg ttg gac agt gta gca ctc tac cag tgc cag       5663
Thr Arg Glu Trp Val Leu Asp Ser Val Ala Leu Tyr Gln Cys Gln
    1835             1840              1845 gag ctg gac acc tac ctg ata ccc cag atc ccc cac agc cac tac       5708
Glu Leu Asp Thr Tyr Leu Ile Pro Gln Ile Pro His Ser His Tyr
    1850             1855              1860 tga                                                               5711

<210> SEQ ID NO 268
<211> LENGTH: 1863
<212> TYPE: PRT
<213> ORGANISM: Homo sapiens

<400> SEQUENCE: 268

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270
```

-continued

```
Pro Cys Gly Thr Asn Thr His Ala Ser Ser Leu Gln His Glu Asn Ser
        275                 280                 285
Ser Leu Leu Thr Lys Asp Arg Met Asn Val Glu Lys Ala Glu Phe
    290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
    370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
    450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Pro Thr Ser Gly Leu
            500                 505                 510
His Pro Glu Asp Phe Ile Lys Lys Ala Asp Leu Ala Val Gln Lys Thr
        515                 520                 525
Pro Glu Met Ile Asn Gln Gly Thr Asn Gln Thr Glu Gln Asn Gly Gln
    530                 535                 540
Val Met Asn Ile Thr Asn Ser Gly His Glu Asn Lys Thr Lys Gly Asp
545                 550                 555                 560
Ser Ile Gln Asn Glu Lys Asn Pro Asn Pro Ile Glu Ser Leu Glu Lys
                565                 570                 575
Glu Ser Ala Phe Lys Thr Lys Ala Glu Pro Ile Ser Ser Ser Ile Ser
            580                 585                 590
Asn Met Glu Leu Glu Leu Asn Ile His Asn Ser Lys Ala Pro Lys Lys
        595                 600                 605
Asn Arg Leu Arg Arg Lys Ser Ser Thr Arg His Ile His Ala Leu Glu
    610                 615                 620
Leu Val Val Ser Arg Asn Leu Ser Pro Pro Asn Cys Thr Glu Leu Gln
625                 630                 635                 640
Ile Asp Ser Cys Ser Ser Ser Glu Glu Ile Lys Lys Lys Tyr Asn
                645                 650                 655
Gln Met Pro Val Arg His Ser Arg Asn Leu Gln Leu Met Glu Gly Lys
            660                 665                 670
Glu Pro Ala Thr Gly Ala Lys Lys Ser Asn Lys Pro Asn Glu Gln Thr
        675                 680                 685
```

```
Ser Lys Arg His Asp Ser Asp Thr Phe Pro Glu Leu Lys Leu Thr Asn
    690             695             700

Ala Pro Gly Ser Phe Thr Lys Cys Ser Asn Thr Ser Glu Leu Lys Glu
705             710             715                         720

Phe Val Asn Pro Ser Leu Pro Arg Glu Glu Lys Glu Glu Lys Leu Glu
                725             730             735

Thr Val Lys Val Ser Asn Asn Ala Glu Asp Pro Lys Asp Leu Met Leu
            740             745             750

Ser Gly Glu Arg Val Leu Gln Thr Glu Arg Ser Val Glu Ser Ser Ser
        755             760             765

Ile Ser Leu Val Pro Gly Thr Asp Tyr Gly Thr Gln Glu Ser Ile Ser
770             775             780

Leu Leu Glu Val Ser Thr Leu Gly Lys Ala Lys Thr Glu Pro Asn Lys
785             790             795                         800

Cys Val Ser Gln Cys Ala Ala Phe Glu Asn Pro Lys Gly Leu Ile His
                805             810             815

Gly Cys Ser Lys Asp Asn Arg Asn Asp Thr Glu Gly Phe Lys Tyr Pro
            820             825             830

Leu Gly His Glu Val Asn His Ser Arg Glu Thr Ser Ile Glu Met Glu
        835             840             845

Glu Ser Glu Leu Asp Ala Gln Tyr Leu Gln Asn Thr Phe Lys Val Ser
850             855             860

Lys Arg Gln Ser Phe Ala Leu Phe Ser Asn Pro Gly Asn Ala Glu Glu
865             870             875                         880

Glu Cys Ala Thr Phe Ser Ala His Ser Gly Ser Leu Lys Lys Gln Ser
                885             890             895

Pro Lys Val Thr Phe Glu Cys Glu Gln Lys Glu Glu Asn Gln Gly Lys
            900             905             910

Asn Glu Ser Asn Ile Lys Pro Val Gln Thr Val Asn Ile Thr Ala Gly
        915             920             925

Phe Pro Val Val Gly Gln Lys Asp Lys Pro Val Asp Asn Ala Lys Cys
930             935             940

Ser Ile Lys Gly Gly Ser Arg Phe Cys Leu Ser Ser Gln Phe Arg Gly
945             950             955                         960

Asn Glu Thr Gly Leu Ile Thr Pro Asn Lys His Gly Leu Leu Gln Asn
                965             970             975

Pro Tyr Arg Ile Pro Pro Leu Phe Pro Ile Lys Ser Phe Val Lys Thr
            980             985             990

Lys Cys Lys Lys Asn Leu Leu Glu Glu Asn Phe Glu Glu His Ser Met
        995             1000            1005

Ser Pro Glu Arg Glu Met Gly Asn Glu Asn Ile Pro Ser Thr Val
    1010            1015            1020

Ser Thr Ile Ser Arg Asn Asn Ile Arg Glu Asn Val Phe Lys Glu
    1025            1030            1035

Ala Ser Ser Ser Asn Ile Asn Glu Val Gly Ser Ser Thr Asn Glu
    1040            1045            1050

Val Gly Ser Ser Ile Asn Glu Ile Gly Ser Ser Asp Glu Asn Ile
    1055            1060            1065

Gln Ala Glu Leu Gly Arg Asn Arg Gly Pro Lys Leu Asn Ala Met
    1070            1075            1080

Leu Arg Leu Gly Val Leu Gln Pro Glu Val Tyr Lys Gln Ser Leu
    1085            1090            1095

Pro Gly Ser Asn Cys Lys His Pro Glu Ile Lys Lys Gln Glu Tyr
```

-continued

```
            1100                1105                1110
Glu Glu Val Val Gln Thr Val Asn Thr Asp Phe Ser Pro Tyr Leu
        1115                1120                1125
Ile Ser Asp Asn Leu Glu Gln Pro Met Gly Ser Ser His Ala Ser
        1130                1135                1140
Gln Val Cys Ser Glu Thr Pro Asp Asp Leu Leu Asp Asp Gly Glu
        1145                1150                1155
Ile Lys Glu Asp Thr Ser Phe Ala Glu Asn Asp Ile Lys Glu Ser
        1160                1165                1170
Ser Ala Val Phe Ser Lys Ser Val Gln Lys Gly Glu Leu Ser Arg
        1175                1180                1185
Ser Pro Ser Pro Phe Thr His Thr His Leu Ala Gln Gly Tyr Arg
        1190                1195                1200
Arg Gly Ala Lys Lys Leu Glu Ser Ser Glu Glu Asn Leu Ser Ser
        1205                1210                1215
Glu Asp Glu Glu Leu Pro Cys Phe Gln His Leu Leu Phe Gly Lys
        1220                1225                1230
Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu
        1250                1255                1260
Lys Asn Ser Leu Asn Asp Cys Ser Asn Gln Val Ile Leu Ala Lys
        1265                1270                1275
Ala Ser Gln Glu His His Leu Ser Glu Glu Thr Lys Cys Ser Ala
        1280                1285                1290
Ser Leu Phe Ser Ser Gln Cys Ser Glu Leu Glu Asp Leu Thr Ala
        1295                1300                1305
Asn Thr Asn Thr Gln Asp Pro Phe Leu Ile Gly Ser Ser Lys Gln
        1310                1315                1320
Met Arg His Gln Ser Glu Ser Gln Gly Val Gly Leu Ser Asp Lys
        1325                1330                1335
Glu Leu Val Ser Asp Asp Glu Glu Arg Gly Thr Gly Leu Glu Glu
        1340                1345                1350
Asn Asn Gln Glu Glu Gln Ser Met Asp Ser Asn Leu Gly Glu Ala
        1355                1360                1365
Ala Ser Gly Cys Glu Ser Glu Thr Ser Val Ser Glu Asp Cys Ser
        1370                1375                1380
Gly Leu Ser Ser Gln Ser Asp Ile Leu Thr Thr Gln Gln Arg Asp
        1385                1390                1395
Thr Met Gln His Asn Leu Ile Lys Leu Gln Gln Glu Met Ala Glu
        1400                1405                1410
Leu Glu Ala Val Leu Glu Gln His Gly Ser Gln Pro Ser Asn Ser
        1415                1420                1425
Tyr Pro Ser Ile Ile Ser Asp Ser Ser Ala Leu Glu Asp Leu Arg
        1430                1435                1440
Asn Pro Glu Gln Ser Thr Ser Glu Lys Ala Val Leu Thr Ser Gln
        1445                1450                1455
Lys Ser Ser Glu Tyr Pro Ile Ser Gln Asn Pro Glu Gly Leu Ser
        1460                1465                1470
Ala Asp Lys Phe Glu Val Ser Ala Asp Ser Ser Thr Ser Lys Asn
        1475                1480                1485
Lys Glu Pro Gly Val Glu Arg Ser Ser Pro Ser Lys Cys Pro Ser
        1490                1495                1500
```

-continued

```
Leu Asp Asp Arg Trp Tyr Met His Ser Cys Ser Gly Ser Leu Gln
    1505                1510                1515
Asn Arg Asn Tyr Pro Ser Gln Glu Glu Leu Ile Lys Val Val Asp
    1520                1525                1530
Val Glu Glu Gln Gln Leu Glu Glu Ser Gly Pro His Asp Leu Thr
    1535                1540                1545
Glu Thr Ser Tyr Leu Pro Arg Gln Asp Leu Glu Gly Thr Pro Tyr
    1550                1555                1560
Leu Glu Ser Gly Ile Ser Leu Phe Ser Asp Asp Pro Glu Ser Asp
    1565                1570                1575
Pro Ser Glu Asp Arg Ala Pro Glu Ser Ala Arg Val Gly Asn Ile
    1580                1585                1590
Pro Ser Ser Thr Ser Ala Leu Lys Val Pro Gln Leu Lys Val Ala
    1595                1600                1605
Glu Ser Ala Gln Ser Pro Ala Ala Ala His Thr Thr Asp Thr Ala
    1610                1615                1620
Gly Tyr Asn Ala Met Glu Glu Ser Val Ser Arg Glu Lys Pro Glu
    1625                1630                1635
Leu Thr Ala Ser Thr Glu Arg Val Asn Lys Arg Met Ser Met Val
    1640                1645                1650
Val Ser Gly Leu Thr Pro Glu Glu Phe Met Leu Val Tyr Lys Phe
    1655                1660                1665
Ala Arg Lys His His Ile Thr Leu Thr Asn Leu Ile Thr Glu Glu
    1670                1675                1680
Thr Thr His Val Val Met Lys Thr Asp Ala Glu Phe Val Cys Glu
    1685                1690                1695
Arg Thr Leu Lys Tyr Phe Leu Gly Ile Ala Gly Gly Lys Trp Val
    1700                1705                1710
Val Ser Tyr Phe Trp Val Thr Gln Ser Ile Lys Glu Arg Lys Met
    1715                1720                1725
Leu Asn Glu His Asp Phe Glu Val Arg Gly Asp Val Val Asn Gly
    1730                1735                1740
Arg Asn His Gln Gly Pro Lys Arg Ala Arg Glu Ser Gln Asp Arg
    1745                1750                1755
Lys Ile Phe Arg Gly Leu Glu Ile Cys Cys Tyr Gly Pro Phe Thr
    1760                1765                1770
Asn Met Pro Thr Asp Gln Leu Glu Trp Met Val Gln Leu Cys Gly
    1775                1780                1785
Ala Ser Val Val Lys Glu Leu Ser Ser Phe Thr Leu Gly Thr Gly
    1790                1795                1800
Val His Pro Ile Val Val Val Gln Pro Asp Ala Trp Thr Glu Asp
    1805                1810                1815
Asn Gly Phe His Ala Ile Gly Gln Met Cys Glu Ala Pro Val Val
    1820                1825                1830
Thr Arg Glu Trp Val Leu Asp Ser Val Ala Leu Tyr Gln Cys Gln
    1835                1840                1845
Glu Leu Asp Thr Tyr Leu Ile Pro Gln Ile Pro His Ser His Tyr
    1850                1855                1860
```

METHOD FOR DETERMINING THE HAPLOTYPE OF A HUMAN BRCA1 GENE

This application is a continuation-in-part of U.S. application Ser. No. 08/905,772 filed Aug. 4, 1997 now abandoned, which is a continuation-in-part of U.S. application Ser. No. 08/798,691 filed Feb. 12, 1997 now U.S. Pat. No. 5,750,400 issued May 12, 1998, which is a continuation-in-part of U.S. application Ser. No. 08/598,591 filed now Feb. 12, 1996 U.S. Pat. No. 5,654,155 issued Aug. 5, 1997. This application is also a continuation-in-part of U.S. application Ser. No. 09/084,471 filed May 22, 1998, each of which is hereby incorporated by reference in its entirety.

FIELD OF THE INVENTION

The invention relates to methods for identifying functional alleles commonly occurring in a population, for finding new functional alleles, for determining the relative frequencies at which such alleles, for genetic and pharmacogenetic applications of the methods and products produced thereby.

BACKGROUND OF THE INVENTION

An increasing number of genes which play a role in many different diseases are being identified. Detection of mutations in such genes is instrumental in determining susceptibility to or diagnosing these diseases. Some diseases, such as sickle cell disease, are known to be monomorphic; i.e., the disease is generally caused by a single mutation present in the population. In such cases where one or only a few known mutations are responsible for the disease, methods for detecting the mutations are targeted to the site within the gene at which they are known to occur. However, the mutation responsible for such a monomorphic disease can only be established in the first instance if there exists an accurate reference sequence for the non-pathological state.

In many other cases individuals affected by a given disease display extensive allelic heterogeneity. For example, more than 125 mutations in the human BRCA1 gene have been reported (Breast Cancer Information Core world wide web site at http://www.nchgr.nih.gov/dir/lab_transfer/bic, which became publicly available on Nov. 1, 1995; Friend, S. et al., 1995, Nature Genetics 11:238). Mutations in the BRCA1 gene are thought to account for roughly 45% of inherited breast cancer and 80–90% of families with increased risk of early onset breast and ovarian cancer (Easton, 1993, et al., American Journal of Human Genetics 52: 678–701).

Other examples of genes for which the population displays extensive allelic heterogeneity and which have been implicated in disease include CFTR (cystic fibrosis), dystrophin (Duchenne muscular dystrophy, and Becker muscular dystrophy), and p53 (Li-Fraumeni syndrome).

Breast cancer is also an example of a disease in which, in addition to allelic heterogeneity, there is genetic heterogeneity. In addition to BRCA1, the BRCA2 and BRCA3 genes have been linked to breast cancer. Similarly, the NFI and NFII genes are involved in neurofibromatosis (types I and II, respectively). Furthermore, hereditary non-polyposis colorectal cancer (HNPCC) is a disease in which four genes, MSH2, MLH1, PMS1, and PMS2, have been implicated. It is yet another example of a disease in which there is both allelic and genetic heterogeneity of mutations. A cDNA sequence for MSH2 has been deposited in GenBank as Accession No. U03911; and a cDNA sequence for MLH1 has been deposited in GenBank as Accession No. U40978.

Additionally, disease or disease susceptibility also results from the interaction of more than one gene or the interaction of an environmental, chemical or biological influence on one or more genes. For example, measles virus infects many people; some are immune due to vaccination or previous infection, some are infected but asymptomatic, some become sick with a rash, some develop an encephalitis and some die. Genetic susceptibility and many other factors are involved in the outcome.

A common misconception in the field of molecular genetics is that for any given gene there exists a single "normal" or "wild-type" sequence. Often, research into such wild-type sequences ends once a single sequence associated with normal function is identified. For example, information in GenBank concerning the BRCA1 sequence represented by GenBank Accession No. U14680 does not indicate a basis for whether this sequence is representative of the population at large. Even when polymorphisms of the BRCA1 gene were identified, no analysis was provided of the arrangement of such sequence variations in a given allele (i.e., the haplotype) (Miki et al., 1994, Science 266: 66–71).

In the fields of plant and animal breeding, the "wild-type" may not be the desirable or may be one of several possibilities. For some domesticated plants and animals, the "wild-type" of any gene may not even be known. In the Brassica family, debate exists as to exactly what is a wild cabbage plant, much less which of the many genes or traits constitutes a "wild-type". By definition, a wild-type is not pathological but sometimes this definition seems inappropriate. For example, the MacIntosh apple is propagated asexually exclusively. An inability to reproduce naturally may be considered the result of pathological mutation(s) but is none the less the desired trait. In other situations, different strains of a plant are cross-breed where each set of genes from each parent strain may be considered "wild-type".

Identification of a mutation provides for early diagnosis which is essential for effective treatment of many diseases. However, in order to identify a mutation, it is necessary to have an accurate understanding of the proper reference sequences which encode the non-pathological functional gene products occurring in the population. Prior research efforts and publications have neither suggested nor taught a systematic approach to both identify a functional allele of a given gene and determine the relative frequency with which the allele occurs in the population.

Certain wild-type sequences of a gene may be otherwise indistinguishable from others except under certain circumstances. For example, a gene involved in resistance or susceptibility to a certain infectious agent is only recognized when the individual plant or animal is exposed to the infectious agent. Likewise chemical sensitivity may be a wild-type which is pathological under only certain circumstances which may never occur in the individual. Drought tolerance traits are significant only under environmental stress which may or may not occur. Therefore, the type of wild-type sequence is of importance.

SUMMARY OF THE INVENTION

It is an object of the invention to provide an integrated, systematic process for determining the functional allele profile for a given gene in a population. In accordance with the invention, a functional allele profile contains 1) the identity of the key functional allele or alleles for a given gene in the population, including the "consensus" sequence, and 2) the relative frequency with which these functional alleles occur in the population. Thus, the functional allele profile includes the identification of the consensus normal sequence, i.e., the most commonly occurring functional allele.

The present invention, therefore, provides a normal sequence which is the most likely sequence to be found in the majority of the normal population, the (i.e., "consensus normal DNA sequence"). A consensus normal allele sequence of a gene more accurately reflects the most likely sequence to be found in the population. Determining the consensus sequence is useful in both the diagnosis and treatment of disease. For example, use of the consensus normal gene sequence reduces the likelihood of misinterpreting a "sequence variation" found in the normal population with a pathologic "mutation" (i.e. causes disease in the individual or puts the individual at a high risk of developing the disease). A consensus normal DNA sequence makes it possible for true pathological mutations to be easily identified or differentiated from polymorphisms.

With large interest in mutation and polymorphism testing such as cancer predisposition testing, misinterpretation of sequence data is a particular concern. Individuals diagnosed with cancer want to know their prognosis and whether their disease is caused by a heritable genetic mutation. Likewise for other disease and traits and those who manage or manipulate these traits. Relatives of those with cancer who have not yet been diagnosed with the disease are also concerned whether they carry such a heritable mutation. Carrying such a mutation may increase risk of contracting the disease sufficiently to warrant an aggressive surveillance program. Accurate and efficient identification of mutations in genes linked to disease is crucial for widespread diagnostic screening for hereditary diseases.

In addition, the consensus sequence, or other sequences identified in the functional allele profile, allow for the selection of therapeutically optimal nucleotide sequences to be administered in gene therapy or gene replacement, or optimal amino acid sequence in the therapeutic administration of active proteins or peptides. The consensus sequence is generally the easiest target for various agonists, antagonists and measuring interactions with the gene or expression product appropriate for pharmacogenetic analysis.

Moreover, determining a functional allele profile of genes allows for an evaluation of the degree to which the gene is under selective pressure.

It is another embodiment of the present invention to find a new allele having a different wild-type haplotype from that previously known.

It is another embodiment of the present invention to determine the haplotype of a sample by determining the polymorphisms constituting the haplotype. Such a technique applies to one and plural genes, especially genes which interact or express products which interact with each other directly, interact with the same or similar other compound or are along the same metabolic pathway. As such, the method of the present invention determines combinations of haplotypes in different genes.

It is another embodiment of the present invention is determining how an individual will react to a particular chemical, environmental or biological influence. It is a premise of the present invention that different wild-type genes or their expression products interact differently in some circumstances.

Another embodiment of the present invention is the determination of traits and susceptibilities of plants and animals during breeding experiments by detecting the polymorphisms constituting the gene haplotype associated with the trait or susceptibility of interest.

BRIEF DESCRIPTION OF THE FIGURE

FIG. 1 shows alternative alleles containing polymorphic (non-mutation causing variations) sites along the BRCA1 gene, represented as individual "haplotypes" of the BRCA1 gene. The alternative allelic variations occurring at nucleotide positions 2201, 2430, 2731, 3232, 3667, 4427, and 4956 are shown. The BRCA1$^{(omi1)}$ haplotype (SEQ ID NO: 263) is indicated with dark shading. For comparison, the haplotype available in GenBank is completely unshaded and designated as "GB". Two additional haplotypes (BRCA1$^{(omi2)}$ haplotype (SEQ ID NO: 265) and BRCA1 $^{(omi3)}$ haplotype (SEQ ID NO: 267) are represented with mixed shaded and unshaded positions, numbers 7 and 9 from left to right).

DETAILED DESCRIPTION OF THE INVENTION

Figure 1:
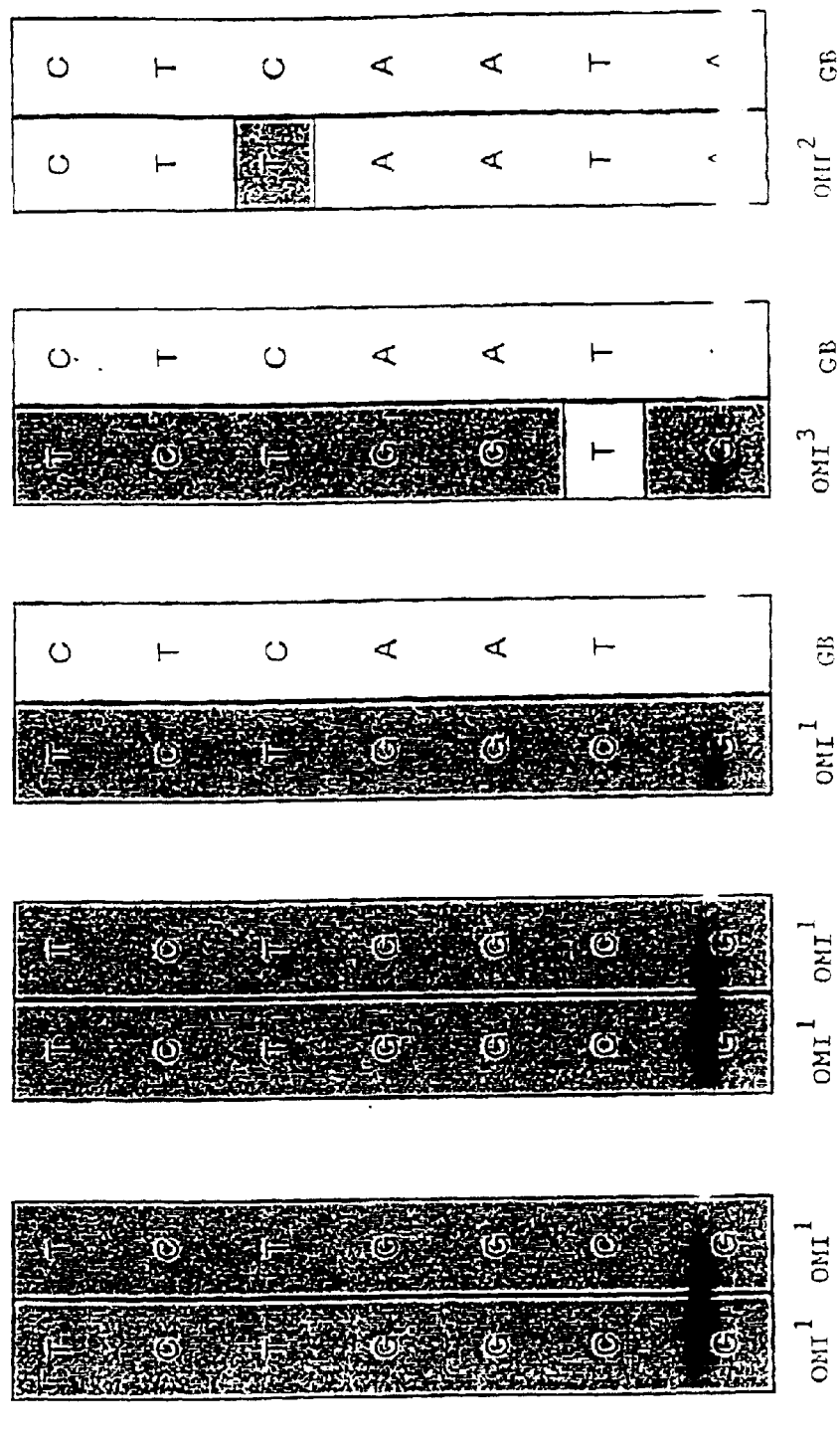
FIG. 1.

The invention provides an integrated, systematic process for determining the functional allele profile for a given gene or combination of genes in a population. In accordance with the invention, a functional allele profile contains 1) the identity of the key functional allele or alleles for a given gene in the population, including the "consensus" sequence, and 2) the relative frequency with which these functional alleles occur in the population. Thus, the functional allele profile includes the identification of the consensus normal sequence, i.e., the most commonly occurring functional allele.

The present invention, therefore, provides a normal sequence which is the most likely sequence to be found in the majority of the normal population, the (i.e., "consensus normal DNA sequence"). A consensus normal allele sequence of a gene more accurately reflects the most likely sequence to be found in the population. In the process for determining functional alleles or afterward, one may search for and discover or synthesize a heretofor unknown or "new" allele.

A functional allele profile can be determined for any gene in which an altered or deficient function produces a recognizable, phenotypic trait, including, but not limited to, pathology. The invention is set forth for the purpose of illustration, and not by way of limitation, for determining the functional allele profile of three different genes associated with disease—for example, the MSH2 and MLH1 genes, each associated with hereditary non-polyposis colorectal cancer (HNPCC), and the BRCA1 gene, associated with breast, ovarian, prostate and other cancers.

The following terms as used herein are defined as follows:

"Allele" refers to an alternative version (i.e., nucleotide sequence) of a gene or DNA sequence at a specific chromosomal locus.

"Allelic variation" or "sequence variation" refers to a particular alternative nucleotide or nucleotide sequence at a position within a gene (e.g., a polymorphic site or mutation) whose sequence varies from one allele to another.

"Coding sequence" or "DNA coding sequence" refers to those portions of a gene which, taken together, code for a peptide (protein), or which nucleic acid itself has function.

"Composite genomic sequence" refers to the combination of the two allelic nucleotide sequences (i.e., maternal and paternal) obtained from sequencing a diploid genomic sample.

"Consensus" refers to the most commonly occurring in the population.

"Functional allele" refers to an allele which is naturally transcribed and translated into a functioning protein.

"Functional Allele Profile" refers to a set of functional alleles which are representative of the most common alleles occurring in a population, wherein the functional alleles are identified by nucleotide sequence and the relative frequencies with which the functional alleles occur in the population.

"Haplotype" refers to a set of nucleotides or nucleotide sequences occurring at sites of allelic variation occurring within a locus on a single chromosome (of either maternal or paternal origin). The "locus" includes the entire coding sequence.

"Mutation" refers to a base change or a gain or loss of base pair(s) in a DNA sequence, which results in a DNA sequence which codes for a non-functioning protein or a protein with substantially reduced or altered function.

"Agent for polymerization" refers to an enzyme which may be heat stable, e.g. Taq polymerase, or function at lower temperatures, e.g., room temperature, that effects an extension of DNA from a short primer sequence annealed to the target DNA of interest.

"Polymorphism" refers to an allelic variation which occurs in greater than or equal to 1% of the normal healthy population.

"Single nucleotide polymorphism" (SNP) refers to an allelic variation which is defined by two (and only two) alternative bases found at a specific and particular nucleotide in genomic DNA. It may be within a gene (i.e., exonic or intronic) or outside of a gene (such as in a promoter or other regulatory structure) or lastly found between genes.

"Individual" refers to a single organism which may be human, plant or non-human animal. The individual may be intact or a biological sample taken from the individual which contains sufficient substances or information regarding the individual.

"Protein variant" and "variant amino acid sequence" refers to different amino acid sequences from that in one naturally occurring wild-type protein and is generally considered the same protein. Some different haplotypes have variant amino acid sequences.

"Expression product" refers to an RNA, spliced or unspliced, a pre-, pro-, prepro- or a peptide which alone or in conjunction with other peptides constitutes a protein.

"Pharmaceutical" refers to any bio-effecting chemical drug or biological agent which alters or induces an alteration in the metabolism of an "individual". Pharmaceuticals include compositions for use on veternary animals and agricultural and ornamental plants.

"Trait" refers to a phenotypically determinable characteristic resulting from the influence of one or more genes, alone or in conjunction with an environmental condition or exposure to other agents. Traits include susceptibilities to chemicals, infectious agents and environmental conditions (temperature, drought etc.).

Utility of the Invention

A person skilled in the art of genetic testing will find the present invention useful for diagnosis and treatment of diseases and susceptibility thereto. The invention is especially useful for establishing the "standard" (i.e., consensus normal DNA sequence) and new haplotypes for clinical diagnostic, therapeutic, genetic testing and breeding uses.

Diagnostics

The diagnostic applications for which determining a functional allele profile in accordance with the invention include, but are not limited to, the following:

a) identifying individuals having a gene with no coding mutations, which individuals are therefore not at risk or have no increased susceptibility to the pathology(s) associated with a mutation in the gene in question;

b) avoiding misinterpretation of functional polymorphisms detected in the gene as mutations;

c) identifying individuals having a potentially abnormal gene that does not match the Consensus Normal DNA sequence;

d) determining ethnic founder haplotypes so that clinical analysis is appropriate for an individual from this ethnic group;

e) determining a sequence under strongest selective pressure; and f) determining an amino acid and/or short nucleic acid sequence which may be derived from the consensus normal DNA sequence to make diagnostic and probes antibodies. Labeled diagnostic probes may be used by any hybridization method to determine the level of protein in serum or lysed cell suspension of a patient, or solid surface cell sample such as for immunohistochemical analysis.

g) detecting a new haplotype and determining the polymorphisms constituting the new haplotype.

h) detecting a new protein variant type and determining the variant amino acids constituting the new protein variant.

i) determining the combination of one haplotype or polymorphism for one gene and the haplotype or polymorphism for another different gene in the same individual. Generally, the genes or their expression products interact with each other directly, e.g. bind to each other, or indirectly by functioning with each other on the same substrate, are in different stages in a metabolic pathway, or are related to the same disease, susceptibility, condition or trait.

j) determining whether to administer a bioeffecting composition to an individual wherein individuals with different haplotypes for one or more genes respond differently to the composition.

k) determining susceptibility to disease or other pathology to decide on prophylaxis, therapy or differential monitoring.

l) determining a trait by quick assay of a genetic engineered or selectively bred individual. This permits one to determine the trait without actually measuring the trait phenotypically.

m) developing probe chips and panels of allele-specific oligonucleotide(s) to assay for the haplotypes or polymorphisms in one or more genes.

Therapeutics

Certain "normal" alleles may be more functional or hyper-functional than the minimum needed to maintain a normal phenotype in an individual, particularly when stressed. By determining the most common allele in a population one may be observing empiric data for such suitability for survival (the effects may be so subtle that scientists have not determined the basis of this selection). For example, alleles with longer mRNA or protein half-lives (i.e., stability) may produce healthier cells, and, thus, healthier people. Conversely, there may also be a selective advantage to a very short RNA half-life such as in proteins involved in the cell cycle pathway. Furthermore, proteases are known to have favored cutting sites which may be present or absent in different normal alleles leading to peptides that have intrinsic activity themselves.

Thus the determination of the functional allele profile or a new functional allele in accordance with the invention is useful in clinical therapy for:
 a) selecting optimal alleles for performing gene repair or gene therapy; and
 b) selecting optimal amino acid sequence for administration of functional protein in treatment or prevention of diseases.

Evolution and Population Genetics Analysis

The determination of the functional allele profile or a new functional allele in accordance with the invention is useful for:
 a) determining whether a particular gene is under strong selective pressure; and
 b) determining which of two or more genes which encode proteins with similar functions represents a redundant, or back-up copy of the gene.

Stepwise Process for Determining Functional Allele Profile

For the purpose of illustration, and not by way of limitation, the invention is described below for determining the functional allele profile of three cancer genes. However, the same principles can be applied in accordance with the invention to any gene in which a sequence variation results in a phenotypic trait, in any population within any species.

Screening for Individuals with Functional Allele Phenotype

In accordance with the invention, a group of individuals determined to be at low risk for carrying a mutation in the gene of interest is used as a source for genetic material. Any standard method known in the art for performing pedigree analysis can be used for this selection process. See, for example, Harper, P. S., *Practical Genetic Counseling*, 3d. ed., 1988 (Wright/Butterworth & Co. Ltd.: Boston), especially at pages 4–7. For example, individuals can be screened in order to identify those with no disease history in their immediate family, i.e., among their first and second degree relatives. A first degree relative is a parent, sibling, or offspring. A second degree relative is an aunt, uncle, grandparent, grandchild, niece, nephew, or half-sibling.

In a preferred embodiment for when a functional allele profile of an autosomal dominant disorder with relatively high penetrance (e.g., greater than 50%) is desired, each person is asked to fill out a hereditary cancer prescreening questionnaire. More preferably, when an autosomal dominant cancer gene with such relatively high penetrance is the gene of interest, the questionnaire set forth in Table 1, below, is used.

TABLE 1

Hereditary Cancer Pre-Screening Questionnaire

Part A: Answer the following questions about your family

1. To your knowledge, has anyone in your family been diagnosed with a very specific hereditary colon disease called Familial Adenomatous Polyposis (FAP)?
2. To your knowledge, have you or any aunt had breast cancer diagnosed before the age 35?
3. Have you had Inflammatory Bowel Disease, also called Crohn's Disease or Ulcerative Colitis, for more than 7 years?

Part B: Refer to the list of cancers below for your responses only to questions in Part B Bladder Cancer, Lung Cancer, Pancreatic Cancer, Breast Cancer, Gastric Cancer, Prostate Cancer, Colon Cancer, Malignant Melanoma, Renal Cancer, Endometrial Cancer, Ovarian Cancer, Thyroid Cancer 4. Have your mother or father, your sisters or brothers or your children had any of the listed cancers?
5. Have there been diagnosed in your mother's brothers or sisters, or your mother's parents more than one of the cancers in the above list?
6. Have there been diagnosed in your father's brothers or sisters, or your father's parents more than one of the cancers in the above list?

Part C: Refer to the list of relatives below for responses only to questions in Part C You, Your mother, Your sisters or brothers, Your mothers's sisters or brothers (maternal aunts and uncles), Your children, Your mother's parents (maternal grandparents)

7. Have there been diagnosed in these relatives 2 or more identical types of cancer? Do not count "simple" skin cancer, also called basal cell or squamous cell skin cancer.
8. Is there a total of 4 or more of any cancers in the list of relatives above other than "simple" skin cancers?

Part D: Refer to the list of relatives below for responses only to questions in Part D.

You, Your father, Your sisters or brothers, Your fathers's sisters or brothers (paternal aunts and uncles)
Your children, Your father's parents (paternal grandparents)

9. Have there been diagnosed in these relatives 2 or more identical types of cancer? Do not count "simple" skin cancer, also called basal cell or squamous cell skin cancer.
10. Is there a total of 4 or more of any cancers in the list of relatives above other than "simple" skin cancers?

© Copyright 1996, OncorMed, Inc.

Individuals who answer no to all questions in Table 1 are sesignated as low risk of being carriers of mutations in the gene of interest and, therefore, in accordance with the invention, are candidates for further analysis set forth below.

Sequencing

From the group of individuals determined to have a low risk of being carriers for a mutant allele of the gene of interest, a group is selected for genomic DNA sequence analysis. Any number of samples may be analyzed. Preferably, a number of samples which is small enough for convenient, accurate sequence analysis, but large enough to provide a reliable representation of the population is analyzed. Most preferably, initial sequencing may be performed on ten different chromosomes by analyzing samples from five unrelated individuals.

Preferably, sequencing template is obtained by amplifying the coding region and optionally one or more related sequences (e.g. splice site junctions, enhancers, introns, promotors and other regulatory elements) of the gene of interest. Any nucleic acid specimen, in purified or non-purified form, can be utilized as the starting nucleic acid or acids, providing it contains, or is suspected of containing, the specific nucleic acid sequence containing a polymorphic locus. Thus, the process may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

While the primer pairs used are greater than required to amplify the particular polymorphisms, the primer set actually used is listed below. For larger scale testing of polymorphisms for haplotype determination, only the primer pairs actually amplifying the polymorphism are required. Additionally, primers which amplify a shorter region, as short as the one nucleotide polymorphism may be used.

When a gene containing exons is analyzed, preferably the exonic sequences are individually amplified from genomic template DNA using a pair of primers specific for the intronic regions proximally bordering each individual exon.

DNA utilized herein may be extracted from a body sample, such as blood, tissue material and the like by a variety of techniques such as that described by Maniatis, et. al. in *Molecular Cloning: A Laboratory Manual*, Cold Spring Harbor, N.Y., pp. 280–281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The primers used to carry out this invention embrace oligonucleotides of sufficient length and appropriate sequence to provide initiation of polymerization. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters*, 22:1859–1862, (1981). One method for synthesizing oligonucleotides on a modified solid support is described in U.S. Pat. No. 4,458,066.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. Amplification is described in PCR. A Practical Approach, ILR Press, Eds. M. J. McPherson, P. Quirke, and G. R. Taylor, 1992.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, (1985)), allele-specific oligonucleotide (ASO) probe analysis (Conner, et al., Proc. Natl. Acad. Sci. U.S.A., 80:278, (1983)), oligonucleotide ligation assays (OLAs) (Landgren, et al., Science, 241:1007, (1988)), heteroduplex analysis, chromatographic separation and the like. Molecular techniques for DNA analysis have been reviewed (Landgren, et al., Science, 242:229–237, (1988)).

Preferably, the method of amplifying is by PCR, as described herein and as is commonly used by those of ordinary skill in the art. Alternative methods of amplification have been described and can also be employed as long as the genetic locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. Another amplification system useful in the method of the invention is the QB Replicase System. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking DNA repair. Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling.

Another method is a process for amplifying nucleic acid sequences from a DNA or RNA template which may be purified or may exist in a mixture of nucleic acids. The resulting nucleic acid sequences may be exact copies of the template, or may be modified. The process has advantages over PCR in that it increases the fidelity of copying a specific nucleic acid sequence, and it allows one to more efficiently detect a particular point mutation in a single assay. A target nucleic acid is amplified enzymatically while avoiding strand displacement. Three primers are used. A first primer is complementary to the first end of the target. A second primer is complementary to the second end of the target. A third primer which is similar to the first end of the target and which is substantially complementary to at least a portion of the first primer such that when the third primer is hybridized to the first primer, the position of the third primer complementary to the base at the 5' end of the first primer contains a modification which substantially avoids strand displacement. This method is detailed in U.S. Pat. No. 5,593,840 to Bhatnagar et al., 1997. Although PCR is the preferred method of amplification if the invention, these other methods can also be used to amplify the gene of interest.

A number of methods well-known in the art can be used to carry out the sequencing reactions. Preferably, enzymatic sequencing based on the Sanger dideoxy method is used. Mass spectroscopy may also be used.

The sequencing reactions can be analyzed using methods well-known in the art, such as polyacrylamide gel electrophoresis. In a preferred embodiment for efficiently processing multiple samples, the sequencing reactions are carried out and analyzed using a fluorescent automated sequencing system such as the Applied Biosystems, Inc. ("ABI", Foster City, Calif.) system. For example, PCR products serving as templates are fluorescently labeled using the Taq Dye Terminator® Kit (Perkin-Elmer cat#401628). Dideoxy DNA sequencing is performed in both forward and reverse directions on an ABI automated Model 377® sequencer. The resulting data can be analyzed using "Sequence Navigator®" software available through ABI.

Alternatively, large numbers of samples can be prepared for and analyzed by capillary electrophoresis, as described, for example, in Yeung et al., U.S. Pat. No. 5,498,324.

Initial and Companion Haplotype Determination

The functional allele profiles identified in accordance with the invention may contain different alleles. Furthermore, each allele may contain multiple allelic variations, such as multiple polymorphisms. In other words, two different alleles may differ in sequence from one another at multiple nucleotide positions. Moreover, two such multiply polymorphic alleles may be present in the same individual, i.e., a heterozygote. When the genomic sample of the gene of such a heterozygous individual is sequenced, the variations at each position can be detected. They are the alternative sequences present at particular positions in the composite sequence obtained from the diploid genome. However, at this stage, which variations are grouped together in each individual haplotype or allele, i.e., the phase of the variations, cannot be determined.

For example, genomic sequence analysis of a hypothetical gene from a heterozygous individual may reveal that polymorphic positions 1, 2, or 3 each contain either an A or a G. However, it cannot be determined from this information alone whether the variations are distributed between the two alleles as:

allele 1=$A_1A_2A_3$ and allele 2=$G_1G_2G_3$; or
allele 1=$A_1A_2G_3$ and allele 2=$G_1G_2A_3$; or
allele 1=$A_1G_2G_3$ and allele 2=$G_1A_2A_3$, etc.

In accordance with the invention, such heterozygous genomic sequences obtained for the purpose of determining a functional allele profile are compared to an initial haplotype sequence. Some haplotypes can also be determined upon sequencing chromosomal samples from a homozygous individual according to the methods above. Such homozygous sequence analyses contain no ambiguities in sequence between the two alleles because they are identical.

Preferably, an initial haplotype sequence is obtained by determining the cDNA sequence of an individual identified as being at low risk for carrying a mutation as described above. Because the full-length of a cDNA of the gene of interest is derived from a single mRNA transcript, it contains the allelic variations of a single haplotype. It contains all of the allelic variations present in a single allele of the individual from which it was obtained. Thus, the cDNA sequence contains half of the allelic variations present in the composite genomic sequence of a heterozygous individual containing that allele. Moreover, unlike sequence information from a heterozygous chromosomal sample, such cDNA sequence indicates which of the allelic variations are grouped together in one allele, i.e., the phase of the variations.

By determining an initial haplotype, the companion haplotype present in a heterozygote can be determined by subtracting this sequence from the composite genomic sequence. For example, if in the illustration set forth above, the cDNA sequenced has an A in position 1, a G in position 2 and an A in position 3, then the initial haplotype is $A_1G_2A_3$. This sequence is then subtracted from the composite genomic sequence to yield the companion haplotype, namely $G_1A_2G_3$.

In general, the initial haplotype identified in a given individual also can be used to determine the presence of the haplotype in other individuals by comparing the initial haplotype sequence to the composite genomic sequence from such other individuals. When the number of allelic variations detected within a gene is four or greater, and especially when the number of allelic variations is five or greater, this method of subtracting the initial haplotype sequence from the composite genomic sequence of other individuals readily provides recognizably distinct haplotypes which are independent of each other. See, for example, the OMI[1] and GB haplotypes in FIG. 1, which differ from each other in each of seven sites of allelic variation.

When a haplotype determined in one individual is used to determine the haplotypes present in the composite genomic sequence of other individuals, the presence of that particular haplotype, and its companion haplotype as determined by subtraction from a composite genomic sequence, should be confirmed. Such confirmation of the occurrence of a given haplotype in the population can be carried out, for example, by 1) sequencing cDNA samples, as described in this section, from such other heterozygous individuals; or 2) identifying individuals homozygous for the haplotype either among the initial set of sequenced chromosomal samples or by additional confirmatory sequencing of chromosomal samples as described below.

If an initial haplotype is not represented in any heterozygous composite genomic sequences obtained, one or more additional haplotypes should be obtained from such a heterozygous individual or from different individuals screened as above.

cDNA sequences for determining the initial haplotype can be obtained using standard techniques well known in the art. First, mRNA is isolated from an individual, for example, from blood or skin cells. The mRNA is initially reversed-transcribed into double stranded cDNA and then amplified according to the well known technique of RT-PCR (see, for example, U.S. Pat. No. 5,561,058 by Gelfand et al.).

The resulting cDNA, whose sequence represents a single haplotype, can be sequenced according to the methods above.

Determining the Relative Frequencies of the Haplotype

After all haplotypes have been identified in the study population, their relative frequencies are determined. For example, if five chromosomes out of a total of ten chromosomes are of one haplotype, then its frequency is 50%. Subsequently, each haplotype is ranked in order from the most frequent to the least frequent to yield the functional allele profile.

Confirmatory Analysis of Additional Samples

As described above, initial sequence analysis is performed on a small group of individuals, most preferably five individuals, screened according to the methods described above.

After identifying the haplotypes and determining their relative frequencies among the initial set of alleles analyzed, it may be desirable, in accordance with the invention, to perform follow-up, confirmatory sequencing on additional individuals who are also screened according to the methods described above. Confirmatory sequencing can be carried out as above.

The haplotypes found occurring in the population are used as references to interpret the haplotypes present in any heterozygous individuals encountered during the confirmatory sequencing analysis of additional individuals.

By sequencing such additional samples, additional data points can be added to the functional allele profile to provide more precise frequencies of occurrence of each allele in the population. Furthermore, additional samples may contain a new functional allele with a new haplotype. This is particularly likely to be found for uncommon (<10%) or rare (<1%) haplotypes.

Furthermore, confirmatory sequence analysis ensures that the haplotypes determined by subtracting an initial haplotype from a composite heterozygous sequence is indeed represented in the population. Such techniques may also be used when multiple common haplotypes exist for the gene and it is uncertain which to use for subtraction.

When no sequence variation is found in the initial set of chromosomes, this indicates that the polymorphism rate of the gene of interest is uncommon (e.g., polymorphisms occur in <10% of the alleles in the population studied). In such situations, identification of uncommon alleles and determination of their frequencies requires a confirmatory sequence analysis of samples from additional individuals. This method was used to detect such an uncommon polymorphism in exon 8 of the MLH1 gene, in Example 2 below.

Such confirmatory sequencing analysis also resulted in the identification and determination of relative frequency of occurrence of polymorphisms in intronic sequences, bordering exonic regions, of both the MSH2 and MLH1 genes, as detailed in Examples 1 and 2, respectively, below. The invention is illustrated by way of the Examples below.

EXAMPLE 1

Determining the Functional Allele Profile for MSH2

Approximately 150 volunteers are screened in order to identify individuals with no cancer history in their immediate family (i.e. first and second degree relatives). Each person is asked to fill out the hereditary cancer prescreening questionnaire shown in Table 1, above. A first degree relative is a parent, sibling, or offspring. A second degree relative is an aunt, uncle, grandparent, grandchild, niece, nephew, or half-sibling. Among those individuals who answered "no" to all questions, five individuals are randomly chosen for end-to-end sequencing of their MSH2 gene.

Genomic DNA (100 nanograms) is extracted from white blood cells of five individuals designated as low risk of being carriers of mutations in the MSH2 gene from analysis of their answers to the questionnaire set forth in Table 1 above. The MSH2 coding region in each of the five samples is sequenced end-to-end by amplifying each exon individually. Each sample is amplified in a final volume of 25 microliters containing 1 microliter (100 nanograms) genomic DNA, 2.5 microliters 10×PCR buffer (100 mM Tris, pH 8.3, 500 mM KCl, 1.2 mM MgCl$_2$), 2.5 microliters 10×dNTP mix (2 mM each nucleotide), 2.5 microliters forward primer, 2.5 microliters reverse primer, and 1 microliter Taq polymerase (5 units), and 13 microliters of water.

The primers in Table 2, below, are used to carry out amplification of the various sections of the MSH2 gene samples. The primers are synthesized on an DNA/RNA Synthesizer Model 394®.

TABLE 2

MSH2 PRIMER SEQUENCES

| Exon | Primer | Sequence | |
|---|---|---|---|
| 1 | MSH1F-1 | 5'-CGC GTC TGC TTA TGA TTG G-3' | (SEQ ID NO: 1) |
|   | MSH1R-1 | 5'-TCT CTG AGG CGG GAA AGG-3' | (SEQ ID NO: 2) |
| 2 | MSH2-2F-2-INSIDE | 5'-TTT TTT TTT TTT TAA GGA GC-3' | (SEQ ID NO: 3) |
|   | MSH2-2R-FULL | 5'-CAC ATT TTT ATT TTT CTA CTC-3' | (SEQ ID NO: 4) |
| 3 | MSH3F | 5'-GCT TAT AAA ATT TTA AAG TAT GTT C-3' | (SEQ ID NO: 5) |
|   | MSH3R-2 | 5'-CTG GAA TCT CCT CTA TCA C-3' | (SEQ ID NO: 6) |
| 4 | MSH4F | 5'-TTC ATT TTT GCT TTT CTT ATT CC-3' | (SEQ ID NO: 7) |
|   | MSH4R | 5'-ATA TGA CAG AAA TAT CCT TC-3' | (SEQ ID NO: 8) |
| 5 | MSH2-5F-1 | 5'-CAG TGG TAT AGA AAT CTT CGA-3' | (SEQ ID NO: 9) |
|   | MSH2-5R-2-INSIDE | 5'-TTT TTT TTT TTT TTA CCT GA-3' | (SEQ ID NO: 10) |
| 6 | MSH6F-1 | 5'-ACT AAT GAG CTT GCC ATT CT-3' | (SEQ ID NO: 11) |
|   | MSH6R-1 | 5'-TGG GTA ACT GCA GGT TAC A-3' | (SEQ ID NO: 12) |
| 7 | MSH7F | 5'-GAC TTA CGT GCT TAG TTG-3' | (SEQ ID NO: 13) |
|   | MSH7R | 5'-AGT ATA TAT TGT ATG AGT TGA AGG-3' | (SEQ ID NO: 14) |
| 8 | MSH8F | 5'-GAT TTG TAT TCT GTA AAA TGA GAT C-3' | (SEQ ID NO: 15) |
|   | MSH8R | 5'-GGC CTT TGC TTT TTA AAA ATA AC-3' | (SEQ ID NO: 16) |
| 9 | MSH9F | 5'-GTC TTT ACC CAT TAT TTA TAG G-3' | (SEQ ID NO: 17) |
|   | MSH9R | 5'-GTA TAG ACA AAA GAA TTA TTC C-3' | (SEQ ID NO: 18) |
| 10 | MSH10F | 5'-GGT AGT AGG TAT TTA TGG AAT AC-3' | (SEQ ID NO: 19) |
|   | MSH10R | 5'CAT GTT AGA GCA TTT AGG G-3' | (SEQ ID NO: 20) |

TABLE 2-continued

MSH2 PRIMER SEQUENCES

| Exon | Primer | Sequence | | |
|---|---|---|---|---|
| 11 | MSH11F | 5'-CAC ATT GCT TCT AGT ACA C-3' | (SEQ ID NO: 21) |
|    | MSH11R | 5'-CCA GGT GAC ATT CAG AAC-3'   | (SEQ ID NO: 22) |
| 12 | MSH12F | 5'-ATT CAG TAT TCC TGT GTA C-3' | (SEQ ID NO: 23) |
|    | MSH12R | 5'-CGT TAC CCC CAC AAA GC-3'    | (SEQ ID NO: 24) |
| 13 | MSH13F-1 | 5'ATG CTA TGT CAG TGT AAA CC-3' | (SEQ ID NO: 25) |
|    | MSH13R-1 | 5'CCA CAG GAA AAC AAC TAT TA-3' | (SEQ ID NO: 26) |
| 14 | MSH14F | 5'-TAC CAC ATT TTA TGT GAT GG-3' | (SEQ ID NO: 27) |
|    | MSH14R | 5'-GGG GTA GTA AGT TTC CC-3'    | (SEQ ID NO: 28) |
| 15 | MSH15F | 5'-CTC TTC TCA TGC TGT CCC-3'   | (SEQ ID NO: 29) |
|    | MSH15R | 5'-ATA GAG AAG CTA AGT TAA AC-3'| (SEQ ID NO: 30) |
| 16 | MSH16F | 5'-TAA TTA CTC ATG GGA CAT TC-3'| (SEQ ID NO: 31) |
|    | MSH16R-1 | 5'GGC ACT GAC AGT TAA CAC TA-3' | (SEQ ID NO: 32) |

NOTE: These MSH2 primers are M-13 tailed:
M13 tail for F: 5'-TGT AAA ACG ACG GCC AGT-3' (SEQ ID NO: 33) added to 5' end of primer above M13 tail for R: 5'-CAG GAA ACA GCT ATG ACC-3' (SEQ ID NO: 34) added to 5' end of primer above Thirty-five cycles are performed, each consisting of denaturing (95° C.; 30 seconds), annealing (55° C.; 1 minute), and extension (72° C.; 90 seconds), except during the first cycle in which the denaturing time was increased to 5 minutes, and during the last cycle in which the extension time was increased to 5 minutes.

PCR products are purified using Qia-quick® PCR purification kits (Qiagen®, cat#28104; Chatsworth, Calif.). Yield and purity of the PCR product determined spectrophotometrically at $OD_{260}$ on a Beckman DU 650 spectrophotometer.

All exons of the MSH2 gene are subjected to direct dideoxy sequence analysis by asymmetric amplification using the polymerase chain reaction (PCR) to generate a single stranded product amplified from this DNA sample. Shuldiner, et al., Handbook of Techniques in Endocrine Research, p. 457–486, DePablo, F., Scanes, C., eds., Academic Press, Inc., 1993. Fluorescent dye is attached to PCR products for automated sequencing using the Taq Dye Terminator Kit (Perkin-Elmer® cat#401628). DNA sequencing is performed in both forward and reverse directions on an Applied Biosystems, Inc. (ABI) Foster City, Calif., automated sequencer (Model 377). The software used for analysis of the resulting data is "Sequence Navigator®" purchased through ABI.

Results

No differences in nucleotide sequence are observed among the coding exons of the five normal individuals (10 chromosomes), nor between these 10 chromosomal sequences and the sequence published in GenBank (Accession No. U03911) for MSH2. Thus, all ten individuals are homozygous for the same allele. An additional sixty-two normal individuals are sequenced end-to-end to confirm this result. Once again no sequence variation is found within the exons. However, minor variation in three single nucleotide polymorphisms are found in non-coding intronic sequences (IVS9-9; IVS10+6; IVS 10+12). The results are summarized in Table 3, below.

TABLE 3

MSH2 HAPLOTYPES
Allelic Variations

| Haplotype | IVS9-9 | IVS10 + 6 | IVS10 + 12 | Number of Chromosomes |
|---|---|---|---|---|
| GenBank sequence (U03911) | T | T | A | 98 (73%) |
| Variant #1 | A | C | G | 28 (21%) |
| Variant #2 | A | C | A* | 6 (4.5%) |
| Variant #3 | T | C** | A | 2 (1.5%) |

*Variant #2 is an uncommon derivative chromosome of variant #1
**Variant #3 is a rarer derivative chromosome of GenBank cDNA Since the exonic coding sequence is maintained on all 4 haplotypes, such non-coding sequence variation did not result in any new "normal" coding consensus sequence of the MSH2 gene.

These results demonstrate that the sequence in the GenBank Repository is the "consensus normal DNA sequence" that should be used for comparison in all clinical applications to determine an individual with a hereditary susceptibility to HNPCC. In addition, these results indicate that normal MSH2 protein function, i.e., mismatch repair function, is under a large degree of selective pressure to maintain viability in the human population. Very little if any variation in the activity of the MSH2 protein's mismatch repair function is tolerated, as reflected by the extraordinarily high degree of conservation of the normal sequence.

EXAMPLE 2
Determining the Functional Allele Profile for MLH1

All procedures (e.g., selection of five individuals at low risk of being carriers for MLH1 mutations, isolation of genomic DNA, amplification of exons, sequencing of amplified exons, and analysis of sequence data) are carried out as described in Example 1, above, except that the amplification is carried out using primers specific to the MLH1 exons as set forth in Table 4, below.

TABLE 4

MLH1 PRIMER SEQUENCES

| Exon | Primer | Sequence | |
|---|---|---|---|
| 1 | MLHAF | 5'-AGG CAC TGA GGT GAT TGG C-3' | (SEQ ID NO: 35) |
|   | MLHAR | 5'-TCG TAG CCC TTA AGT GAG C-3' | (SEQ ID NO: 36) |
| 2 | MLHBF-2 | 5'-TGA GGC ACT ATT GTT TGT ATT T-3' | (SEQ ID NO: 37) |
|   | MLHBR-2 | 5'-TGT TGG TGT TGA ATT TTT CAG T-3' | (SEQ ID NO: 38) |
| 3 | MLHCF | 5'-AGA GAT TTG GAA AAT GAG TAA C-3' | (SEQ ID NO: 39) |
|   | MLHCR | 5'-ACA ATG TCA TCA CAG GAG G-3' | (SEQ ID NO: 40) |
| 4 | MLHDF-1 | 5'-TGA GGT GAG AGT GGG TGA-3' | (SEQ ID NO: 41) |
|   | MLHGR | 5'-GAT TAC TCT GAG ACC TAG GC-3' | (SEQ ID NO: 42) |
| 5 | MLHEF | 5'-GAT TTT GTG TTT TCC CCT TGG G-3' | (SEQ ID NO: 43) |
|   | MLHER | 5'-CAA ACA AAG CTT CAA CAA TTT AC-3' | (SEQ ID NO: 44) |
| 6 | MLHFF | 5'-GGG TTT TAT TTT CAA GTA CTT GTA TG-3' | (SEQ ID NO: 45) |
|   | MLHFR | 5'-GCT CAG CAA CTG TTC AAT GTA GC-3' | (SEQ ID NO: 46) |
| 7 | MLHGF | 5'-CTA-GTG TGT GTT TTT GGC-3' | (SEQ ID NO: 47) |
|   | MLHGR | 5'-CAT AAC CTT ATC TCC ACC-3' | (SEQ ID NO: 48) |
| 8 | MLHHF | 5'-CTC AGC CAT GAG ACA ATA AAT CC-3' | (SEQ ID NO: 49) |
|   | MLHHR | 5'-GGT TCC CAA ATA ATG TGA TGG-3' | (SEQ ID NO: 50) |
| 9 | MLHIF-1 | 5'-GTT TAT GGG NAG GAA CCT TGT-3' | (SEQ ID NO: 51) |
|   | MLHIR-1 | 5'-TGG TCC CAT AAA ATT CCC TGT-3' | (SEQ ID NO: 52) |
| 10 | MLHJF | 5'-CAT GAC TTT GTG TGA ATG TAG ACC-3' | (SEQ ID NO: 53) |
|    | MLHJR | 5'-GAG GAG AGC CTG ATA GAA CAT CTG-3' | (SEQ ID NO: 54) |
| 11 | MLHKF | 5'-GGG CTT TTT CTC CCC CTC CC-3' | (SEQ ID NO: 55) |
|    | MLHKR | 5'-AAA ATC TGG GCT CTC ACG-3' | (SEQ ID NO: 56) |
| 12 | MLH1-LAF-2-INSIDE | 5'-TTT AAT ACA GAC TTT GCT AC-3' | (SEQ ID NO: 57) |
|    | MLH1-LBR | 5'-GAA AAG CCA AAG TTA GAA GG-3' | (SEQ ID NO: 58) |
| 13 | MLHMF | 5'-TGC AAC CCA CCA AAT TTG C-3' | (SEQ ID NO: 59) |
|    | MLHMR | 5'-CTT TCT CCA TTT CCA AAA CC-3' | (SEQ ID NO: 60) |
| 14 | MLHNF | 5'-TGG TGT CTC TAG TTC TGG-3' | (SEQ ID NO: 61) |
|    | MLHNR | 5'-CAT TGT TGT AGT AGC TCT GC-3' | (SEQ ID NO: 62) |
| 15 | MLHOF-2* | 5'-GCA GAA CTA TGT CTG TCT CAT-3' | (SEQ ID NO: 63) |
|    | MLHOR | 5'-CGG TCA GTT GAA ATG TCA G-3' | (SEQ ID NO: 64) |
| 16 | MLHPF | 5'-CAT TTG GAT CCG TTA NAG C-3' | (SEQ ID NO: 65) |
|    | MLHPR | 5'-CAC CCG GCT GGA AAT TTT ATT TG-3' | (SEQ ID NO: 66) |
| 17 | MLHQF | 5'-GGA AAG GCA CTG GAG AAA TGG G-3' | (SEQ ID NO: 67) |
|    | MLHQR | 5'-CCC TCC AGC ACA CAT GCA TGT ACC G-3' | (SEQ ID NO: 68) |
| 18 | MLHRF | 5'-TAA GTA GTC TGT GAT CTC CG-3' | (SEQ ID NO: 69) |
|    | MLHRR | 5'-ATG TAT GAG GTC GTG TCC-3' | (SEQ ID NO: 70) |
| 19 | MLHSF | 5'-GAC ACC AGT GTA TGT TGG-3' | (SEQ ID NO: 71) |
|    | MLHSR* | 5'-GAG AAA GAA GAA CAC ATC CC-3' | (SEQ ID NO: 72) |

NOTE: MLH1 primers are M-13 tailed,
*EXCEPT for MLH1 primers MLHOF-2, MLHOR & MLHSR:

M13 tail for F: 5'-TGT AAA ACG ACG GCC AGT-3' added to 5' end of primer above

M13 tail for R: 5'-CAG GAA ACA GCT ATG ACC-3' added to 5' end of primer above

Results

No differences are observed among the coding exons of the five normal individuals (10 chromosomes), nor between these 10 chromosomal sequences and the sequence published in GenBank (Accession No. U40978) for the MLH1 gene. In order to confirm these findings confirmatory sequencing is performed on an additional 62 samples. Among these sixty-two samples, variations are identified in only two positions as summarized in Table 5, below.

TABLE 5

MLH1 Haplotypes Allelic Variation

| Haplotype | EXON 8 codon 219 | IVS14 – 19 | Number of Chromosomes |
|---|---|---|---|
| GenBank Sequence (040978) | A | A | 114 (92.5%) |
| Variant #1 | A | G | 5 (3.7%) |
| Variant #2 | G | G | 4 (3.1%) |
| Variant #3 | G | A | 1 (0.7%) |
| | | Total | 134 (100%) |

One sequence variation is within exon 8 wherein a single nucleotide change from A to G in the first position of codon 219 (ATC→GTC) changes the amino acid from Ile to Val. This sequence variation occurs approximately 3.7% of the time in this population. The second sequence variation is deep within an intron (IV514–19) and can be found to be independently segregating with the exon 8 polymorphisms. While there were two "normal" exonic haplotypes identified in MLH1 (A versus G at codon 219), the most commonly found haplotype (i.e. consensus normal DNA sequence) having an A at the first position of codon 219 is the sequence currently in the GenBank database which should be used as the standard for clinical comparisons.

In addition, this analysis demonstrated that there is less selective pressure on the MLH1 gene (since codon 219 can have two forms) than on the MSH2 gene where no exonic sequence variation was tolerated. Given that these two genes are both mismatch repair genes, this observation indicates that the degree of redundancy of function (i.e., level of hierarchy between these proteins) is MSH2 as the primary system with MLH1 only as secondary or backup when MSH2 is dysfunctional (i.e., mutant). While empiric data from other studies proposed such a relationship, only determining the actual functional allele profiles for these two genes provides an accurate understanding of the basis of previous observations from population studies.

EXAMPLE 3

Determining the Functional Allele Profile for BRCA1

All procedures (e.g., selection of five individuals at low risk of being carriers for BRCA1 mutations, isolation of genomic DNA, amplification of exons, and sequencing of amplified exons, and analysis of sequence data) are carried out as described in Example 1, above, except that the amplification is carried out using primers specific to the BRCA1 exons as set forth in Table 6, below.

TABLE 6

BRCA1 PRIMERS FOR SEQUENCING TEMPLATES

| Exon | Primer | SEQUENCE | $Mg^{++}$ | SIZE |
|---|---|---|---|---|
| 2 | 2F | 5'GAAGTTGTCATTTTATAAACCTTT-3' (SEQ ID NO: 73) | 1.6 | 275 |
|   | 2R | 5'TGTCTTTTCTTCCCTAGTATGT-3' (SEQ ID NO: 74) | | |
| 3 | 3F | 5'TCCTGACACAGCAGACATTA-3' (SEQ ID NO: 75) | 1.4 | 375 |
|   | 3R | 5'TTGGATTTCGTTCTCACTTTA-3' (SEQ ID NO: 76) | | |
| 5 | 5F | 5'CTCTTAAGGGCAGTTGTGAG-3' (SEQ ID NO: 77) | 1.2 | 275 |
|   | 5R | 5'TTCCTACTGTGGTTGCTTCC-3' (SEQ ID NO: 78) | | |
| 6 | 6/7F | 5'CTTATTTTAGTGTCCTTAAAAGG-3' (SEQ ID NO: 79) | 1.6 | 250 |
|   | 6R | 5'TTTCATGGACAGCACTTGAGTG-3' (SEQ ID NO: 80) | | |
| 7 | 7F | 5'CACAACAAAGAGCATACATAGGG-3' (SEQ ID NO: 81) | 1.6 | 275 |
|   | 6/7R | 5'TCGGGTTCACTCTGTAGAAG-3' (SEQ ID NO: 82) | | |
| 8 | 8F1 | 5'TTCTCTTCAGGAGGAAAAGCA-3' (SEQ ID NO: 83) | 1.2 | 270 |
|   | 8R1 | 5'GCTGCCTACCACAAATACAAA-3' (SEQ ID NO: 84) | | |
| 9 | 9F | 5'CCACAGTAGATGCTCAGTAAA TA-3' (SEQ ID NO: 85) | 1.2 | 250 |
|   | 9R | 5'TAGGAAAATACCAGCTTCATAGA-3' (SEQ ID NO: 86) | | |
| 10 | 10F | 5'TGGTCAGCTTTCTGTAATCG-3' (SEQ ID NO: 87) | 1.6 | 250 |
|   | 10R | 5'GTATCTACCCACTCTCTTCTTCAG-3' (SEQ ID NO: 88) | | |
| 11A | 11AF | 5'CCACCTCCAAGGTGTATCA-3' (SEQ ID NO: 89) | 1.2 | 372 |
|   | 11AR | 5'TGTTATGTTGGCTCCTTGCT-3' (SEQ ID NO: 90) | | |
| 11B | 11BF1 | 5'CACTAAAGACAGAATGAATCTA-3' (SEQ ID NO: 91) | 1.2 | 400 |
|   | 11BR1 | 5'GAAGAAGCAGAATATTCATCTA-3' (SEQ ID NO: 92) | | |
| 11C | 11CF1 | 5'TGATGGGGAGTCTGAATCAA-3' (SEQ ID NO: 93) | 1.2 | 400 |
|   | 11CR1 | 5'TCTGCTTTCTTGATAAAATCCT-3' (SEQ ID NO: 94) | | |

TABLE 6-continued

BRCA1 PRIMERS FOR SEQUENCING TEMPLATES

| Exon | Primer | SEQUENCE | Mg++ | SIZE |
|---|---|---|---|---|
| 11D | 11DF1 | 5'AGCGTCCCCTCACAAATAAA-3' (SEQ ID NO: 95) | 1.2 | 400 |
|  | 11DR1 | 5'TCAAGCGCATGAATATGCCT-3' (SEQ ID NO: 96) |  |  |
| 11E | 11EF | 5'GTATAAGCAATATGGAACTCGA-3' (SEQ ID NO: 97) | 1.2 | 388 |
|  | 11ER | 5'TTAAGTTCACTGGTATTTGAACA-3' (SEQ ID NO: 98) |  |  |
| 11F | 11FF | 5'GACAGCGATACTTTCCCAGA-3' (SEQ ID NO: 99) | 1.2 | 382 |
|  | 11FR | 5'TGGAACAACCATGAATTAGTC-3' (SEQ ID NO: 100) |  |  |
| 11G | 11GF | 5'GGAAGTTAGCACTCTAGGGA-3' (SEQ ID NO: 101) | 1.2 | 423 |
|  | 11GR | 5'GCAGTGATATTAACTGTCTGTA-3' (SEQ ID NO: 102) |  |  |
| 11H | 11HF | 5'TGGGTCCTTAAAGAAACAAAGT-3' (SEQ ID NO: 103) | 1.2 | 366 |
|  | 11HR | 5'TCAGGTGACATTGAATCTTCC-3' (SEQ ID NO: 104) |  |  |
| 11I | 11IF | 5'CCACTTTTTCCCATCAAGTCA-3' (SEQ ID NO: 105) | 1.2 | 377 |
|  | 11IR | 5'TCAGGATGCTTACAATTACTTC-3' (SEQ ID NO: 106) |  |  |
| 11J | 11JF | 5'CAAAATTGAATGCTATGCTTAGA-3' (SEQ ID NO: 107) | 1.2 | 377 |
|  | 11JR | 5'TCGGTAACCCTGAGCCAAAT-3' (SEQ ID NO: 108) |  |  |
| 11K | 11KF | 5'GCAAAAGCGTCCAGAAAGGA-3' (SEQ ID NO: 109) | 1.2 | 396 |
|  | 11KR-1 | 5'TATTTGCAGTCAAGTCTTCCAA-3' (SEQ ID NO: 110) |  |  |
| 11L | 11LF-1 | 5'GTAATATTGGCAAAGGCATCT-3' (SEQ ID NO: 111) | 1.2 | 360 |
|  | 11LR | 5'TAAAATGTGCTCCCCAAAAGCA-3' (SEQ ID NO: 112) |  |  |
| 12 | 12F | 5'GTCCTGCCAATGAGAAGAAA-3' (SEQ ID NO: 113) | 1.2 | 300 |
|  | 12R | 5'TGTCAGCAAACCTAAGAATGT-3' (SEQ ID NO: 114) |  |  |
| 13 | 13F | 5'AATGGAAAGCTTCTCAAAGTA-3' (SEQ ID NO: 115) | 1.2 | 325 |
|  | 13R | 5'ATGTTGGAGCTAGGTCCTTAC-3' (SEQ ID NO: 116) |  |  |
| 14 | 14F | 5'CTAACCTGAATTATCACTATCA-3' (SEQ ID NO: 117) | 1.2 | 310 |
|  | 14R | 5'GTGTATAAATGCCTGTATGCA-3' (SEQ ID NO: 118) |  |  |
| 15 | 15F | 5'TGGCTGCCCAGGAAGTATG-3' (SEQ ID NO: 119) | 1.2 | 375 |
|  | 15R | 5'AACCAGAATATCTTTATGTAGGA-3' (SEQ ID NO: 120) |  |  |
| 16 | 16F | 5'AATTCTTAACAGAGACCAGAAC-3' (SEQ ID NO: 121) | 1.6 | 550 |
|  | 16R | 5'AAAACTCTTTCCAGAATGTTGT-3' (SEQ ID NO: 122) |  |  |
| 17 | 17F | 5'GTGTAGAACGTGCAGGATTG-3' (SEQ ID NO: 123) | 1.2 | 275 |
|  | 17R | 5'TCGCCTCATGTGGTTTTA-3' (SEQ ID NO: 124) |  |  |
| 18 | 18F | 5'GGCTCTTTAGCTTCTTAGGAC-3' (SEQ ID NO: 125) | 1.2 | 350 |
|  | 18R | 5'GAGACCATTTTCCCAGCATC-3' (SEQ ID NO: 126) |  |  |
| 19 | 19F | 5'CTGTCATTCTTCCTGTGCTC-3' (SEQ ID NO: 127) | 1.2 | 250 |
|  | 19R | 5'CATTGTTAAGGAAAGTGGTGC-3' (SEQ ID NO: 128) |  |  |
| 20 | 20F | 5'ATATGACGTGTCTGCTCCAC-3' (SEQ ID NO: 129) | 1.2 | 425 |
|  | 20R | 5'GGGAATCCAAATTACACAGC-3' (SEQ ID NO: 130) |  |  |
| 21 | 21F | 5'AAGCTCTTCCTTTTTGAAAGTC-3' (SEQ ID NO: 131) | 1.6 | 300 |
|  | 21R | 5'GTAGAGAAATAGAATAGCCTCT-3' (SEQ ID NO: 132) |  |  |
| 22 | 22F | 5'TCCCATTGAGAGGTCTTGCT-3' (SEQ ID NO: 133) | 1.6 | 300 |
|  | 22R | 5'GAGAAGACTTCTGAGGCTAC-3' (SEQ ID NO: 134) |  |  |
| 23 | 23F-1 | 5'TGAAGTGACAGTTCCAGTAGT-3' (SEQ ID NO: 135) | 1.2 | 250 |
|  | 23R-1 | 5'CATTTTAGCCATTCATTCAACAA-3' (SEQ ID NO: 136) |  |  |
| 24 | 24F | 5'ATGAATTGACACTAATCTCTGC-3' (SEQ ID NO: 137) | 1.4 | 285 |
|  | 24R | 5'GTAGCCAGGACAGTAGAAGGA-3' (SEQ ID NO: 138) |  |  |

[1] M13 tailed

Results

Differences in the nucleotide sequences of the five normal individuals are found in seven locations on the gene. The data show that for each of the samples, the BRCA1 gene is identical except in the region of seven single nucleotide polymorphisms. The changes and their positions are summarized on Table 7, below, and are depicted in schematic form in FIG. 1. The alternative alleles containing polymorphic (non-mutation causing allelic variations) sites along the BRCA1 gene are represented in FIG. 1 as individual "haplotypes" of the BRCA1 gene. The BRCA1$^{(omi1)}$ haplotype is shown in FIG. 1 and indicated with dark shading. The alternative allelic variations occurring at nucleotide positions 2201, 2430, 2731, 3232, 3667, 4427, and 4956 are shown. For comparison, the haplotype previously available in GenBank (as Accession No. U14680) is completely unshaded and designated "GB". As can be seen, the most common, "consensus" haplotype occurs in five separate chromosomes labeled with the OMI symbol (haplotypes 1–5 from left to right). Two additional haplotypes (BRCA1$^{(omi2)}$, and BRCA1$^{(omi3)}$ are represented with mixed shaded and unshaded positions (numbers 7 and 9 from left to right). In total, 7 of the ten 10 haplotypes identified in the group of five individuals tested are not the haplotype available in GenBank.

The changes, their positions, and their frequencies among the five individuals (ten chromosomes) initially analyzed are summarized on Table 7, below.

TABLE 7

NORMAL PANEL TYPING

| AMINO ACID CHANGE | EXON | 1 | 2 | 3 | 4 | 5 | FRE-QUENCY |
|---|---|---|---|---|---|---|---|
| SER(SER) (694) | 11E | C/C | C/T | C/T | T/T | T/T | 0.4 C 0.6 T |
| LEU(LEU) (771) | 11F | T/T | C/T | C/T | C/C | C/C | 0.4 T 0.6 C |
| PRO(LEU) (871) | 11G | C/T | C/T | C/T | T/T | T/T | 0.3 C 0.7 T |
| GLU(GLY) (1038) | 11I | A/A | A/G | A/G | G/G | G/G | 0.4 A 0.6 G |
| LYS(ARG) (1183) | 11J | A/A | A/G | A/G | G/G | G/G | 0.4 A 0.6 G |
| SER(SER) (1436) | 13 | T/T | T/T | T/C | C/C | C/C | 0.5 T 0.5 C |
| SER(GLY) (1613) | 16 | A/A | A/G | A/G | G/G | G/G | 0.4 A 0.6 G |

Note that there is no requirement to sequence the additional normal individuals available, as has been done for MSH2 (Example 1, above) and MLH1 (Example 2, above) to more accurately determine the frequencies of uncommon polymorphisms. A common haplotype (the "consensus") is readily evident as different from the GenBank sequence (FIG. 1, "GB") in 50% of chromosomes and indeed is homozygous in two normal individuals.

Thus, the "consensus" sequence of the BRCA (omi$^1$) should be used as the only true standard for clinical diagnostic analysis in order to avoid misinterpreting polymorphisms as pathologic mutations.

In the alternative, one could compare the test sequence against all four of the BRCA1 functional haplotypes.

EXAMPLE 4

Pharmacogenetic Analysis of Sulfa Drug Sensitivity

The glucose-6-phosphate dehydrogenase gene is located on the X chromosome. Individuals with certain sequence variations in the G6PDH gene lead relatively normal lives unless they are exposed to certain chemicals found in fava beans, primaquine and sulfonamide antibiotics (sulfisoxazole, sulfamethoxazole, sulfathiazole, sulfacetamide, etc.). Upon administration of such compounds to the individual, severe reactions including hemolytic anemia occur in individuals having certain haplotype(s) of the G6PDH gene. These individuals are generally of African and Mediterranean heritage. Because these sequence variations are otherwise of little importance, they have been called both polymorphisms and mutations in the literature. For the purposes of this application, they are called mutations to distinguish them from clear polymorphisms. Genetic analysis in chimpanzees and various human populations indicate that the probable natural "wild-type" is found in individuals sensitive to sulfonamide antibiotics. Beutler et al, *Blood* 74: 2550–2555 (1989).

A number of apparently inconsequential single nucleotide polymorphisms (SNPs) in the G6PDH gene are known including at intron 5 (PvuII site), nucleotides 202 (Nla III site), 376 (Fok I site), 1311 and 1116 (Pst I sites). These constitute and define the haplotype. Missense mutations occur at amino acids 32, 48, 58, 68, 106, 126, 131, 156, 163, 165, 181, 182, 188, 198, 213, 216, 227, 282, 285, 291, 317, 323, 335, 342, 353, 363, 385, 386, 387, 393, 394, 398, 410, 439, 447, 454, 459, 463 and amino acid 35 deleted. Many mutations are restricted to certain haplotypes. Thus, haplotype determination provides an indication of whether the individual is sensitive to the drugs listed above.

Experimental

Blood is drawn from 30 individuals of African-American heritage with urinary tract infections having bacteria sensitive to sulfa antibiotics and for whom treatment with trimethoprim-sulfamethiazole is otherwise deemed appropriate. 1 mg of genomic DNA from individuals is isolated from peripheral blood lymphocytes and amplified by PCR using the primers listed in Hirono et al, *Proc. Natl. Acad. Sci. USA* 85:3951–3954 (1988) and Beutler et al, *Human Genetics* 87:462–464 (1990) according to the methods in Example 1 above. Amplified fragments are divided into five aliquots and four of which are cleaved by a restriction enzyme, either PvuII, Nla III, Fok I or Pst I, according to the manufacturer's (Stratagene and New England Biolabs) instructions. The digests are electrophoresed in a 4% agarose gel (NuSieve, FMC) with 10 ml of ethidium bromide (10 mg/ml) and the number of bands counted under ultraviolet light. The number of bands indicates the presence or absence of restriction enzyme cleavage and presence of a particular nucleotide at the polymorphic site.

An oligonucleotide probe for determining the polymorphic site at nucleotide 1311 is listed in Beutler et al, *Human Genetics* 87:462–464 (1990). The fifth aliquot is immobilized on a membrane and an ASO (allele specific oligonucleotide) hybridization assay is performed according to the method of Example 5 below. The presence or absence of the label indicating hybridization is considered indicative of the presence of a particular nucleotide at the polymorphic site.

Individuals having a haplotype, particularly the polymorphism at nucleotide 1116, indicative of very low likelihood of a G6PDH mutation sensitive to sulfamethiazole are given 160 mg trimethoprim with 800 mg sulfamethiazole (SEPTRA DS). Individuals having a haplotype or polymorphism indicative of a possible presence of a G6PDH mutation sensitive to sulfamethiazole are given a different antibiotic (varied with the patient) to which their infecting organism was susceptible.

Confirmatory sequencing of both alleles (60 chromosomes) of the coding region of the G6PDH gene is later performed by the techniques of Example 1 to determine the presence of a sensitizing mutation. The haplotype(s) associated with a mutation and those not associated with a mutation are recorded. A panel of oligonucleotides bound to a membrane or other solid phase such as a DNA chip distinguishing the haplotypes and/or the common mutations also is to become part of the present invention.

EXAMPLE 5

Pharmacogenetic Analysis of BRCA1, BRCA2, PTEN, BAP1, BARD1 and hRAD51 Haplotypes and the Use of Tamoxifen to Prevent Breast Cancer While every step in carcinogenesis is not known, the BRCA1, BRCA2, PTEN, BAP1, BARD1 and hRAD51 proteins are either involved in breast, ovarian, prostate and other cancer susceptibility, in the metabolic pathway of or interact with such proteins. It was determined that the most common form of heriditary breast and ovarian cancer, the BRCA1 185delAG mutation, was found essentially exclusively in one haplotype, namely haplotype OMI1 as defined in Example 1, FIG. 1 and U.S. Pat. No. 5,654,155. As such it was applicants hypothesis that the haplotypes of other related and similar genes alone or in certain combinations provide an indication of association with breast and other cancers associated with these genes, e.g. ovarian, pancreatic, prostate, colon, etc.

The various treatments and prophylactics useful against the disease are also believed to be related to the haplotypes. It is already known that certain mutant genes result in different presentations of cancers and different treatment. For example, BRCA1 mutations in the early part of the coding sequence generally form cancers at a younger age than mutations in the later part of the coding sequence. Likewise, breast cancer arising from BRCA2 mutations are typically more sensitive to radiation treatment than other breast cancers. Since some of these proteins actually bind to each other, different combinations of haplotypes may bind with different avidity to each other and operate slightly differently under certain circumstances. Likewise for proteins which act at separate reactions within the tumor-suppressing mechanisms.

Experimental

Blood samples are drawn from 47 women prescribed tamoxifen to prevent breast cancer or having had breast cancer to prevent reoccurrence of breast cancer. The DNA sequence for BRCA1 is determined in the regions of the single nucleotide polymorphic sites which constitute the haplotype use the primers according to U.S. Pat. No. 5,654, 155. Those of BRCA2 are determined by using the primers of U.S. patent application Ser. No. 09/084,471 filed May 22, 1998 or using the primers:

TABLE 8

BRCA2 PRIMERS

| EXON | SEQUENCE | POLY-MORPHISM |
|------|----------|---------------|
| 10AF | 5'GAATAATATAAATTATATGGCTTA-3' (SEQ ID NO: 139) | 1093 |
| 10AF | 5'CCTAGTCTTGCTAGTTCTT-3' (SEQ ID NO: 140) | 1093 |
| 10BE | 5'ARCTGAAGTGGAACCAAATGATAC-3' (SEQ ID NO: 141) | 1593 |
| 10BR | 5'ACGTGGCAAAGAATTCTCTGAAGTAA-3' (SEQ ID NO: 142) | 1593 |
| 11BF | 5'AAGAAGCAAAATGTAATAAGGA-3' (SEQ ID NO: 143) | 2457 |
| 11BR | 5'CATTTAAAGCACATACATCTTG-3' (SEQ ID NO: 144) | 2457 |
| 11CF | 5'TCTAGAGGCAAAGAATCATAC-3' (SEQ ID NO: 145) | 2908 |
| 11CR | 5'CAAGATTATTCCTTTCATTAGC-3' (SEQ ID NO: 146) | 2908 |
| 11DF | 5'AACCAAAACACAAATCTAAGAG-3' (SEQ ID NO: 147) | 3199 |
| 11DR | 5'GTCATTTTTATATGCTGCTTTAC-3' (SEQ ID NO: 148) | 3199 |
| 11EF | 5'GGTTTTATATGGAGACACAGG-3' (SEQ ID NO: 149) | 3624 |
| 11ER | 5'GTATTTACAATTTCAACACAAGC-3' (SEQ ID NO: 150) | 3624 |
| 11FF | 5'ATCACAGTTTTGGAGGTAGC-3' (SEQ ID NO: 151) | 4035 |
| 11FR | 5'CTGACTTCCTGATTCTTCTAA-3' (SEQ ID NO: 152) | 4035 |
| 14F | 5'ACCATGTAGCAAATGAGGGTCT-3' (SEQ ID NO: 153) | 7470 |
| 14R | 5'GCTTTTGTCTGTTTTCCTCAA-3' (SEQ ID NO: 154) | 7470 |
| 22F | 5'AACCACACCCTTAAGATGA-3' (SEQ ID NO: 155) | 9079 |
| 22R | 5'GCATAAGTAGTGGATTTTGC-3' (SEQ ID NO: 156) | 9079 |

The DNA sequences for haplotypes of PTEN are determined by using the published primers of Table 3, Liaw et al, *Nature Genetics*, 16(1): p. 64–67 (1997).

The primers for amplifying hRAD51 are:

5'GGGCCCGGATCCATGGCAATGCAGATGCAGC-3' (SEQ ID NO: 157) and

5'GGGCCCCAATGGATATCATTCAGTCTTTGGCATCTCCCACTCC-3' (SEQ ID NO: 158).

The primers for amplifying BAP1 are:

| PRIMER | SEQUENCE |
|--------|----------|
| BAP1A1-F | 5'CACGAGGCATGGCGCTGAGG-3' (SEQ ID NO: 159) |
| BAP1A-R | 5'CCGGGCCTTGTCTGTCCACT-3' (SEQ ID NO: 160) |

-continued

| PRIMER | SEQUENCE | |
|---|---|---|
| BAP1B-F | 5'GTCTACCCCATTGACCATGG-3' | (SEQ ID NO: 161) |
| BAP1B-R | 5'TCATCATCTGAGTACTGCTG-3' | (SEQ ID NO: 162) |
| BAP1C-F | 5'TGCAGGAGGAAGAAGACCTG-3' | (SEQ ID NO: 163) |
| BAP1C-R | 5'TCTGTCAGCGCCAGGGGACT-3' | (SEQ ID NO: 164) |
| BAP1D-F | 5'AGCACAGGCCTGCTGCACCT-3' | (SEQ ID NO: 165) |
| BAP1D-R | 5'GAAAAGGGGAAGTGGGGCAG-3' | (SEQ ID NO: 166) |

The primers for amplifying BAP1 for polymorphism detection in the 3' UTR are:

| BAP1-PF | 5'AGCCCAGGCCCCAACACAGCCCCATGGCCTCT-3' | (SEQ ID NO: 167) |
|---|---|---|
| BAP1-PR | 5'CTTAGGAGAGTTTTATTCATTCATTGATCCAG-3' | (SEQ ID NO: 168) |

The primers for amplifying BARD1 are:

5'AACAGTACAATGACTGGGCTC -3' (SEQ ID NO: 169) and

5'TCAGCGCTTCTGCACACAGT -3' (SEQ ID NO: 170)

In the cases of BARD1 and hRAD51, the PCR products are sequenced in entirety. All procedures (e.g., isolation of genomic DNA, amplification, sequencing, and analysis of sequence data) are carried out as described in Example 1. The method as described in Examples 1–3 is used to determine the common haplotypes in these genes.

Once standardized by sequencing, the amplified fragments of BRCA1, BRCA2, PTEN and BAP1, produced by PCR are assayed by hybridization to allele-specific oligonucleotides (ASO) which distinguish the polymorphic site directly. The ASO assay is performed as described in the following experiment.

Binding PCR Products to Nylon Membrane

The PCR products are denatured no more than 30 minutes prior to binding the PCR products to the nylon membrane. To denature the PCR products, the remaining PCR reaction (45 ml) and the appropriate positive control mutant gene amplification product are diluted to 200 ml final volume with PCR Diluent Solution (500 mM NaOH, 2.0 M NaCl, 25 mM EDTA) and mixed thoroughly. The mixture is heated to 95° C. for 5 minutes, and immediately placed on ice and held on ice until loaded onto dot blotter, as described below.

The PCR products are bound to 9 cm by 13 cm nylon ZETA PROBE BLOTTING MEMBRANE (BIO-RAD, Hercules, Calif., catalog number 162-0153) using a BIO-RAD dot blotter apparatus. Forceps and gloves are used at all times throughout the ASO analysis to manipulate the membrane, with care taken never to touch the surface of the membrane with bare hands or latex gloves.

Pieces of 3MM filter paper [WHATMAN®, Clifton, N.J.] and nylon membrane are pre-wet in 10×SSC prepared fresh from 20×SSC buffer stock. The vacuum apparatus is rinsed thoroughly with dH$_2$O prior to assembly with the membrane. 100 ml of each denatured PCR product is added to the wells of the blotting apparatus. Each row of the blotting apparatus contains a set of reactions for a single exon to be tested, including a placental DNA (negative) control, a synthetic oligonucleotide with the desired mutation or a PCR product from a known mutant sample (positive control), and three no template DNA controls.

After applying PCR products, the nylon filter is placed DNA side up on a piece of 3MM filter paper saturated with denaturing solution (1.5M NaCl, 0.5 M NaOH) for 5 minutes. The membrane is transferred to a piece of 3MM filter paper saturated with neutralizing solution (1M Tris-HCl, pH 8, 1.5 M NaCl) for 5 minutes. The neutralized membrane is then transferred to a dry 3MM filter DNA side up, and exposed to ultraviolet light (STRALINKER, STRATAGENE, La Jolla, Calif.) for exactly 45 seconds to fix the DNA to the membrane. This UV crosslinking should be performed within 30 min. of the denaturation/neutralization steps. The nylon membrane is then cut into strips such that each strip contains a single row of blots of one set of reactions for a single exon.

Hybridizing Labeled Oligonucleotides to the Nylon Membrane Prehybridization

The strip is prehybridized at 52° C. incubation using the HYBAID® (SAVANT INSTRUMENTS, INC., Holbrook, N.Y.) hybridization oven. 2×SSC (15 to 20 ml) is preheated to 52° C. in a water bath. For each nylon strip, a single piece of nylon mesh cut slightly larger than the nylon membrane strip (approximately 1"×5") is pre-wet with 2×SSC. Each single nylon membrane is removed from the prehybridization solution and placed on top of the nylon mesh. The membrane/mesh "sandwich" is then transferred onto a piece of Parafilm™. The membrane/mesh sandwich is rolled lengthwise and placed into an appropriate HYBAID® bottle, such that the rotary action of the HYBAID® apparatus caused the membrane to unroll. The bottle is capped and gently rolled to cause the membrane/mesh to unroll and to evenly distribute the 2×SSC, making sure that no air bubbles formed between the membrane and mesh or between the mesh and the side of the bottle. The 2×SSC is discarded and replaced with 5 ml TMAC Hybridization Solution, which contained 3 M TMAC (tetramethyl ammoniumchloride-SIGMA T-3411), 100 mM Na$_3$PO$_4$(pH 6.8), 1 mM EDTA, 5× Denhardt's (1% Ficoll, 1% polyvinylpyrrolidone, 1% BSA (fraction V)), 0.6% SDS, and 100 mg/ml Herring Sperm DNA. The filter strips were prehybridized at 52° C. with medium rotation (approx. 8.5 setting on the HYBAID® speed control) for at least one hour. Prehybridization can also be performed overnight.

Labeling Oligonucleotides

The DNA sequences of the oligonucleotide probes used to detect the BRCA1, BRCA2, PTEN, and BAP1 single nucleotide polymorphisms (SNPs) are as follows (for each polymorphism both options for the oligonucleotide are given below): The complements of these probes may also be used. Preliminary laboratory data indicates that probes with either greater specificity or sensitivity can be prepared by slightly varing the length and amount overlapping each side of the polymorphic region. It is expected that better probes will be prepared by routine experimentation.

TABLE 9

BRCA1

| | | | |
|---|---|---|---|
| 2201 | C | 5'ACATGACAGCGATACTT-3' | (SEQ ID NO: 171) |
| 2201 | T | 5'ACATGACAGTGATACTT-3' | (SEQ ID NO: 172) |
| 2430 | T | 5'AGTATTTCATTGGTACC-3' | (SEQ ID NO: 173) |
| 2430 | C | 5'AGTATTTCACTGGTACC-3' | (SEQ ID NO: 174) |
| 2731 | C | 5'CATTTGCTCCGTTTTCA-3' | (SEQ ID NO: 175) |
| 2731 | T | 5'CATTTGCTCTGTTTTCA-3' | (SEQ ID NO: 176) |
| 3232 | A | 5'TTTTTAAAGAAGCCAGC-3' | (SEQ ID NO: 177) |
| 3232 | G | 5'TTTTTAAAGGAGCCAGC-3' | (SEQ ID NO: 178) |
| 3667 | A | 5'GCGTCCAGAAAGGAGAG-3' | (SEQ ID NO: 179) |
| 3667 | G | 5'GCGTCCAGAGAGGAGAG-3' | (SEQ ID NO: 180) |
| 4427 | T | 5'AAGTGACTCTTCTGCCC-3' | (SEQ ID NO: 181) |
| 4427 | C | 5'AAGTGACTCCTCTGCCC-3' | (SEQ ID NO: 182) |
| 4956 | A | 5'TGTGCCCAGAGTCCAGC-3' | (SEQ ID NO: 183) |
| 4956 | G | 5'TGTGCCCAGGGTCCAGC-3' | (SEQ ID NO: 184) |
| 1186 | A | 5'GGAATAAGCAGAAACTG-3' | (SEQ ID NO: 185) |
| 1186 | G | 5'GGAATAAGCGGAAACTG-3' | (SEQ ID NO: 186) |
| 2196 | G | 5'AAAAGACATGACAGCGA-3' | (SEQ ID NO: 187) |
| 2196 | A | 5'AAAAGACATAACAGCGA-3' | (SEQ ID NO: 188) |
| 3238 | G | 5'AAGAAGCCAGCTCAAGC-3' | (SEQ ID NO: 189) |
| 3238 | A | 5'AAGAAGCCAACTCAAGC-3' | (SEQ ID NO: 190) |
| 2202 | G | 5'CATGACAGTGATACTTT-3' | (SEQ ID NO: 191) |
| 2202 | A | 5'CATGACAGTAATACTTT-3' | (SEQ ID NO: 192) |

TABLE 10

BRCA2

| PROBE | | SEQUENCE | |
|---|---|---|---|
| 1093 | A | 5'TAGGACATTGGCATTGA-3' | (SEQ ID NO: 193) |
| 1093 | C | 5'TAGGACATGTGGCATTGA-3' | (SEQ ID NO: 194) |
| 1342 | A | 5'CTTCTGATTTGCTACATT-3' | (SEQ ID NO: 195) |
| 1342 | C | 5'CTTCTGATGTGCTACATT-3' | (SEQ ID NO: 196) |
| 1593 | A | 5'GGCTTCTCTGATTTTGGT-3' | (SEQ ID NO: 197) |
| 1593 | G | 5'GGCTTCTCGGATTTTGGT-3' | (SEQ ID NO: 198) |
| 2457 | T | 5'TTTTGAATATTGTACTGG-3' | (SEQ ID NO: 199) |
| 2457 | C | 5'TTTTGAATGTTGTACTGG-3' | (SEQ ID NO: 200) |
| 2908 | G | 5'ATTAGCTACTTGGAAGAC-3' | (SEQ ID NO: 201) |
| 2908 | A | 5'ATTAGCTATTTGGAAGAC-3' | (SEQ ID NO: 202) |
| 3199 | A | 5'CCATTTGTTCATGTAATC-3' | (SEQ ID NO: 203) |
| 3199 | G | 5'CCATTTGTCCATGTAATC-3' | (SEQ ID NO: 204) |
| 3624 | A | 5'TAGCTTGGTTTTCTAAAC-3' | (SEQ ID NO: 205) |
| 3624 | G | 5'TAGCTTGGCTTTCTAAAC-3' | (SEQ ID NO: 206) |
| 4035 | T | 5'ATTGAAACAACAGAATCA-3' | (SEQ ID NO: 207) |
| 4035 | C | 5'ATTGAAACGACAGAATCA-3' | (SEQ ID NO: 208) |
| 7470 | A | 5'TGAAAATGTGATTTAGTT-3' | (SEQ ID NO: 209) |
| 7470 | G | 5'TGAAAATGCGATTTAGTT-3' | (SEQ ID NO: 210) |
| 9079 | G | 5'TTCCATGGCCTTCCTAAT-3' | (SEQ ID NO: 211) |
| 9079 | A | 5'TTCCATGGTCTTCCTAAT-3' | (SEQ ID NO: 212) |

TABLE 11

PTEN

| | | | |
|---|---|---|---|
| 132 | C | 5'CTTGAAGGCGTATACAGG-3' | (SEQ ID NO: 213) |
| 132 | T | 5'CTTGAAGGTGTATACAGG-3' | (SEQ ID NO: 214) |

TABLE 12

BAP1

| | | |
|---|---|---|
| +1102 | 5'ATGGCCTCTACCAGATGGC-3' | (SEQ ID NO: 215) |
| +1102 | 5'ATGGCCTCTCCCAGATGGC-3' | (SEQ ID NO: 216) |
| +1102 | 5'ATGGCCTCTGCCAGATGGC-3' | (SEQ ID NO: 217) |
| +1102 | 5'ATGGCCTCTTCCAGATGGC-3' | (SEQ ID NO: 218) |
| +1116 | 5'CAGATGGCTTTGAAAAAGG-3' | (SEQ ID NO: 219) |
| +1116 | 5'CAGATGGCTTTGCAAAAGG-3' | (SEQ ID NO: 220) |
| +1116 | 5'CAGATGGCTTTGGAAAAGG-3' | (SEQ ID NO: 221) |
| +1116 | 5'CAGATGGCTTTGTAAAAGG-3' | (SEQ ID NO: 222) |
| +1131 | 5'GATCCAAACAGGCCCCTTT-3' | (SEQ ID NO: 223) |
| +1131 | 5'GATCCAACCAGGCCCCTTT-3' | (SEQ ID NO: 224) |
| +1131 | 5'GATCCAAGCAGGCCCCTTT-3' | (SEQ ID NO: 225) |
| +1131 | 5'GATCCAATCAGGCCCCTTT-3' | (SEQ ID NO: 226) |
| +1233 | 5'CCCTGTAAAAACTGGATCA-3' | (SEQ ID NO: 227) |
| +1233 | 5'CCCTGTAAACACTGGATCA-3' | (SEQ ID NO: 228) |
| +1233 | 5'CCCTGTAAAGACTGGATCA-3' | (SEQ ID NO: 229) |
| +1233 | 5'CCCTGTAAATACTGGATCA-3' | (SEQ ID NO: 230) |

Each labeling reaction contains 2-μl 5× Kinase buffer (or 1 μl of 10× Kinase buffer), 5 μl gamma-ATP $^{32}$P (not more than one week old), 1 μl T4 polynucleotide kinase, 3 μl oligonucleotide (20 μM stock), sterile H$_2$O to 10 μl final volume if necessary. The reactions are incubated at 37° C. for 30 minutes, then at 65° C. for 10 minutes to heat inactivate the kinase. The kinase reaction is diluted with an equal volume (10 μl) of sterile dH$_2$O (distilled water).

The oligonucleotides are purified on STE MICRO SELECT-D, G-25 spin columns (catalog no. 5303-356769), according to the manufacturer's instructions. The 20 μl synthetic oligonucleotide eluate is diluted with 80 μl dH$_2$O (final volume=100 μl). The amount of radioactivity in the oligonucleotide sample is determined by measuring the radioactive counts per minute (cpm). The total radioactivity must be at least 2 million cpm. For any samples containing less than 2 million total, the labeling reaction is repeated.

Hybridization with Oligonucleotides

Approximately 2–5 million counts of the labeled oligonucleotide probe is diluted into 5 ml of TMAC hybridization solution, containing 40 μl of 20 μM stock of unlabeled alternative polymorphism oligonucleotide. The probe mix is preheated to 52° C. in the hybridization oven. The prehybridization solution is removed from each bottle and replaced with the probe mix. The filter is hybridized for 1 hour at 52° C. with moderate agitation. Following hybridization, the probe mix is decanted into a storage tube and stored at –20° C. The filter is rinsed by adding approximately 20 ml of 2×SSC+0.1% SDS at room temperature and rolling the capped bottle gently for approximately 30 seconds and pouring off the rinse. The filter is then washed with 2×SSC+0.1% SDS at room temperature for 20 to 30 minutes, with shaking.

The membrane is removed from the wash and placed on a dry piece of 3MM WHATMAN filter paper then wrapped in one layer of plastic wrap, placed on the autoradiography film, and exposed for about five hours depending upon a survey meter indicating the level of radioactivity. The film is developed in an automatic Film processor.

Control Hybridization with Normal Oligonucleotides

The purpose of this step is to ensure that the PCR products are transferred efficiently to the nylon membrane.

Following hybridization with the bound oligonucleotide, as described above, each nylon membrane is washed in 2×SSC, 0.1% SDS for 20 minutes at 65° C. to melt off the bound oligonucleotide probes. The nylon strips are then prehybridized together in 40 ml of TMAC hybridization solution for at least 1 hour at 52° C. in a shaking water bath. 2–5 million counts of each of the normal labeled oligonucleotide probes plus 40 μl of 20 μM stock of unlabeled normal oligonucleotide are added directly to the container containing the nylon membranes and the prehybridization solution. The filter and probes are hybridized at 52° C. with shaking for at least 1 hour. Hybridization can be performed overnight, if necessary. The hybridization solution is poured off, and the nylon membrane is rinsed in 2×SSC, 0.1% SDS for 1 minute with gentle swirling by hand. The rinse is poured off and the membrane is washed in 2×SSC, 0.1% SDS at room temperature for 20 minutes with shaking.

The nylon membrane is removed and placed on a dry piece of 3MM WHATMAN filter paper. The nylon membrane is then wrapped in one layer of plastic wrap and placed on autoradiography film. The exposure is for at least 1 hour.

For each sample, adequate transfer to the membrane is indicated by a strong autoradiographic hybridization signal. For each sample, an absent or weak signal when hybridized with its normal oligonucleotide, indicates an unsuccessful transfer of PCR product, and it is a false negative. The ASO analysis must be repeated for any sample that did not successfully transfer to the nylon membrane.

The pattern of hybridization using the probes from the panel according to Tables 9–12 determine the haplotype of the patient sample when compared to the known haplotypes.

The degree of breast, ovarian and other cancer prevention with and without tamoxifen and the degree of prevention of reoccurrence of breast and ovarian cancer with and without tamoxifen are compared for patients grouped by BRCA1, BRCA2, PTEN, BAP1, BARD1, hRAD51 haplotype separately and in all possible combinations using various proprietary data mining techniques similar to the Recognizer™ methodology described in U.S. Pat. No. 5,642,936. Appropriate recommendations regarding the use of tamoxifen for patients of different haplotypes are then be made for patients with and without a history of breast or ovarian cancer.

While this example is a retrospective study and thus unacceptable for proof of efficacy for the U.S. Food and Drug Administration, prospective studies are also part of the present invention. In a prospective study, the test individuals have their haplotypes determined for each pertinent gene prior to determining whether or not they will be accepted for the drug trial or initiate tamoxifen therapy.

EXAMPLE 6

Pharmacogenetic Analysis of a p53 Polymorphism and the Appropriateness of the Human Papiloma Virus Vaccine Human papiloma virus (HPV) currently infects up to 40 million Americans with at least one of about 80 different strains. Many strains of the virus cause veneral warts, vulval, penile and perianal cancers. One strain in particular, HPV-16, is believed to be responsible for about half of all cases of cervical cancer. Three other strains are responsible for another 35% of all cervical cancer cases with HPV-18 causing malignant tumors while HPV-6 and HPV-11 usually forming benign lesions. HPV vaccines are made by MedImmune, Inc. (Gaithersburg, Md.) and Merck & Co. Clinical trials have already begun.

While applicant does not wish to be bound by any theory, it is believed that HPV may induce cancer by interacting with p53 in a manner which inhibits the action of p53 to prevent runaway cell growth. It has been known that HPV protein E6 inactivates only p53 proteins from some individuals and not other individuals. Medcalf et al, *Oncogene*, 8: 2847–2851 (1993). Therefore, determining the haplotype(s) of the p53 gene is believed to indicate who is susceptible to cervical cancer induced by HPV and is therefore a candidate for a HPV vaccine.

Previous commercial p53 gene testing of patient samples performed by Oncormed, Inc. (the owner of this application) involved various sequencing techniques and functional assays for prognostic testing on various tumor samples and susceptibility testing of genomic samples in patients with an inherited mutant p53 gene (Li-Fraumeni Syndrome). While apparent single nucleotide polymorphisms were noticed, such results were not reported as the samples are suspected to contain p53 mutations and do not originate from healthy individuals without a genetic history indicating inheritance of two functional p53 alleles.

Only polymorphisms in the coding region are analyzed because women having cervical cancers are believed to have a p53 protein which is "in-activatable" because the coding sequence for p53 is usually not mutated in cervical cancers. Vogelstein et al, *Cell*, 70: 523–526 (1992). Thus, the haplotypes were determined based on the single nucleotide polymorphisms at codon 21 (which may be either GAC or GAT), codon 36 (which may be either CCG or CCA), codon 47 (which may be either C CG or T CG), codon 72 (which may be either CGC or CCC) and codon 213 (which may be either CGA or CGG).

Experimental Protocol

Blood samples are from 53 healthy individuals having a history of veneral warts or at risk from exposure to HPV. Exposure is defined as an individual having regular sexual contact with an infected individual without a barrier preventing transmission of HPV. These individuals have either stage I (normal) or stage II (inflammation) PAP smears. Some of the individuals had been previously treated for veneral warts with one or more of the following treatments: podophyllin, trichloroacetic acid, cryosurgury, cauderization or interferon. Also, blood samples are from 12 patients with a history of cervical cancer as defined by a stage IV (carcinoma in-situ) or greater PAP smear result. Note that individuals having a stage III PAP smear (dysplasia) are not included in this study. White blood cells are collected and genomic DNA is extracted from the white blood cells according to well-known methods (Sambrook, et al., Molecular Cloning, A Laboratory Manual, 2nd Ed., 1989, Cold Spring Harbor Laboratory Press, at 9.16–9.19).

PCR Amplification for Sequencing

The genomic DNA is used as a template to amplify a DNA fragment encompassing the site of the mutation to be tested. The 25 ml PCR reaction contains the following components: 1 ml template (100 ng/ml) DNA, 2.5 ml 10×PCR Buffer (PERKIN-ELMER), 1.5 ml dNTP (2 mM each dATP, dCTP, dGTP, dTTP), 1.5 ml Forward Primer (10 mM), 1.5 ml Reverse Primer (10 mM), 0.5 ml (2.5 U total) AMPLITAQ GOLD™ TAQ DNA POLYMERASE or AMPLITAQ® TAQ DNA POLYMERASE (PERKIN-ELMER), 1.0 to 5.0 ml (25 mM) MgCl₂ (depending on the primer) and distilled water (dH₂O) up to 25 ml. All reagents for each exon except the genomic DNA can be combined in a master mix and aliquoted into the reaction tubes as a pooled mixture. The primers are listed below.

-continued

| Temperature | Time | Number of Cycles |
|---|---|---|
| 72° C. | 5 min. | 1 |
| 4° C. | hold | 1 |

Quality Control Agarose Gel of PCR Amplification:

The quality of the PCR products is examined prior to further analysis by electrophoresing an aliquot of each PCR

| NAME | SEQUENCE | | LENGTH | INTRON |
|---|---|---|---|---|
| 2F | 5'-TCATGCTGGATCCCCACTTTTCCTCTTG-3' | (SEQ ID NO: 231) | 28 | 31 |
| 2R | 5'-GGTGGCCTGCCCTTCCAATGGATCCACT-3' | (SEQ ID NO: 232) | 28 | 3 |
| 3F | 5'-AATTCATGGGACTGACTTTCTGCTCTTGTC-3' | (SEQ ID NO: 233) | 30 | 6 |
| 3R | 5'-TCCAGGTCCCAGCCCAACCCTTGTCC-3' | (SEQ ID NO: 234) | 26 | 4 |
| 4F | 5'-GTCCTCTGACTGCTCTTTTCACCCATCTAC-3' | (SEQ ID NO: 235) | 30 | 2 |
| 4R | 5'-GGGATACGGCCAGGCATTGAAGTCTC-3' | (SEQ ID NO: 236) | 26 | 29 |
| 5F | 5'-CTTGTGCCCTGACTTTCAACTCTGTCTC-3' | (SEQ ID NO: 237) | 28 | 16 |
| 5R | 5'-TGGGCAACCAGCCCTGTCGTCTCTCCA-3' | (SEQ ID NO: 238) | 27 | 15 |
| 6F | 5'-CCAGGCCTCTGATTCCTCACTGATTGCTC-3' | (SEQ ID NO: 239) | 29 | 4 |
| 6R | 5'-GCCACTGACAACCACCCTTAACCCCTC-3' | (SEQ ID NO: 240) | 27 | 29 |
| 7F | 5'-GCCTCATCTTGGGCCTGTGTTATCTCC-3' | (SEQ ID NO: 241) | 27 | 3 |
| 7R | 5'-GGCCAGTGTGCAGGGTGGCAAGTGGCTC-3' | (SEQ ID NO: 242) | 28 | 5 |
| 8F | 5'-GTAGGACCTGATTTCCTTACTGCCTCTTGC-3' | (SEQ ID NO: 243) | 30 | 23 |
| 8R | 5'-ATAACTGCACCCTTGGTCTCCTCCACCGC-3' | (SEQ ID NO: 244) | 29 | 20 |
| 9F | 5'-CACTTTTATCACCCTTTCCTTGCCTCTTTCC-3' | (SEQ ID NO: 245) | 30 | 3 |
| 9R | 5'-AACTTTCCACTTGATAAGAGGTCCCAAGAC-3' | (SEQ ID NO: 246) | 30 | 7 |
| 10F | 5'-ACTTACTTCTCCCCCTCCTCTGTTGCTGC-3' | (SEQ ID NO: 247) | 29 | 2 |
| 10R | 5'-ATGGAATCCTATGGCTTTCCAACCTAGGAAG-3' | (SEQ ID NO: 248) | 31 | 39 |
| 11F | 5'-CATCTCTCCTCCCTGCTTCTGTCTCCTAC-3' | (SEQ ID NO: 249) | 29 | 2 |
| 11R | 5'-CTGACGCACACCTATTGCAAGCAAGGGTTC-3' | (SEQ ID NO: 250) | 30 | 80 |

The term "INTRON" refers to the location in the intron where the primer anneals.

Alternatively the primers for exons 2 and 3 may be amplified together with primers:

p53-2/3F 5'GAAGCGTCTCATGCTGGAT-3' (SEQ ID NO: 251)

p53-2/3R 5'GGGGACTGTAGATGGGTGAA-3' (SEQ ID NO: 252)

For each exon analyzed, the following control PCRs are set up:

(1) "Negative" DNA control (100 ng placental DNA (SIGMA CHEMICAL CO., St. Louis, Mo.)

(2) Three "no template" controls

PCR for all exons is performed using the following thermocycling conditions:

| Temperature | Time | Number of Cycles |
|---|---|---|
| 95° C. | 5 min (AMPLITAQ) or 10 min. (GOLD) | 1 |
| 95° C. | 30 sec. | |
| 55° C. | 30 sec. | 30 cycles |
| 72° C. | 1 min | | reaction sample on an agarose gel. 5 μl of each PCR reaction is run on an agarose gel along side a DNA 100 BP DNA LADDER (Gibco BRL cat#15628-019). The electrophoresed PCR products are analyzed according to the following criteria:

Each patient sample must show a single band of the size corresponding the number of base pairs expected from the length of the PCR product from the forward primer to the reverse primer. If a patient sample demonstrates smearing or multiple bands, the PCR reaction must be repeated until a clean, single band is detected. If no PCR product is visible or if only a weak band is visible, but the control reactions with placental DNA template produced a robust band, the patient sample should be re-amplified with 2× as much template DNA.

All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

The optimum amount of PCR product on the gel should be between 50 and 100 ng, which can be determined by comparing the intensity of the patient sample PCR products with that of the DNA ladder. If the patient sample PCR products contain less than 50 to 100 ng, the PCR reaction should be repeated until sufficient quantity is obtained.

DNA Sequencing

For DNA sequencing, double stranded PCR products are labeled with four different fluorescent dyes, one specific for each nucleotide, in a cycle sequencing reaction. With Dye Terminator Chemistry, when one of these nucleotides is incorporated into the elongating sequence it causes a termination at that point. Over the course of the cycle sequencing reaction, the dye-labeled nucleotides are incorporated along the length of the PCR product generating many different length fragments.

The dye-labeled PCR products will separate according to size when electrophoresed through a polyacrylamide gel. At the lower portion of the gel on an ABI automated sequencer, the fragments pass through a region where a laser beam continuously scans across the gel. The laser excites the fluorescent dyes attached to the fragments causing the emission of light at a specific wavelength for each dye. Either a photomultiplier tube (PMT) detects the fluorescent light and converts is into an electrical signal (ABI 373) or the light is collected and separated according to wavelength by a spectrograph onto a cooled, charge coupled device (CCD) camera (ABI 377). In either case the data collection software will collect the signals and store them for subsequent sequence analysis.

PCR products are first purified for sequencing using a QIAQUICK-SPIN PCR PURIFICATION KIT (QIAGEN #28104). The purified PCR products are labeled by adding primers, fluorescently tagged dNTPs and Taq Polymerase FS in an ABI Prism Dye Terminator Cycle Sequencing Kit (PERKIN ELMER/ABI catalog #02154) in a PERKIN ELMER GENEAMP 9600 thermocycler.

The amounts of each component are:

| For Samples | | For Controls | |
|---|---|---|---|
| Reagent | Volume | Reagent | Volume |
| Dye mix | 8.0 μL | PGEM | 2.0 μL |
| Primer (1.6 mM) | 2.0 μL | M13 | 2.0 μL |
| PCR product | 2.0 μL | Dye mix | 8.0 μL |
| sdH2O | 8.0 μL | sdH2O | 8.0 μL |

The thermocycling conditions are:

| Temperature | Time | # of Cycles |
|---|---|---|
| 96° C. | 15 sec. | |
| 50° C. | 5 sec. | 25 |
| 60° C. | 4 min. | |
| 4° C. | hold | 1 |

The product is then loaded into a gel and placed into an ABI DNA Sequencer (Models 373A & 377) and run. The sequence obtained is analyzed by comparison to the wild type (reference) sequence using SEQUENCE NAVIGATOR software. When a sequence does not align, it indicates a possible mutation or polymorphism. The DNA sequence is determined in both the forward and reverse directions. All results are provided to a second reader for review.

PCR Amplification for ASO

The genomic DNA is used as a template to amplify a separate DNA fragment encompassing the site of the mutation to be tested. The 50 μl PCR reaction contains the following components: 1 μl template (100 ng/μl) DNA, 5.0 μl 10×PCR Buffer (PERKIN-ELMER), 2.5 μl dNTP (2 mM each dATP, dCTP, dGTP, dTTP), 2.5 μl Forward Primer (10 mM), 2.5 μl Reverse Primer (10 μM), 0.5 μl (2.5 U total) AMPLITAQ® TAQ DNA POLYMERASE or AMPLITAQ GOLD™ DNA POLYMERASE (PERKIN-ELMER), 1.0 to 5.0 μl (25 mM) MgCl$_2$ (depending on the primer) and distilled water (dH$_2$O) up to 50 μl. All reagents for each exon except the genomic DNA can be combined in a master mix and aliquoted into the reaction tubes as a pooled mixture. The primers described above are used.

For each exon analyzed, the following control PCRs are set up:

(1) "Negative" DNA control (100 ng placental DNA (SIGMA CHEMICAL CO., St. Louis, Mo.)
(2) Three "no template" controls.

PCR for all exons is performed using the following thermocycling conditions:

| Temperature | Time | Number of Cycles |
|---|---|---|
| 95° C. | 5 min (AMPLITAQ) or 10 min. (GOLD) | 1 |
| 95° C. | 30 sec. | |
| 55° C. | 30 sec. | 30 cycles |
| 72° C. | 1 min | |
| 72° C. | 5 min. | 1 |
| 4° C. | hold | 1 |

The quality control agarose gel of PCR amplification is performed as above.

Binding PCR Products to Nylon Membrane

The PCR products are denatured no more than 30 minutes prior to binding the PCR products to the nylon membrane. To denature the PCR products, the remaining PCR reaction (45 μl) and the appropriate positive control polymorphism gene amplification product are diluted to 200 μl final volume with PCR Diluent Solution (500 mM NaOH, 2.0 M NaCl, 25 mM EDTA) and mixed thoroughly. The mixture is heated to 95° C. for 5 minutes, and immediately placed on ice and held on ice until loaded onto dot blotter, as described below.

The PCR products are bound to 9 cm by 13 cm nylon ZETA PROBE BLOTTING MEMBRANE (BIO-RAD, Hercules, Calif., catalog number 162-0153) using a BIO-RAD dot blotter apparatus.

Pieces of 3MM filter paper [WHATMAN®, Clifton, N.J.] and nylon membrane are pre-wet in 10×SSC prepared fresh from 20×SSC buffer stock. The vacuum apparatus is rinsed thoroughly with dH$_2$O prior to assembly with the membrane. 100 μl of each denatured PCR product is added to the wells of the blotting apparatus. Each row of the blotting apparatus contains a set of reactions for a single exon to be tested, including a placental DNA (negative) control, a synthetic oligonucleotide with the desired mutation or a PCR product from a known polymorphic sample (positive control), and three no template DNA controls.

After applying PCR products, the nylon filter is placed DNA side up on a piece of 3MM filter paper saturated with denaturing solution (1.5 M NaCl, 0.5 M NaOH) for 5 minutes. The membrane is transferred to a piece of 3MM filter paper saturated with neutralizing solution (1 M Tris-HCl, pH 8, 1.5 M NaCl) for 5 minutes. The neutralized membrane is then transferred to a dry 3MM filter DNA side up, and exposed to ultraviolet light (STRALINKER, STRATAGENE, La Jolla, Calif.) for exactly 45 seconds to fix the DNA to the membrane. This UV crosslinking should be performed within 30 min. of the denaturation/neutralization steps. The nylon membrane is then cut into strips such that each strip contains a single row of blots of one set of reactions for a single exon.

Hybridizing Labeled Oligonucleotides to the Nylon Membrane Prehybridization

The strip is prehybridized at 52° C. incubation using the HYBAID® (SAVANT INSTRUMENTS, INC., Holbrook, N.Y.) hybridization oven. 2×SSC (15 to 20 ml) is preheated to 52° C. in a water bath. For each nylon strip, a single piece of nylon mesh cut slightly larger than the nylon membrane strip (approximately 1"×5") is pre-wet with 2×SSC. Each single nylon membrane is removed from the prehybridization solution and placed on top of the nylon mesh. The membrane/mesh "sandwich" is then transferred onto a piece of Parafilm™. The membrane/mesh sandwich is rolled lengthwise and placed into an appropriate HYBAID® bottle, such that the rotary action of the HYBAID® apparatus caused the membrane to unroll. The bottle is capped and gently rolled to cause the membrane/mesh to unroll and to evenly distribute the 2×SSC, making sure that no air bubbles formed between the membrane and mesh or between the mesh and the side of the bottle. The 2×SSC is discarded and replaced with 5 ml TMAC Hybridization Solution, which contains 3 M TMAC (tetramethyl ammoniumchloride-SIGMA T-3411), 100 mM $Na_3PO_4$(pH 6.8), 1 mM EDTA, 5× Denhardt's (1% Ficoll, 1% polyvinylpyrrolidone, 1% BSA (fraction V)), 0.6% SDS, and 100 mg/ml Herring Sperm DNA. The filter strips are prehybridized at 52° C. with medium rotation (approx. 8.5 setting on the HYBAID® speed control) for at least one hour. Prehybridization can also be performed overnight.

Labeling Oligonucleotides

The DNA sequences of the numerous oligonucleotide probes are used to detect the p53 mutation. For each mutation, a polymorphic and a normal oligonucleotide must be labeled. While only five pairs of oligonucleotide probes are listed below, corresponding oligonucleotides for each mutation may be prepared and used in the same manner.

Polymorphism in Codon 21 wildtype 5'TTTTCAGACCTATGGAAAC-3' (SEQ ID NO: 253)
other wt 5'TTTCAGATCTATGGAAAC-3' (SEQ ID NO: 254)

Polymorphism in Codon 36 wildtype 5'CCCTTGCCGTCCCAAGCA-3' (SEQ ID NO: 255)
other wt 5'CCCTTGCCATCCCAAGCA-3' (SEQ ID NO: 256)

Polymorphism in Codon 47 wildtype 5'CTGTCCCCGGACGATATT-3' (SEQ ID NO: 257)
other wt 5'CTGTCCCCAGACGATATT-3' (SEQ ID NO: 258)

Polymorphism in Codon 72

Polymorphism in Codon 213 wildtype 5'ACTTTTCGACATAGTGTG-3' (SEQ ID NO: 261)
other wt 5'ACTTTTCGGCATAGTGTG-3' (SEQ ID NO: 262)

Each labeling reaction contains 2 µl 5× Kinase buffer (or 1 µl of 10× Kinase buffer), 5 µl gamma-ATP $^{32}$P (not more than one week old), 1 µl T4 polynucleotide kinase, 3 µl oligonucleotide (20 µM stock), sterile $H_2O$ to 10 µl final volume if necessary. The reactions are incubated at 37° C. for 30 minutes, then at 65° C. for 10 minutes to heat inactivate the kinase. The kinase reaction is diluted with an equal volume (10 µl) of sterile $dH_2O$ (distilled water).

The oligonucleotides are purified on STE MICRO SELECT-D, G-25 spin columns (catalog no. 5303-356769), according to the manufacturer's instructions. The 20 µl synthetic oligonucleotide eluate is diluted with 80 µl $dH_2O$ (final volume=100 µl). The amount of radioactivity in the oligonucleotide sample is determined by measuring the radioactive counts per minute (cpm). The total radioactivity must be at least 2 million cpm. For any samples containing less than 2 million cpm total, the labeling reaction is repeated.

Hybridization with Oligonucleotides

Approximately 2–5 million cpm of the labeled polymorphic oligonucleotide probe is diluted into 5 ml of TMAC hybridization solution, containing 40 µl of 20 µM stock of unlabeled normal oligonucleotide. The probe mix is preheated to 52° C. in the hybridization oven. The prehybridization solution is removed from each bottle and replaced with the probe mix. The filter is hybridized for 1 hour at 52° C. with moderate agitation. Following hybridization, the probe mix is decanted into a storage tube and stored at –20° C. The filter is rinsed by adding approximately 20 ml of 2×SSC+0.1% SDS at room temperature and rolling the capped bottle gently for approximately 30 seconds and pouring off the rinse. The filter is then washed with 2×SSC+0.1% SDS at room temperature for 20 to 30 minutes, with shaking.

The membrane is removed from the wash and placed on a dry piece of 3MM WHATMAN filter paper then wrapped in one layer of plastic wrap, placed on the autoradiography film, and exposed for about five hours depending upon a survey meter indicating the level of radioactivity. The film is developed in an automatic film processor.

Control Hybridization with Normal Oligonucleotides

The purpose of this step is to ensure that the PCR products are transferred efficiently to the nylon membrane.

Following hybridization with the polymorphic oligonucleotide each nylon membrane is washed in 2×SSC, 0.1% SDS for 20 minutes at 65° C. to melt off the polymorphic oligonucleotide probes. The nylon strips are then prehybridized together in 40 ml of TMAC hybridization solution for at least 1 hour at 52° C. in a shaking water bath. 2–5 million counts of each of the normal labeled oligonucleotide probes plus 40 ml of 20 mM stock of unlabeled normal oligonucleotide are added directly to the container containing the nylon membranes and the prehybridization solution. The filter and probes are hybridized at 52° C. with shaking for at least 1 hour. Hybridization can be performed overnight, if necessary. The hybridization solution is poured off, and the nylon membrane is rinsed in 2×SSC, 0.1% SDS for 1 minute with gentle swirling by hand. The rinse is poured off and the membrane is washed in 2×SSC, 0.1% SDS at room temperature for 20 minutes with shaking.

The nylon membrane is removed placed on a dry piece of 3MM WHATMAN filter paper. The nylon membrane is then wrapped in one layer of plastic wrap and placed on autoradiography film, and exposure is for at least 1 hour.

For each sample, adequate transfer to the membrane is indicated by a strong autoradiographic hybridization signal. For each sample, an absent or weak signal when hybridized with its normal oligonucleotide, indicates an unsuccessful transfer of PCR product, and it is a false negative. The ASO analysis must be repeated for any sample that did not successfully transfer to the nylon membrane.

Homozygous individuals having haplotypes with the single nucleotide polymorphism (SNP) arginine at codon 72 are overrepresentated in the genomic alleles of cervical cancer patients. In addition, it was recently published that cervical tumors have the SNP arginine at codon 72 at significantly higher frequency than normal tissue. Storey et al, Nature, 393: 229–234 (1998). Healthy women having such haplotypes are candidates for the HPV vaccines to prevent HPV invection, treat veneral warts, treat cervical and other related cancers, and prevent reoccurrence of veneral warts previously treated.

EXAMPLE 7

Pharmacogenetic Analysis of P1Haplotype and Platelet Sensitivity to Aspirin

Aspirin has been a standard anticoagulant therapy for patients who have had a heart attack. In recent years, aspirin therapy has been extended to individuals with a history or at risk for stroke (apoplexy) and phlebitis. It has even been proposed that every person over 50 years of age should take aspirin.

However, some people cannot take aspirin due to allergy, erosion of the stomach lining etc. Furthermore, research has shown that aspirin prevents heart attacks in about 40 percent of patients taking aspirin. Thus, it is desirable to determine which people will respond to aspirin and which will not in order to administer other anticoagulant or antiplatelet medication.

Platlet aggregation is recognized as an important step in the formation of a blockage which will cause a myocardial infarction and unstable angina. Platlet aggregration is based on glycoprotein gpIIb/IIIa. Different forms of this glycoprotein have been known. Weiss et al, Tissue Antigens, 46: 374–381 (1995), Kunicki et al, Molecular Immunology 16: 353–60 (1979). Methods for determining various polymorphisms may be done by DNA analysis. Newman et al, Journal of Clinical Investigation 83:1778–81 (1989). It has been reported that patients having one polymorphic form of the PI gene have a higher incidence for acute coronary thrombosis, particularly in patients younger than 60. Weiss et al, New England Journal of Medicine 334(17): 1090–1094 (1996). However, these findings were contradicted by Ridker, et al, Lancet 349: 385–388 (1997) with comments in Lancet on pages 370–371, 1099–1100 and 1100–1. Adding to the debate, it was recently published that platelet aggregation from haplotype $PI^{A2}$ containing individuals are less inhibited by aspirin at certain concentrations than individuals homozygous for haplotype $PI^{A1}$. Cooke et al, Lancet 351: 1253 (1998).

Resolving the issue for people at risk of heart attacks, stroke and other thrombogenic disorders is desirable, particularly in distinguishing between those who can take aspirin or who should take other medication which is more costly and with greater side effects.

Experimental Protocol

Blood samples are taken from 50 healthy individuals ages 50–55. Family history and personal histories of heart disease and other thrombogenic disorders are recorded. White blood cells are collected and genomic DNA is extracted from the white blood cells, PCR amplified and the sequence determined by ASO or sequenced as in the Examples above using different primers and probes. Newman et al., Journal of Clinical Investigation 83:1778–81 (1989). As before, PCR primers and ASO probes are designed to type these individuals for exon 2 to determine which base exists at nucleotide position 1565: a T or a C. at the amino acid level, codon 33 is changed from a leucine to a proline.

Individuals having haplotype $PI^{A2}$ either in homozygous or heterozygous form are instructed to either take high dosages of aspirin (2000 mg per day) or not take aspirin and given other medication appropriate for their individual needs. Individuals homozygous for haplotype $PI^{A1}$ are instructed to take aspirin at low dosages (350 mg per day)

The present invention is not to be limited in scope by the specific embodiments described herein. Indeed, various modifications of the invention in addition to those described herein will become apparent to those skilled in the art from the foregoing description and accompanying figure. Such modifications are intended to fall within the scope of the appended claims.

Various publications are cited herein, the disclosures of which are incorporated by reference in their entireties.

What is claimed is:

1. A method for determining an omi haplotype of a human BRCA1 gene comprising:

(a) determining the nucleotide sequence of the BRCA1 gene or fragment thereof from at least one female individual with a family history which indicates a predisposition to breast cancer, (b) comparing the determined nucleotide sequence from said female individual to SEQ ID NO: 263, and (c) determining the presence of the following nucleotide variations: thymine at nucleotides 2201 and 2731, cytosine at nucleotides 2430 and 4427, and guanine at nucleotides 3232, 3667 and 4956, wherein the presence of the nucleotide variations in the determined nucleotide sequence indicates the omi1 haplotype.

2. The method of claim 1 further comprising repeating steps (a) and (b).

3. The method of claim 1 wherein at least one nucleotide variation is located in an exon coding region of the BRCA1 gene.

4. The method of claim 3 wherein at least one nucleotide variation encodes an amino acid variation in the protein encoded by the BRCA 1 gene.

5. The method of claim 1 wherein the BRCA1 gene or fragment thereof is amplified prior to nucleotide sequencing.

6. The method of claim 1 further comprising comparing the determined nucleotide sequence to SEQ ID NO: 265.

7. The method of claim 1 further comprising comparing the determined nucleotide sequence to SEQ ID NO: 267.

8. The method of claim 1 further comprising determining the putative amino acid sequence of the protein encoded by the BRCA1 gene.

9. The method of claim 8 further comprising comparing the determined putative amino acid sequence to SEQ ID NO: 264.

10. The method of claim 8 further comprising comparing the determined putative amino acid sequence to SEQ ID NO: 266.

11. The method of claim 8 further comprising comparing the determined putative amino acid sequence to SEQ ID NO: 268.

12. The method of claim 1 wherein the nucleotide sequence or fragment thereof of the BRCA1 gene is determined in at least five female individuals with a family history which indicates a predisposition to breast cancer.

13. A method for determining an omi haplotype of a human BRCA1 gene comprising:

(a) determining the nucleotide sequence of the BRCA1 gene or fragment thereof from at least one female individual with a family history which indicates a predisposition to breast cancer, (b) determining the putative amino acid sequence of the protein or fragment thereof encoded by the BRCA1 gene from the determined nucleotide sequence, (c) comparing the putative amino acid sequence from said human to SEQ ID NO: 264, and (d) determining the presence of the following amino acid variations: proline at position 871, glutamate at residue 1038, lysine at residue 1183 and serine at residue 1613 wherein the presence of the variations in the determined amino acid sequence indicates the presence of the omi1 haplotype.

14. The method of claim 13 further comprising comparing the determined putative amino acid sequence to SEQ ID NO: 266.

15. The method of claim 13 further comprising comparing the determined putative amino acid sequence to SEQ ID NO: 268.

16. The method of claim 13 wherein the putative amino acid sequence or fragment thereof of the protein encoded by the BRCA1 gene is determined in at least five female individuals with a family history which indicates a predisposition to breast cancer.

17. A method for determining an omi haplotype of a human BRCA1 gene consisting essentially of:

(a) determining the nucleotide sequence of the BRCA1 gene or fragment thereof from at least one female individual with a family history which indicates a predisposition to breast cancer, (b) comparing the determined nucleotide sequence from said female individual to SEQ ID NO: 263, and (c) determining the presence of the following nucleotide variations: thymine at nucleotides 2201 and 2731, cytosine at nucleotides 2430 and 4427, and guanine at nucleotides 3232, 3667 and 4956, wherein the presence of the nucleotide variations in the determined nucleotide sequence indicates the omi1 haplotype.

18. A method for determining an omi haplotype of a human BRCA1 gene consisting essentially of:

(a) determining the nucleotide sequence of the BRCA1 gene or fragment thereof from at least one female individual with a family history which indicates a predisposition to breast cancer, (b) determining the putative amino acid sequence of the protein or fragment thereof encoded by the BRCA1 gene from the determined nucleotide sequence, (c) comparing the putative amino acid sequence from said human to SEQ ID NO: 264, and (d) determining the presence of the following amino acid variations: proline at position 871, glutamate at residue 1038, lysine at residue 1183 and serine at residue 1613 wherein the presence of the variations in the determined amino acid sequence indicates the presence of the omi1 haplotype.

19. The method according to any of claim 1, 13, 17 or 18 wherein the determined omi1 haplotype of the human BRCA1 gene is not associated with a predisposition to developing breast cancer.

* * * * *